(12) United States Patent
Subiza Garrido-Lestache et al.

(10) Patent No.: US 9,901,633 B2
(45) Date of Patent: Feb. 27, 2018

(54) IMMUNOGENIC COMPLEX FOR VACCINATION AND METHOD FOR THE PRODUCTION THEREOF

(71) Applicant: INMUNOTEK, S.L., Alcalá de Henares (Madrid) (ES)

(72) Inventors: José Luis Subiza Garrido-Lestache, Alcalá de Henares (ES); Javier Cañada Vicinay, Alcalá de Henares (ES); Irene Soria Castro, Alcalá de Henares (ES); Enrique Fernández-Caldas Rodríguez, Alcalá de Henares (ES); Ana Manzano Pérez, Alcalá de Henares (ES); Bárbara Cases Ortega, Alcalá de Henares (ES); Jesús Jiménez Barbero, Alcalá de Henares (ES); Miguel Casanovas Vergés, Alcalá de Henares (ES)

(73) Assignee: IMMUNOTEK, S.L., Alcalá de Henares (Madrid) (ES)

( * ) Notice: Subject to any disclaimer, the term of this patent is extended or adjusted under 35 U.S.C. 154(b) by 14 days.

(21) Appl. No.: 14/781,733

(22) PCT Filed: Apr. 3, 2014

(86) PCT No.: PCT/ES2014/070263
§ 371 (c)(1),
(2) Date: Oct. 1, 2015

(87) PCT Pub. No.: WO2014/162036
PCT Pub. Date: Oct. 9, 2014

(65) Prior Publication Data
US 2016/0058859 A1    Mar. 3, 2016

(30) Foreign Application Priority Data
Apr. 3, 2013 (ES) ................................ 201330474

(51) Int. Cl.
*A61K 39/35* (2006.01)
*A61K 39/39* (2006.01)
*A61K 39/00* (2006.01)

(52) U.S. Cl.
CPC .............. *A61K 39/35* (2013.01); *A61K 39/39* (2013.01); *A61K 2039/55583* (2013.01)

(58) Field of Classification Search
None
See application file for complete search history.

(56) References Cited

U.S. PATENT DOCUMENTS

2007/0092531 A1    4/2007    McKenzie et al.

FOREIGN PATENT DOCUMENTS

| JP | H08092297 | 4/1996 |
| JP | 2003506321 | 2/2003 |
| JP | 2004043332 | 2/2004 |
| JP | 2004097211 | 4/2004 |
| JP | 201193926 | 5/2011 |
| JP | 5249482 | 4/2013 |
| WO | WO-2000077178 | 12/2000 |
| WO | WO-2004047794 | 6/2004 |
| WO | WO-2011140595 | 11/2011 |

OTHER PUBLICATIONS

PCT Search Report and Written Opinion dated Aug. 5, 2014, PCT Appln. No. PCT/ES2014/070263, 16 pages.
Weinberger, Esther E., et al., "Generation of hypoallergenic neoglycoconjugates for dendritic cell targeted vaccination: A novel tool for specific immunotherapy", Journal of Controlled Release, vol. 165, No. 2, (Nov. 10, 2012), 101-109.
Durana, et al., "Functionalization of mannans from pathogenic yeasts by different means of oxidations—preparation of precursors for conjugation reactions with respect to preservation of immunological properties", Carbohydrate Polymers vol. 63, (2006), 72-81.
Hemmer, et al., "Identification by immunoblot of venom glycoproteins displaying immunoglobulin E-binding N-glycans as cross-reactive allergens in honeybee and yellow jacket venom", Clin Exp Allergy vol. 34, (2004), 460-469.
Kristiansen, et al., "Periodate oxidation of polysaccharides for modification of chemical and physical properties", Carbohydrate Research vol. 345, (2010), 1264-1271.
Manzano, et al., "Structural studies of novel glycoconjugates from polymerized allergens (allergoids) and mannans as allergy vaccines", Glycoconj J vol. 33, (2016), 93-101.
Masarova, et al., "Optimization of Dextran and Mannan Dialdehydes Preparation and Examination of their Biospecific Interaction with Concanavalin A", Chem. Pap. vol. 55(2), (2001), 130-135.
Misaki, et al., "Purification and Characterization of the alpha-1,3-Mannosylmannose-recognizing Lectin of Crocus vernus Bulbs", The Journal of Biological Chemistry vol. 272, No. 41, Issue of Oct. 10, (1997), 25455-25461.
Schulke, et al., "Dendritic cell targeting with C-type lectins for improvement of allergen immunotherapy", J Allergy Clin Immunol vol. 138, (2016), 568-570.
Sheng, et al., "Mannan derivatives induce phenotypic and functional maturation of mouse dendritic cells", Blackwell Publishing Ltd, Immunology, vol. 118, (2006), 372-383.
Sirvent, et al., "Novel vaccines targeting dendritic cells by coupling allergoids to nonoxidized mannan enhance allergen uptake and induce functional regulatory T cells through programmed death ligand 1", J Allergy Clin Immunol, vol. 138, No. 2, (Aug. 2016), 558-567.e11.
Soria, et al., "Mite allergoids coupled to nonoxidized mannan from *Saccharomyces cerevisae* effciently target canine dendritic cells for novel allergy immunotherapy in veterinary medicine", Veterinary Immunology and Immunopathology vol. 190, (2017), 65-72.

(Continued)

*Primary Examiner* — Jennifer Graser
(74) *Attorney, Agent, or Firm* — Womble Bond Dickinson (US) LLP

(57) ABSTRACT

The present invention is related to an immunogenic complex comprising a polymerized antigen, mannan and a dialdehyde, the composition comprising it and the use thereof as an immune response stimulator and vaccine, useful in the treatment of infectious diseases, neoplasms and allergies. Likewise, the invention relates to the method for obtaining said immunogenic complex, based on the antigen and mannan simultaneous polymerization and conjugation by using a dialdehyde.

22 Claims, 40 Drawing Sheets

(56) References Cited

OTHER PUBLICATIONS

Vinogradov, et al., "Structural analysis of the intact polysaccharide mannan from *Saccharomyces cerevisiae* yeast using 1H and 13C NMR spectroscopy at 750 MHz", Carbohydrate Research vol. 307, (1998), 177-183.

Woodward, et al., "Detection of Monoclonal Antibodies Specific for Carbohydrate Epitopes Using Periodate Oxidation", Journal of Immunological Methods, vol. 78, (1985), 143-153.

Zhang, et al., "D-mannose induces regulatory T cells and suppresses immunopathology", Nature Medicine, (Jul. 24, 2017), 1-12.

Zlotnik, et al., "*Saccharomyces cerevisiae* Mannoproteins Form an External Cell Wall Layer That Determines Wall Porosity", Journal of Bacteriology, vol. 159, No. 3, (Sep. 1984), 1018-1026.

Chinese Office Action dated Jul. 27, 2017, CN Application No. 201480030171.7.

Japanese Office Action dated Aug. 22, 2017, JP Application No. 2016-505868.

Yu, et al., "Sublingual Immunotherapy Efficacy of Dermatophagoides farinae Vaccine in a Murine Asthma Model", International Archives of Allergy and Immunology 2010, 152, 2009, 41-48.

IMMUNOGENIC COMPLEX FOR VACCINATION AND METHOD FOR THE PRODUCTION THEREOF

CROSS-REFERENCE TO RELATED APPLICATIONS

The present patent application is a national phase application of International Application No. PCT/ES2014/070263 filed Apr. 3, 2014, which claims priority to Spanish Application No. P201330474, filed Apr. 3, 2013, the disclosures of which are incorporated herein by reference.

FIELD OF THE INVENTION

The present invention relates to an immunogenic complex comprising a polymerized antigen, mannan and a dialdehyde, the composition comprising it, and the use thereof as an immune response stimulator and vaccine. Likewise, the invention relates to the method for obtaining said immunogenic complex, based on the antigen and mannan simultaneous polymerization and conjugation by using a dialdehyde. Therefore, the invention lies within the field of immunology and vaccine production, as well as in the field of treatment and prevention of allergies.

BACKGROUND

Dendritic cells (DC) are antigen-presenting cells specialized in efficiently stimulating T cells, and it is because of this that they are fundamental for inducing a specific immune response. Immature DCs are strategically distributed in tissues and organs where they act as sentinels, continuously taking antigen samples in their micro-environment. DCs start a maturation process as a response to different stimuli, including antigen themselves, microorganism products and tissue danger signals, which leads to migration towards T areas of secondary lymphatic organs, carrying the antigens loaded by them in the periphery. Here, mature DCs, showing an increase in the expression of HLA-II and co-stimulatory molecules, interact with T-cells presenting the antigenic peptides to them after these are processed, and stimulating them to initiate the specific response.

Immature DCs capture antigens by receptor-mediated endocytosis, micropinocytosis and phagocytosis. There are different receptors involved in endocytic uptake, among which mannose receptors are found (MR) (CD206 and CD209). They recognize terminal mannose residues, fucose and/or N-acetylglucosamine through carbohydrate recognising domains. Natural ligands include products of bacterial origin (glycoproteins and glycolipids), as well as mammal glycoproteins having high mannose content. MRs are expressed in macrophages and immature DCs, being involved in the endocytosis of mannosylated antigens for the processing and T-cell presentation thereof.

Immunotherapy in IgE antibodies-mediated allergic conditions is based on administration of therapeutic vaccines whose antigens are the same allergens as those the allergic patient is sensitised to. Allergens are proteins from pollens, dust mites, epithelium, etc, which are the superstructures carried in the air the patient breaths (environmental inhalants). It is widely accepted that the clinical efficacy of these vaccines is associated to the allergen dose delivered, so the WHO and consensus guidelines from scientific societies recommend that vaccines should be prepared with a sufficient allergen concentration. This requirement implies that the allergic patient response to the vaccine dose involves the risk of adverse effects which are intended to be limited. A way to avoid this is the preparation of vaccines based on modified allergens (allergoids) showing less capacity of reaction against IgE antibodies (less allergenicity).

Chemical modifications based on treating allergens with formaldehyde and/or glutaraldehyde, are the most widely used among vaccine manufacturers. Reaction of aldehyde groups (R—CHO) with amino groups (R—NH2) which are present in allergens amino acids, for example lysines, is the basis of such modification. Contrary to formaldehyde, which is a mono-aldehyde, the glutaraldehyde is a dialdehyde having two R—CHO groups capable of reacting with lysines R—NH2 present in different molecules. This causes an allergen polymerization and a loss in reactivity with specific IgE antibodies (the allergoid which is formed by means of formaldehyde is based on the structural modification of the protein, not on the polymerization thereof). This polymerization is considered to determine the allergoid lower allergenicity, since the IgE antibodies lose their accessibility to react with their epitopes (allergen binding sites), and reduce the number of mast cells sensitised with IgE which can be activated by them. Loss of allergenicity of polymerized allergens may imply a loss in immunogenicity, which would reduce the clinical efficacy of these preparations. It has been suggested that polymerization reduces the access of MR in DCs to the allergen mannose residues, and that this is decisive for polymerized allergens loss of immunogenicity. This is supported by the fact that the mannose residues are one of the main ligands used by DCs for allergens uptake, and that these cells play a critical role in allergen presentation to responding T cells.

Methods for the conjugation of sugars to proteins are mainly based in activating sugar by an oxidation process, generating reactive aldehyde groups (R—CHO) by conversion of the cis-glycol groups. The R—CHO generated in the oxidized sugar, after treatment with metaperiodate for example, may react with the $\epsilon$-amino groups of lysines, resulting in the formation of Schiff bases. This methodology is highly appropriate for conjugating glycoproteins (e.g., enzymes, antibodies), since their carbohydrate residue is used for conjugation and avoids the protein portion associated to the biological activity thereof.

Although sugar oxidation with periodate has also been reported as a way to mannosylate proteins (Masarova et al. 2002. Int. J. Polymer. Anal. Charact., 7: 106-116), including allergens (Weinberger et al. 2013. J Control Release, 165: 101-109), its use to mannosylate polymerized antigens has two major drawbacks:

a) The oxidation of sugars produces the rupture of bonds between adjacent carbon atoms which contain hydroxyl groups (OH) and which are the basis for reactive aldehydes generation. Said rupture affects the mannose structure (Shibuya, N., et al. 1988. J. Biol. Chem., 263: 728-734), altering its capacity of binding to mannose-recognising lectins (Masarova et al. 2001, Chem. Pap. 55: 130-135) and its DC activation capacity (Sheng et al, 2006. Immunology, 118:372-383). Although the loss of mannose structural integrity may be minimized by reducing the degree of oxidation (Masarova et al. 2001, Chem. Pap. 55: 130-135), its efficiency for conjugation under milder conditions is subjected to the nature of the protein to be mannosylated (Weinberger et al. 2013, J. Control Release, 165: 101-109). In order to preserve mannose in the native form thereof, there have been attempts to perform mannosylation of proteins by means of glycosylation reactions at high temperature, but with a negative result in the absence of oxidation (Kanska et al. 2008. Biotechnol. Appl. Biochem. 49: 57-64).

b) Mannose activated after its oxidation generates reactive aldehydes which must interact with the free amino groups of the protein to be mannosylated. However, polymerization of proteins with glutaraldehyde produces a dramatic reduction of these amino groups, since they have already been used in their reaction with glutaraldehyde itself. Under these conditions, the efficiency of mannose activated to mannosylate proteins previously treated with glutaraldehyde is likely to be very low, as it is glutaraldehyde capacity to polymerize when lacking the amino groups to which it may bind. (Silva et al. 2004. Food Technol. Biotechnol. 42: 51-56). This inconvenient does not only affect mannosylation of polymerized allergens, but also that of any protein polymerized with gutaraldehyde which might eventually be intended to be mannosylated.

Patterson et al. 1977 (J Allergy Clinical Immunology 59: 314-319) describe allergen polymerization (gramineae pollen) with glutaraldehyde. The polymerized allergens are hypoallergenic since they show reduced capacity of activation of mastocytes sensitised with IgE antibodies.

Subiza et al. 2008 (Clinical and Experimental Allergy, 39: 987-994) describe the use of allergens (gramineae pollen, *Trisetum paniceum* and *Dactylis glomerata*) modified with glutaralehyde (also referred to as allergoids) for immunotherapy in allergy. Researchers report that vaccination with allergoids from gramineae obtained by polymerization with glutaraldehyde is effective.

Heydenreich et al. 2012 (Immunology, 136: 208-217) describe a comparative study of differences in immunogenicity and allergenicity between allergen extracts from intact pollen from *Phleum pratense* and *Betula verrucosa* species, and their corresponding allergoids modified with glutaraldehyde or formaldehyde. It is reported that modification with glutaraldehyde reduces allergenicity and immunogenicity of allergoids more than modification with formaldehyde, and that DCs do not capture this type of modified allergens efficiently.

Weinberger et al. 2013 (Journal of Control Release, 165: 101-109) describe conjugation of allergenic proteins (ovalbumin and papain) to mannose activating the sugar by mild oxidation with periodate. A different degree of efficiency is obtained depending on the protein to be mannosylated. The mannosylated conjugates are reported to be captured by DCs in vivo and to produce an immune response in mice, so they could be useful for immunotherapy.

Therefore, in the state of the art there is a need to provide a method for obtaining vaccines based on polymerized and mannosylated antigens which is alternative to those currently used in the state of the art, and which allows antigen polymerization as well as its conjugation to mannose in a highly effective way, without the sugar losing its structural integrity and without the polymer properties (lower allergenicity) being affected, so that the vaccine, based on polymerized and mannosylated proteins, increase the immunogenicity thereof by improving their uptake by DCs.

SUMMARY

The authors of the present invention have found that addition of a dialdehyde to a mixture of an antigen of a protein nature and mannan, allows antigen polymerization simultaneously with the antigen conjugation to mannan, which makes it possible to obtain an immunogenic complex o vaccine capable of stimulating or inducing an immune response in the individual without triggering an allergic response to that complex, and capable of being recognised and captured by dendritic cells (DC).

Based on this finding, there have been developed a series of inventive aspects which are described in detail below.

Immunologic Complex of the Invention

As it has been previously mentioned, addition of a dialdehyde, in particular glutaraldehyde, to a mixture of a protein (antigen) and mannan, allows antigen polymerization simultaneously with antigen conjugation to mannan, which makes it possible to obtain an immunogenic complex or vaccine.

Thus, in one aspect the present invention relates to an immunogenic complex, hereinafter "immunogenic complex of the invention", comprising a polymerized antigen, mannan and a dialdehyde.

In the present invention, "immunogenic complex" is understood to be the association of two or more units which remain conjugated to each other by a chemical bond (chemical conjugation), or by physical entrapment (physical conjugation), being said units a polymerized antigen, mannan and a dialdehyde.

By "polymerized antigen" is meant the polymer formed by antigen monomers bound to each other, which can be different or the same. Therefore, in a particular embodiment, the polymerized antigen comprises at least two antigens which are the same or different to each other. By "antigen" is meant any substance capable of inducing an immune response, both humoral and cellular, in the organism of a subject (human or animal), or capable of inducing a cellular immune response, (immune cells expansion, activation and/ or maturation, cytokine, or antibody production) when it contacts immune cells. In particular, an antigen is a protein that can be an allergen, a protein derived from an infectious agent, or neoplastic cell, a peptide or fragment of said proteins, a recombinant protein from said proteins or even a synthetic peptide capable of inducing the indicated responses. In a particular embodiment, the antigen is an allergen.

By "allergen" is meant that substance which is capable of causing allergy in an individual, that is, that substance which is recognised as foreign by the immune system of an individual, causing an immune reaction, mainly, the production of type E immunoglobulins (IgE). Examples of allergens include, but are not limited to, pollen allergenic extracts, allergenic extracts from arthropods, allergenic extracts from food or food products, components present in the saliva, claws or stings from insects inducing a sensitivity reaction in a subject, etc. Thus, for example, pollen protein extracts, such as gramineae pollen (*Lolium perenne, Poa pratense, Phleum pratense, Cynodon dactylon, Festuca pratensis, Dactylis glomerata, Secale cereale, Hordeum vulgare, Avena sativa, Triticum sativa*), other grass pollen (such as *Artemisia vulgaris, Chenopodium album, Plantago lanceolata, Taraxacum vulgare, Parietaria judaica, Salsola kali, Urtica dioica*), or tree pollen (such as *Olea europaea, Platanus* spp, *Cuppresus* spp), etc., can be used. Protein extracts from arthropods, such as dust mites (such as *Dermatophagoides pteronyssinus, Dermatophagoides farinae, Acaro siro, Blomia tropicalis, Euroglyphus maynei, Glyciphagus domesticus, Lepidoglyphus destructor, Tyrophagus putrescentiae*), etc, can also be used. Other allergenic extracts can be obtained from fungal spores (*Alternaria alternata, Cladosporium herbarum, Penicilium notatum*)

and animal epithelium (dog epithelium, cat epithelium, horse epithelium, feather mixture) as well as from food components, etc. As it is understood by an expert in the art, the skin and cutaneous annexes such as hair are included within the term "epithelium". Practically any allergen can be used in the immunogenic complex; nevertheless, in a particular embodiment, the allergen is selected from the group consisting of pollens, mites, epithelia, fungal spores and combinations thereof.

In another particular embodiment, the pollen derives from the species *Phleum pratense, Dactylis glomerata, Cynodon dactylon, Lolium perenne, Trisetum* spp., *Olea europaea, Cuppresus* spp., *Ambrosia* spp., *Betula* spp., *Platanus* spp., *Corylus avellana* or *Alnus glutinosa*.

In another particular embodiment, the mite belongs to species *Dermatophagoides pteronyssinus, Dermatophagoides farinae* or *Blomia tropicalis*.

In another particular embodiment, the epithelium belongs to the species *Felis domesticus* or *Canis familiaris*.

In another particular embodiment, the fungal spore belongs to the species *Alternaria alternata* or *Alternaria tenuis*.

In the present invention, by "mannan" is meant a carbohydrate polymer consisting of mannose and glycosidic bonds of the following types: alpha-1,6-glycoside, alpha-1,2-glycoside, alpha-1,3-glycoside or beta-1,3-glycoside. By mannose is meant the simple sugar or monosaccharide formed by 6 carbon atoms and whose functional chemical group is an aldehyde in carbon 1 or anomeric carbon. Mannan may content a peptide residue from the mannoprotein to which it naturally binds. Any mannan can be used in the context of the present invention. Examples of mannan include, but are not limited to, polymannose, galactomannan, glucomannan, acemannan and aloerides.

Polymannose is understood to be a linear structure formed by mannoses bound by α-D-(1→6) bonds, having frequent short branches of different units, mainly by α-D-(1→2) bonds, but also α-D-(1→3).

"Galactomannan" is understood to be the compound formed by a mannose chain bound to each other by β(1→4), bonds in most cases having branches formed by galactose units bound to the mannoses by an α(1→6) bond. Depending on the plant from which they are extracted, galactomannans have different branching degrees.

"Glucomannan" should be understood as the compound whose chemical structure includes D-mannose and D-glucose in a proportion 8:5, respectively, linked by β(1→4) bond. It is found, for example, in tubers from the plant *Amorphophallus konjac*.

"Acemannan" should be understood as the mixture of O-acetylated complex polysaccharides of the type beta(1-4)-mannan. Acemannan is found, for example, in the plant *Aloe vera*.

"Aloeride" is understood to be that polysaccharide with high molecular weight constituted by glucose, galactose, mannose and arabinose. The aloeride is found, for example, in the plant *Aloe vera*.

Mannans (polymannoses, galactomannans, glucomannans, etc.) may be obtained from natural sources, for example, from fungi, yeasts and plants, or by chemical synthesis using techniques broadly known for an expert in the art. In a particular embodiment, the mannan which is part of the immunogenic complex of the invention comes from yeast, a plant or a fungus. In another particular embodiment, the yeast is selected from the group consisting of *Saccharomyces* ssp., *Pichia* ssp., and *Candida* ssp.

Examples of *Saccharomyces* ssp. Yeasts include, but are not limited to, *S. bayanus, S. boulardii, S. bulderi, S. cariocanus, S. cariocus, S. cerevisiae, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum* and *S. zonatus*. In a more particular embodiment, the yeast is *S. cerevisiae*.

Examples of *Pichia* ssp. Yeasts include, but are not limited to, *P. pastoris, P. anomola, P. heedii, P. guilliermondii, P. kluyveri, P. membranifaciens, P. norvegensis, P. ohmeri, P. pastoris* and *P. subpelliculosa*.

Examples of *Candida* ssp. Yeasts include, but are not limited to, *C. albicans, C. ascalaphidarum, C. amphixiae, C. Antarctica, C. argêntea, C. atlântica, C. atmosphaerica, C. blattae, C. carpophila, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermédia, C. jeffresii, C. kefyr, C. krusei, C. lusitaniae, C. lyxosophila, C. maltosa, C. marina, C. membranifaciens, C. milleri, C. oleophila, C. oregonensis, C. parapsilosis, C. quercitrusa, C. rugosa, C. sake, C. shehatea, C. temnochilae, C. tenuis, C. tropicalis, C. tsuchiyae, C. sinolaborantium, C. sojae, C. subhashii, C. viswanathii, C. utilis*.

Examples of plants from which mannan can be extracted include but are not limited to, leguminosae (for example, *Ceratonia siliqua, Cyanaposis tetragonolobus*, etc.), tubers (for example, *Amorphophallus konjac*, etc.), seeds of plants from the family Liliaceae, Iridaceae, in which mannan is used as energy storage and plant cell walls of green algae, such as *Acetabularia, Codium, Halicoryne*, etc., and red algae (*Porphyra umbilicalis*).

Examples of fungi from which mannan can be extracted include, but are not limited to, *Paecilomyces* ssp. and *Ganoderma lucidum* (reishi).

As understood by the person skilled in the art, if mannan is obtained from a fungus or yeast, it will be part of the fungi and yeasts cell wall, and thereby it may contain residues of the protein used by the organism to synthesize the cell wall. Thus, mannan may comprise in its structure amino groups from the amino acids residues which are present. Therefore, in another more particular embodiment, said amino groups come from the lysine amino acid.

In the present invention, "dialdehyde" is understood to refer to the compound which comprises two aldehyde groups. Examples of dialdehyde include, but are not limited to, glutaraldehyde, glyoxal, malonaldehyde, succinaldehyde and adipaldehyde. In a preferred embodiment, the dialdehyde is glutaraldehyde.

As stated above, the immunogenic complex of the invention comprises a polymerized antigen, mannan and a dialdehyde. Thus, the binding of the components of the immunogenic complex of the invention can be generated by chemical conjugation, physical conjugation or both at the same time.

In the present invention, "chemical conjugation" is understood as the binding of the components of the immunogenic complex of the invention by means of a chemical bond. As explained above, mannan may comprise amino groups due to the presence of amino acids in the structure thereof, for example lysines. Without wishing to be bound by theory, it is thought that binding between the components of the immunogenic complex may be generated by the bond between the amino groups which are present in the mannan and the dialdehyde present in the reaction. Thus, in a particular embodiment, the polymerized antigen is bound to mannan by the dialdehyde. The dialdehyde in aqueous medium is present in a certain proportion in a polymeric form, there being, therefore, several species with 2 or more aldehyde functional groups whose reaction with the amino groups present in mannan and in the antigenic protein leads to covalent crosslinking among the several components present in the reaction mixture. Primary reaction between aldehyde and amino groups leads to formation of the so called Schiff bases that, depending on the pH conditions, may be reversible. However, in the case the aldehyde groups belong to dialdehydic or polyaldehydic compounds, as for example glutaraldehyde, and the polymeric forms thereof present in the aqueous solution, there take place other reactions of the type aldol condensation and dehydratation which generate alpha-beta unsaturated carbonylic systems of multifunctional polymeric nature. Additionally, it has been shown that Schiff bases are also likely to produce aldol-like condensations with the aldehydes present in the reaction medium, so as to generate alpha-beta unsaturated imines more stable than the original Schiff bases. On the other hand, both carbonyls and alpha-beta unsaturated imines derived from aldol condensations are likely to undergo a conjugate addition reaction by the amino groups so as to form new stable covalent bonds. The chemical reactivity described together with the multifunctional nature of the original dialdehyde and the polymeric forms thereof present in the reaction medium, is the basis for chemical covalent and stable crosslinking between mannan and the antigens to form the final polymeric chemical conjugates.

In the present invention, "physical conjugation" is understood to be the binding of the components of the immunogenic complex of the invention by physical entrapment. Without wishing to be bound by theory, it is thought that when the antigen is being polymerized, mannan stays trapped in the polymer weave favoured by the rigidity and the high level of branching of its structure. Thus, in a particular embodiment, the allergen is bound to mannan by physical entrapment by the polymer.

Once the immunogenic complex is formed, the proportion of the components may vary depending on the mannan concentration in the medium. Thus, in a particular embodiment the ratio antigen:mannan ranges between 1:10 and 1:0.1, preferably, between 1:4 and 1:0.15, more preferably, between 1:3 and 1:0.3, more preferably, between 1:4 and 1:0.5. In a particular embodiment, the antigen:mannan ratio is 1:0.3 or 1:0.5.

Method of the Invention

The authors of the present invention have found that addition of a dialdehyde to a mixture of antigen and mannan allows antigen polymerization simultaneously to antigen conjugation to mannan, which makes it possible to obtain an immunogenic complex or vaccine capable of stimulating and/or inducing an immune response in the individual without triggering an allergic response to said complex, and which can be recognised and captured by the dendritic cells (DC).

Therefore, in another aspect, the present invention relates to a method for obtaining the immunogenic complex of the invention, hereinafter "method of the invention", which comprises (i) preparing a dissolution comprising an antigen and mannan, and (ii) adding a dialdehyde to said dissolution.

In the first step [step (i)], the method of the invention consists of preparing a dissolution comprising an antigen and mannan.

The term antigen has been defined previously. In a particular embodiment, the antigen is an allergen. Examples of allergens include, but are not limited to, pollen allergenic extracts, allergenic extracts from arthropods, allergenic extracts from food or food products, components present in the saliva, claws or stings from insects inducing a sensitivity reaction in a subject, etc. In a particular embodiment, the allergen is selected from the group consisting of pollens, preferably, *Phleum pratense, Dactylis glomerata, Cynodon dactylon, Lolium perenne, Trisetum* spp., *Olea europaea, Cuppresus* spp., *Ambrosia* spp., *Betula* spp., *Platanus* spp., *Corylus avellana* or *Alnus glutinosa*; mites, preferably, the mite belongs to the species *Dermatophagoides pteronyssinus, Dermatophagoides farinae* or *Blomia tropicalis*; epithelia, preferably the epithelium belongs to the species *Felis domesticus* or *Canis familiaris*; fungi spores, preferably the fungus spore belongs to the species *Alternaria alternata* or *Alternaria tenuis*; and the combinations thereof.

As it is understood by the person skilled in the art, the dissolution of step (i) may contain more than one antigen which can be different or the same to each other. Therefore, in a particular embodiment, the dissolution comprises at least two antigens which are the same or different to each other.

Techniques and methodologies used to obtain antigen and allergenic extracts are broadly known by the person skilled in the art, although these can be commercially available or found in the form of recombinant proteins. In the case the antigen or the allergenic extract is lyophilised, this will have to be reconstituted, for example, with phosphate buffer, so that it can be used in the method of the invention.

On the other hand, the dissolution of step (i) has also mannan. The term mannan has been previously defined and it can be applied to the present inventive aspect. Examples of mannans include, but are not limited to, polymannose, galactomannan and glucomannan. In a particular embodiment of the method of the invention, the mannan used in the method of the invention comes from yeast, a plant or a fungus. In another more particular embodiment, the yeast is selected from the group consisting of *Saccharomyces* ssp., particularly *S. cerevisiae; Pichia* ssp., and *Candida* ssp. Examples of yeasts, fungi and plants from which mannan can be obtained have been previously described in the present disclosure. Furthermore, as it has been stated above, mannan can comprise in its structure amino groups from amino acids residues present in the mannoprotein. Therefore, in another even more particular embodiment, mannan comprises amino groups, said amino groups which, in another more particular embodiment, come the from lysine amino acid.

The amount of mannan to be added to the dissolution may vary depending on the antigen:mannan ratio which is intended to be obtained in the immunogenic complex of the invention. Thus, in a particular embodiment, the antigen:mannan ratio ranges from 1:10 to 1:0.1, preferably, between 1:4 and 1:0.15, more preferably, between 1:3 and 1:0.3, more preferably, between 1:4 and 1:0.5. In a particular embodiment, the antigen:mannan ratio is 1:0.3 or 1:0.5.

Once the antigen and mannan dissolution is prepared, the dialdehyde is added acting then as a polymerizing agent [step (ii) of the method of the invention]. The dialdehyde will be gradually added to the dissolution until reaching a concentration which is enough to achieve antigen polymerization, as well as the mannan conjugation to antigen. The technique and methodology used to prepare polymers using dialdehydes is well known in the state of the art and is common practice for experts in the art (Silva et al. 2004.

Chemical Modifications on Proteins Using Glutaraldehyde. Food Technol. Biotechnol. 42: 51-56).

After addition of dialdehyde to the antigen and mannan dissolution, the mixture is left under the appropriate conditions and during the adequate time for the polymerization reaction to take place, for example, about 15 hours at 4° C. under stirring.

In a particular embodiment, the dialdehyde is selected from the group consisting of glutaraldehyde, glyoxal, malonaldehyde, succinaldehyde and adipaldehyde. Preferably, the dialdehyde is glutaraldehyde.

Upon completion of the required time for the polymerization reaction to take place, the reaction is stopped by adding to the mixture an agent that neutralizes (neutralizing agent) the free aldehyde groups, such as agents containing amino groups (for example, amino acids, ε-amino-n-caproic acid, etc.), or other reactive agents with aldehydes (for example, sodium metabisulfite, ammonium, etc.), excluding oxidizing agents (for example, hydrogen peroxide, sodium periodate, etc.) due to their effect on mannose. In a particular embodiment of the method of the invention, the method has an additional step (iii) comprising the addition of a neutralizing agent, for example, an amino acid, in particular, glycine, to stop the polymerization reaction. The amount of glycine added to the reaction mixture to stop polymerization may vary depending on reaction conditions, but calculating the amount of glycine which is necessary to add to stop polymerization is common practice for the expert in the art. In general, glycine has to be in excess with respect to the added amount of aldehyde, for example, in a dialdehyde: glycine ratio of 1:50.

After stopping the polymerization reaction, the immunogenic complex can be isolated, which is common practice for a person skilled in the art. Thus, in a particular embodiment, the method of the invention comprises a step (iv) of isolating the immunogenic complex. Practically any method of isolating protein complexes may be used in the context of the present invention. Examples of said methods include, but are not limited to, low or high pressure liquid chromatography column, affinity chromatography based on mannose-binding lectin (for example, Concanavalin A), precipitation techniques (for example, ammonium sulphate), density gradient separation and differential centrifugation. By way of example, the mixture containing the immunogenic complex of the invention already formed may be dialyzed in order to eliminate the salts and the possible non polymerized residues, after which filtration of the polymerized mixture is carried out, for example by tangential ultrafiltration with a membrane having a pore size of 100 KDa.

Uses of the Immunogenic Complex of the Invention

The immunogenic complex of the invention has certain technical characteristics that make it able to stimulate and/or induce an immune response in the individual with a low allergic response to said complex in case of being allergens. This property makes it possible to use the immunogenic complex of the invention to elaborate a pharmaceutical composition that, when administered to a subject stimulates and/or induces the immune response of said subject, and which makes it appropriate to be used as a vaccine in the treatment, for example, of allergies, infectious diseases or neoplasias.

Therefore, in one aspect, the invention relates to the use of the immunogenic complex of the invention in the elaboration of a pharmaceutical composition.

Thus, in another aspect, the invention relates to a pharmaceutical composition, hereinafter "pharmaceutical composition of the invention", comprising the immunogenic complex of the invention and a pharmaceutically acceptable carrier. Examples of pharmaceutically acceptable carriers are known in the state of the art and include phosphate buffered saline solutions, water, emulsions such as oil/water, different types of wetting agents, sterile dissolutions, etc. Compositions comprising said carriers can be formulated by conventional procedures known in the state of the art. All particular embodiments explained for the immunogenic complex of the invention, can be applied to the present inventive aspect. Additionally, the pharmaceutical composition of the invention may also have a pharmaceutically acceptable excipient, diluent, adjuvant (for example, aluminium hydroxide, calcium phosphate, monophosphoryl lipid A, chitosan and others) and/or stabiliser (for example, glycerol). As it should be understood by the expert in the art, the immunogenic complex of the invention will be present in the composition of the invention in a therapeutically effective amount, that is, in such an amount that it is enough to exert the effect of stimulating and/or inducing the immune response in a subject.

The term pharmaceutical composition includes compositions for their use in human or animal healthcare (veterinary compositions).

In a particular embodiment, the pharmaceutical composition of the invention also comprises an additional substance. Practically any substance potentially useful for the symptomatic treatment of a disease or allergy can be incorporated as an additional active substance. Illustrative, not limiting examples of said additional active substance include antihistaminics, steroid hormones, disodium cromoglycate, fluticasone, rupatadine, ebastine, loratadine, desloratadine and other antagonists of histamine receptors, leukotrienes, etc., and the mixtures thereof.

The pharmaceutical composition of the invention can be administered by any appropriate route (for example, oral, sublingual, perioral, intranasal, parenteral, transdermal, topical administration routes, etc.), for which the pharmaceutically acceptable excipients and carriers required for the formulation of the chosen way of administration, will be used. The different pharmaceutical ways of administering and preparing drugs are common knowledge for the person skilled in the art. In an illustrative, but not limitative way, the pharmaceutical composition of the invention may be part of a formulation in the form of macroparticles, nanoparticles or liposomes, and it can be administered in a solid pharmaceutical form of administration, in a liquid pharmaceutical form of administration, or in a pharmaceutical form of administration comprising a disperse system. More particularly, the pharmaceutical composition of the invention may be in the form of a solution for injection, pharmaceutical forms suitable for sublingual delivery, powder, pellets, beads, tablets, capsules, syrups, emulsions, suppositories, eye drops, atomizations, aerosols, creams, gels, etc. The dosage regime of the composition of the invention will be determined according to the physician and the clinical factors. As it is well known in medicine, dosage depends on many factors including the physical characteristics of the patient (age, height, sex), the delivery procedure used, the severity of the disease, the particular compound used and the pharmacokinetic properties of the individual.

In a particular embodiment, said pharmaceutical composition is useful for stimulating and/or inducing the immune response. In another particular embodiment, said pharmaceutical composition is useful as a vaccine. In another particular embodiment, said pharmaceutical composition is useful in the treatment of allergy, infectious diseases and neoplasias in a subject.

In the present invention, "allergy" is understood to be the hypersensitivity to a particle or substance (called "allergen") that, if inhaled, ingested or touched, produces a characteristic clinical picture and triggers an immune response, mainly an IgE response, in the subject. The term "allergen" has already been described above in the present disclosure.

In the present invention "infectious disease" refers to the clinical manifestation consistent with an infection caused by a microorganism—such as bacteriae, fungi, viruses, protozoa, etc., —or by prions. Examples of infectious diseases include, but are not limited to, brucellosis (*Brucella* spp.), anthrax (*Bacillus anthracis*), cholera (*Vibrio cholerae*), diphtheria (*Corynebacterium diphtheriae*), erysipelas (*Streptococcus* spp.), Q fever (Coxiella burneti), typhoid fever (*Salmonella typhi, S. paratyphi*), Legionnaires' disease (*Legionella pneumophila*), pneumonia (*Streptococcus pneumoniae, Staphylococcus aureus, Klebsiella pneumoniae, Mycoplasma* spp., *Chlamydia* spp.), tuberculosis (*Mycobacterium tuberculosis*) and tetanus (*Clostridium tetani*). Examples of viral infectious diseases include, but are not limited to, dengue fever (*Flavivirus*), yellow fever (*Flavivirus*), Ebola haemorrhagic fever (*Filovirus*), influenza (*Influenzavirus*), hepatitis A (*Enterovirus* (VHA)), hepatitis B (*Orthohepadnavirus* (VHB)), hepatitis C (*Hepacivirus* (VHC)), herpes (*Herpesvirus*), mononucleosis (Epstein-Barr virus), parotitis (*Paramixovirus*), swine fever (*Pestivirus*), poliomyelitis (*Enterovirus*), common cold (*Rinovirus, Coronavirus, Ecovirus, Coxsackievirus*), rabies (*Rhabdovirus*), rubella (*Rubivirus*), measles (*Morbillivirus*), varicella (*Varicela-zoster*) and variola (*Orthopoxvirus*). Examples of fungal infections include, but are not limited to, aspergillosis, candidiasis, chromomycosis, cryptococcosis, dermatophytosis, sporotrichosis, histoplasmosis, herpes circinatus, otomycosis, pityriasis versicolor, keratomycosis and zygomycosis. Examples of diseases caused by protozoa include, but are not limited to, leishmaniasis, malaria, cryptosporidiosis, toxoplasmosis, amoebiasis, giardiasis and Chagas disease. Examples of infectious diseases caused by prions include, but are not limited to, Creutzfeldt-Jakob disease, bovine spongiform encephalopathy ("mad cow disease"), scrapie (or trembling disease), fatal familial insomnia (FFI) and kuru.

In the present invention "neoplasia" is understood to be the disease caused by an alteration of cell proliferation and, many times, of cell differentiation which consists of the formation of a mass or tumour that, in case of being malignant, is referred to as cancer. Examples of benignant neoplasias include, but are not limited to, fibroma (fibrous connective tissue), myxoma (loose connective tissue), lipoma (adipose tissue), chondroma (cartilage tissue), osteoma (bone tissue), hemangioma (blood vessels), lymphangioma (lymphatic vessels), meningioma (meninges), glomus tumor (supporting neural tissue), leiomyoma (smooth muscle tissue), rhabdomyoma (striated muscle tissue), papilloma (epithelial tissue forming papillae), adenoma (glandular tissue) and teratoma (totipotent cells). Examples of malignant neoplasms include, but are not limited to, sarcomas (for example: fibrosarcoma, myxosarcoma, liposarcoma, chondrosarcoma, osteosarcoma, angiosarcoma, lymphangiosarcoma, synovial sarcoma, leiomyosarcoma, rhabdomyosarcoma, etc.), carcinomas (for example: epidermoid or squamous carcinoma, basal cell carcinoma, adenocarcinoma, cystadenocarcinoma, choriocarcinoma, penile carcinoma, lung carcinoma, breast carcinoma, colon carcinoma, etc.), gliomas, lymphomas, leukaemias, melanoma, hepatoma, seminoma, chordoma and mesothelioma. On the other hand, examples of cancer include, but are not limited to, lung cancer, breast cancer, colon and rectum cancer, pancreatic cancer, ovarian cancer, leukaemia, prostate cancer and liver and bladder cancer.

In the present invention, individual or subject refers to a member of an animal species, preferably a mammal, and including, but not being limited to, pets, primates and humans; in the context of the present invention, the individual is preferably a male or female human of any race or age.

By "vaccine" is meant the antigen preparation that, once inside the organism, causes the activation of specific lymphocytes and antigen production, and thereby a defence response against foreign substances or pathogenic microorganisms. This response may generate immunological memory, producing temporary or long term immunity against the corresponding pathogen attack.

Thus, the present invention allows the customization of vaccines for a subject, that is, the antigen can be chosen according to the requirements of the subject, in order to produce the immunogenic complex of the invention, which can be used as a vaccine. The disease to be treated/prevented will depend on the antigen selected for manufacturing the immunogenic complex of the invention. Thus, any allergy, infectious or antineoplastic disease may be treated with the immunogenic complex of the invention. For example, knowing the allergen to which the subject is allergic to, an immunogenic complex comprising the selected allergen/s can be prepared according to the present invention, and it can be administered to the subject to generate an immune response, thus treating the allergy.

Therefore, in another aspect, the invention relates to a vaccine comprising an immunogenic complex of the invention.

Treatment Method of the Invention

In another aspect, the invention relates to a method for preventing and/or treating an infectious disease, a neoplasm or an allergic reaction caused by an allergen in a subject, wherein said method comprises administering the immunogenic complex of the invention or the pharmaceutical composition of the invention to the subject.

Throughout the description and the claims, the term "comprise" and its variants does not exclude other technical characteristics, additives, components or steps. For experts in the field, other purposes, advantages and characteristics of the invention will derive in part from the description and in part from the practice of the invention. The following examples and figures are provided for illustration purposes, and are not intended to be limitative of the present invention.

BRIEF DESCRIPTION OF THE FIGURES

FIG. 19.

FIG. 20.

FIG. 24. FIG. 24B is a graphic representation showing the results obtained on the uptake of dendritic cells (DC) derived from human monocytes with allergens from unpolymerized (native) *Phleum pratense*, polymerized (Polymer) or polymerized with mannan (Pol Mannan), being labelled at cysteines with Alexa 488. The assays were carried out at two incubation times (1 and 5 min) and analysed by flow cytometry. The top section shows the double positive cells (upper right quadrant) wherein the DCs (HLADR+) which capture Alexa 488 are concentrated. The lower side shows the average fluorescence intensity of the DCs according to the preparation they have been incubated with.

EXAMPLES

Figure 1:
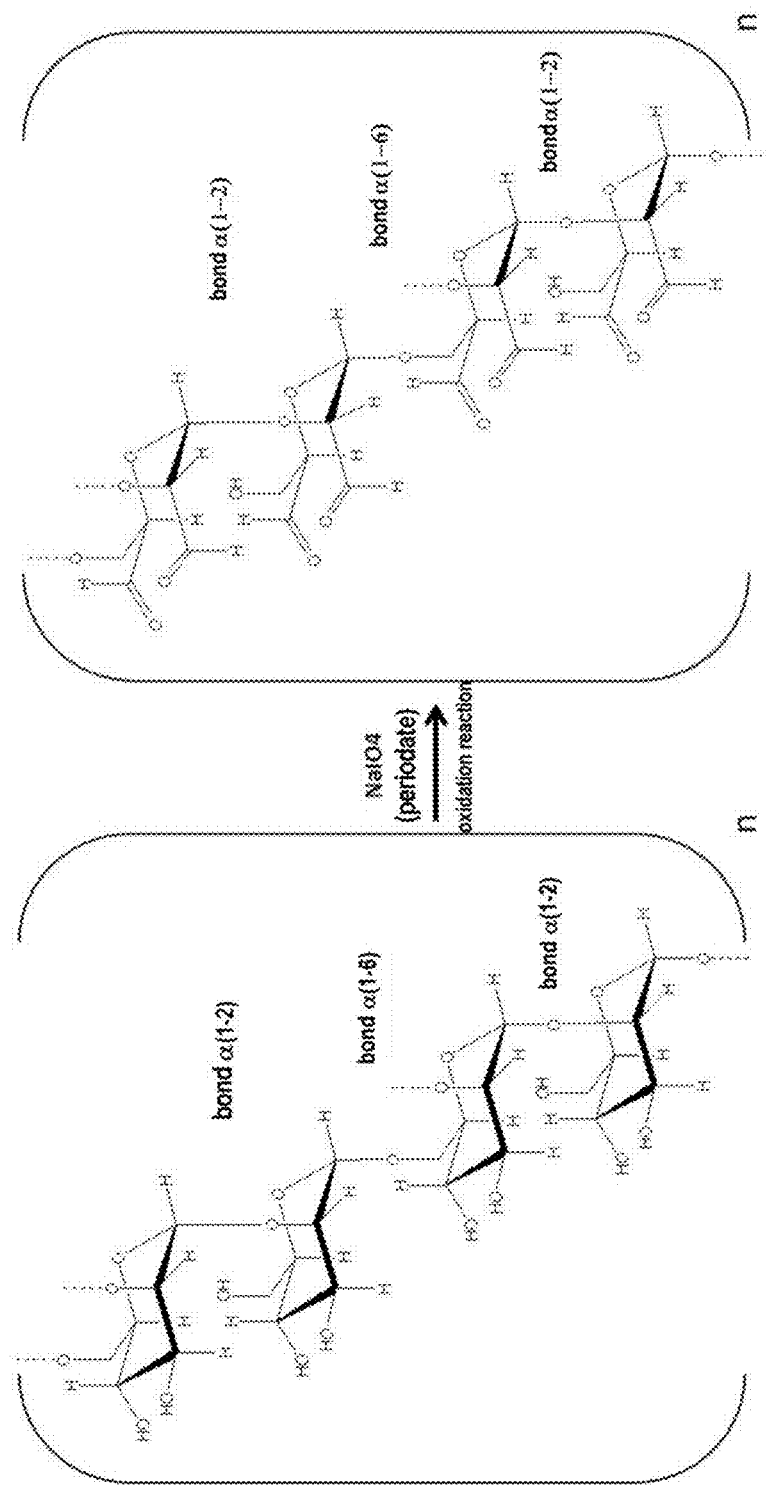
FIG. 1. It is a graphic representation of the oxidation reaction of mannan with periodate. The scheme shows the two types of glycosidic bonds, alpha(1-2) and alpha(1-6) in the mannan derived from yeast. Oxidation with periodate deteriorates the pyranose rings in both cases.
Figure 2:
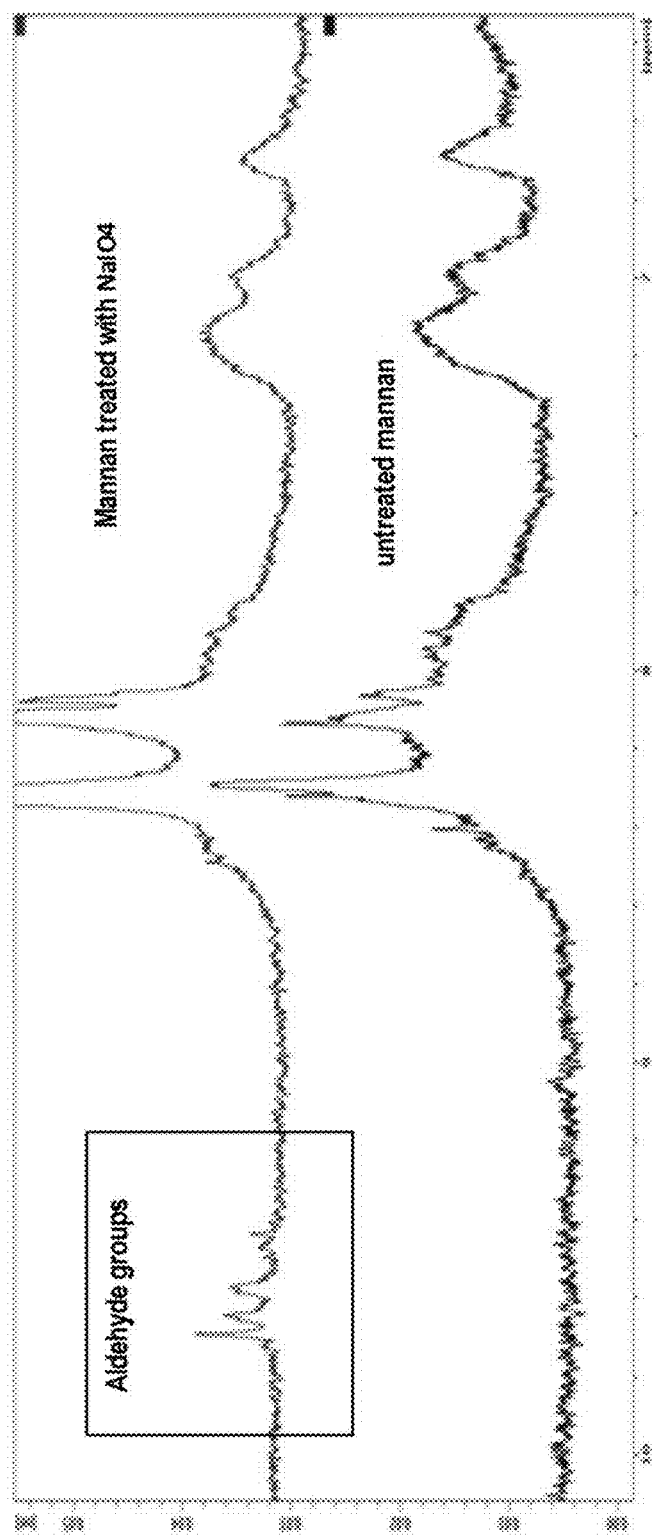
FIG. 2. It is a graphic representation of the one-dimensional spectrum of mannan pre-treated with periodate and without being treated. There appear aldehyde groups in the pre-treated mannan.

Example 1: Vaccine Production by Conjugation of Allergens (Polymerized or Not) with Oxidised Mannan 1.—Mannan Oxidation The mannan from *Saccharomyces cerevisiae* was previously fractionated by ultrafiltration using a 100 KDa cut-off membrane. The low molecular weight filtrated fraction was collected and subjected to oxidation with periodate. FIG. 1 shows the theoretical action of periodate over mannose integrity and the generation of aldehyde groups. In FIG. 2 the generation of these groups after mannan oxidation is experimentally demonstrated.

2.—Allergen Polymerization

Figure 3:
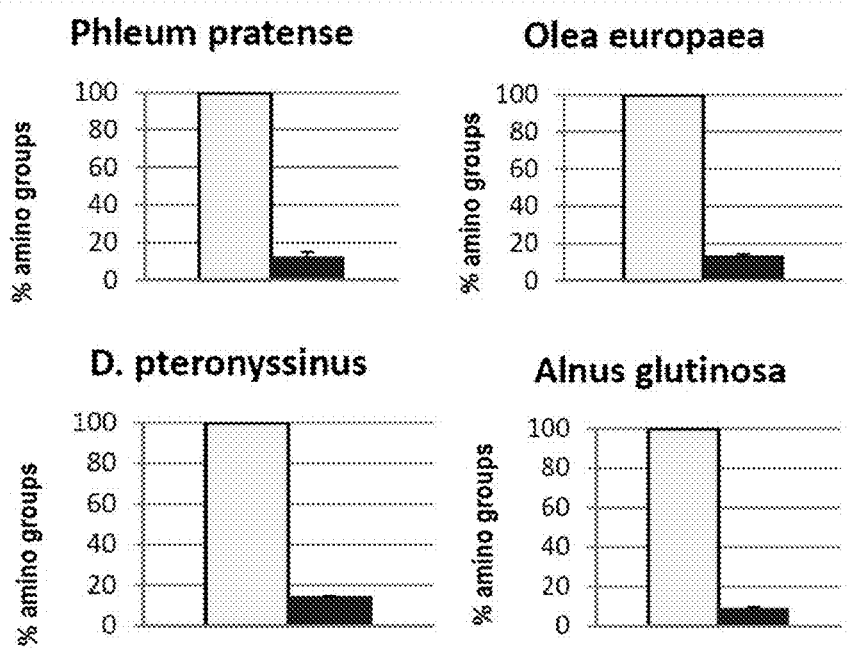
FIG. 3. It shows four charts representing percentages of the free amino groups in several polymerized allergens (black bars) out of the allergen value in its native unpolymerized form (white bars). The data shown are the mean of at least 4 different batches.

Allergens from different origins (*Phleum pratense, Olea europea, Dermatophagoides pteronyssinus* and *Alnus glutinosa*) were polymerized using glutaraldehyde. FIG. 3 shows the reduction of amino groups in the allergens polymerized over the value of the allergen in its native unpolymerized form. The presence of amino groups was determined by reaction with ninhydrin according to European Pharmacopoeia (section 2.2.56, amino acids analysis).

3.—Mannan Conjugation Oxidised with BSA (Bovine Serum Albumin)

Figure 4:
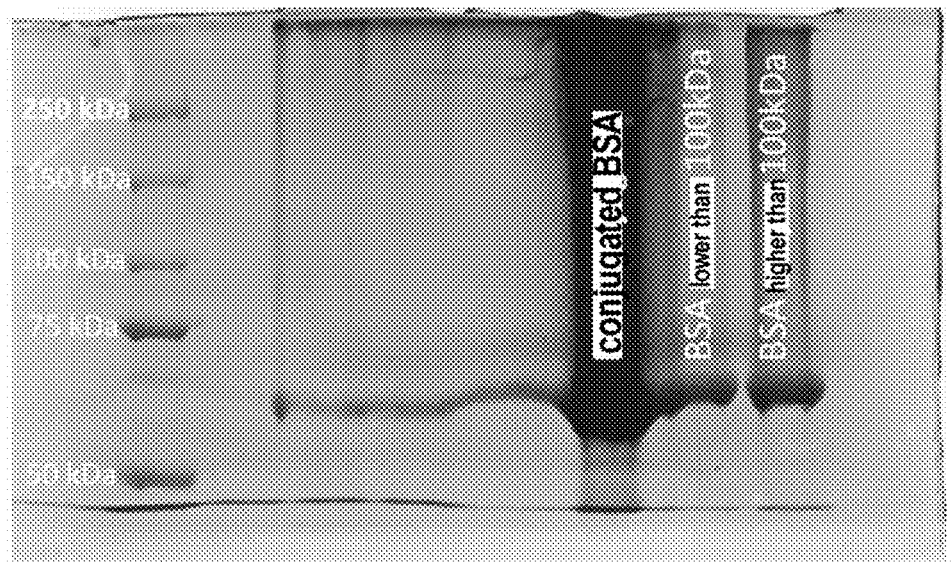
FIG. 4. It is an image showing the result of an electrophoresis (PAGE) under denaturalizing conditions, after treating bovine serum albumin (BSA) with previously oxidised mannan. The lanes correspond to the crude mixture after conjugation (conjugated BSA) and the two samples which are from filtration in AMICON YM100 (BSA less than 100 kDa and BSA greater than 100 kDa).

The results obtained showed that there was a conjugation between BSA and the oxidised mannan, as it is demonstrated by the polyacrylamide electrophoresis [FIG. 4 (BSA conjugated)]. The same figure shows how the fraction of conjugated BSA, retained in the greatest fraction of 100 kDa by ultrafiltration, appeared as BSA monomeric. This implies that a great percentage of the possible formed conjugates went back to the initial condition under denaturalizing circumstances, which indicated that the conjugation reaction with pre-oxidised mannan did not generate products with enough stability. Stabilization of these conjugates can be performed by the chemical process referred to as reductive amination which involves chemical reduction, with sodium cyanoborohydride, of the Schiff bases formed in the conjugation reaction in order to obtain the corresponding more stable secondary amines. However, this reaction implies a new chemical transformation on the initial substrates that generates functional groups and chemical entities (secondary amines) which do not exist in any of the starting reagents (mannan and protein) and which therefore would be necessary to define and characterize.

4.—Mannan Conjugation of the Oxidised Mannan with a Protein Extract from the *Phleum pratense* Allergen Previously Polymerized with Glutaraldehyde.

Figure 5:
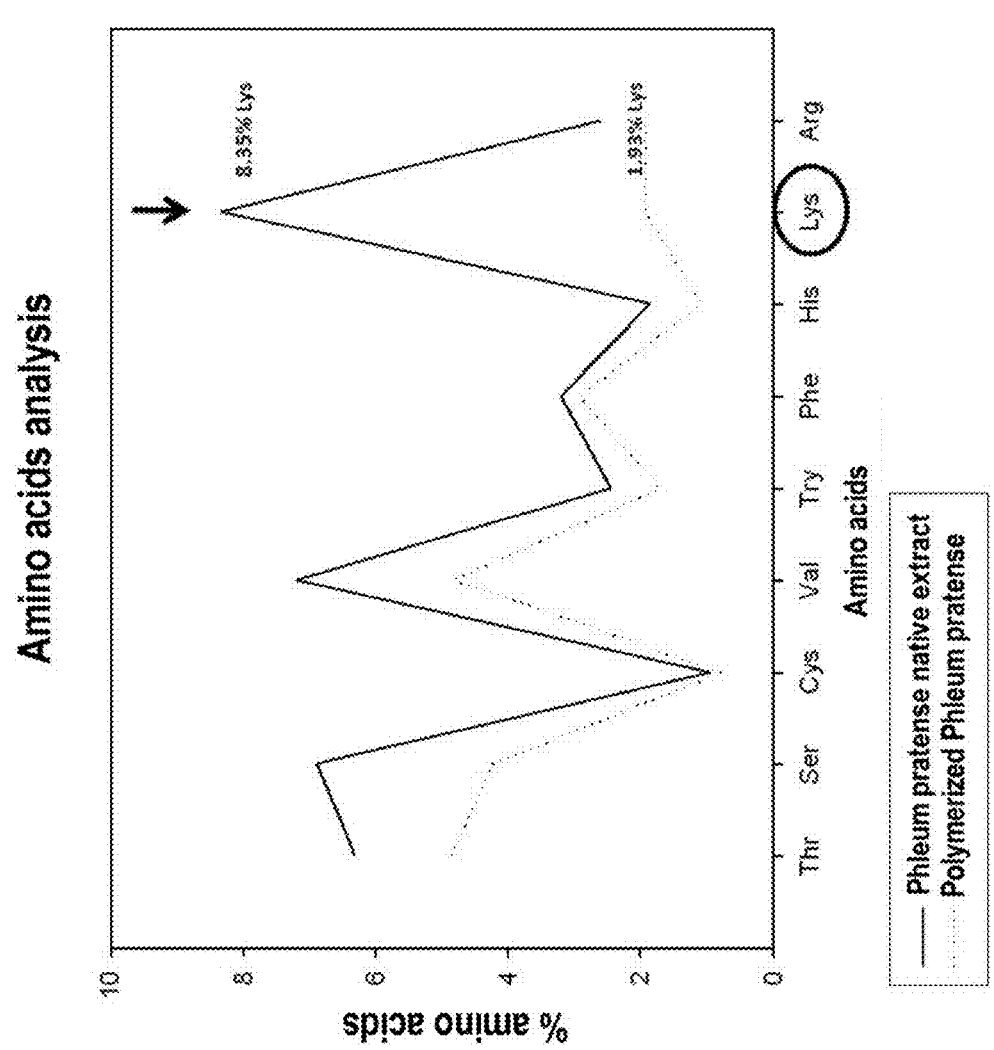
FIG. 5. It is a chart showing the analysis of the amino acids from the native extract of *Phleum pratense* and from the polymer of *Phleum pratense* by gas chromatography. A significant reduction of free lysines is observed in the polymerized sample.

Although it was not an obvious matter that a successful conjugation could be achieved, due to the significant decrease of the free amino groups in the polymers (FIG. 3), conjugation of pre-oxidised mannan with allergen polymerizates from *Phleum pratense* was tested following the protocol described for albumin (Masárová, J. and Mislovicová, D. 2002. Int. J. Polymer. Anal. Charact., 7: 106-116). As it was to be expected, after polymerization with glutaraldehyde, the amount of free lysines is 4.5-fold smaller in the % of total amino acids with respect to the native unpolymerized extract (FIG. 5).

The oxidised mannan was conjugated with the extract from polymerized *Phleum pratense* (material with a molecular size greater than 100 KDa). After that, the reaction product was fractionated again through a 100 KDa membrane. At this step, the retained fraction that is greater than 100 KDa, wherein the original polymerized extract and tha mannan which has been conjugated are found, was collected.

The entire carbohydrate content from the retained sample was analysed by colorimetric analysis with anthrone and there was no significant increase observed in the carbohydrates amount in the sample, compared with the initial content of the polymerized extract not treated with mannan. On the other side, nuclear magnetic resonance studies (one- and two-dimensional studies) did not show a covalent binding between both compounds, nor structural differences at a molecular level, indicating that with this conjugation protocol there was no molecular interaction obtained between both components and, therefore, a binding or conjugation between both products was not obtained. Without wishing to be bound by theory, this could be due to a decrease in the free amino groups (mainly provided by lysines), together with the low accessibility of free residual lysines due to the protein material being a polymer, and thereby a rigid structure with little flexibility. This possibility is supported by the fact that the same negative results were obtained with other allergens previously polymerized with glutaraldehyde, and therefore with a decrease in the free amino groups as it is shown in FIG. 3.

5.—Conclusion

These results make evident the lack of conjugation between the polymerized samples of *Phleum pratense* (and other polymerized allergens) with oxidised mannan. This fact, together with the disadvantages concerning the transformation of mannose after oxidation (FIG. 1) (Shibuya, N., et al. 1988. Journal of Biological Chemistry, 263: 728-734), and the lack of stability of the conjugates formed, even with a lysine-rich protein such as BSA (FIG. 4), makes it possible to dismiss this methodology for its use in the production of polymerized allergen vaccines.

Example 2

Elaboration of Vaccines by Conjugation of Allergens Polymerized with Mannose Using Glutaraldehyde Material and Methods The method for the polymerization and conjugation of protein extracts consists of the following steps:
1. The procedure starts from a lyophilised extract from *Phleum pratense*, which is reconstituted in the required volume of phosphate buffered saline (PBS) so as to reach a final protein concentration of 2 mg/mL. After that, pH is adjusted to 7.2 using potassium phosphate or sodium phosphate buffers, as required to lower or raise the extract pH and the protein concentration is calculated taking into account the buffer volume used to adjust the pH.
   Ex.: Quantity of starting protein: 300 mg of proteins from *P. pratense*.
   PBS required volume: 150 mL
   Required volume to adjust pH to 7.2: 1 mL buffer.
   Final concentration of the sample: 1.986 mg/mL
2. Polymerization and conjugation reaction of the extract:
   The polymerizing agent, in this case glutaraldehyde, is added dropwise on the extract under stirring until reaching a final concentration of 0.025 M.
   The mannan, for the sample conjugation, will also be added at this point at a ratio 1:0.5 (protein mass: mannan mass). The reaction is kept during 15 hours at 4° C. under stirring.
   Ex.: Initial concentration of glutaraldehyde: 2.5 M.
   Volume to be added to the extract: 1.5 mL
   Mannan (protein:carbohydrate ratio 1:0.5): 90 mg.
3. Stopping the reaction:
   The extract is warmed at room temperature (25° C.) and powdered glycine is added to stop the polymerization reaction. Glycine must be in excess, for example, at a ratio of 1:50 with glutaraldehyde. Glycine is dissolved in the sample and is left at 4° C. under stirring, during 2 hours.
   Ex.: Initial glycine concentration (molecular weight: 75.07): 1.25 M
   Glutaraldehyde concentration: 0.025 M
   Extract volume: 152.5 mL (initial 151 mL+1.5 mL glutaraldehyde)
   Glycine quantity to be added: 14.31 g
4. The extract is subsequently dialyzed against 7 volumes of distilled water, in order to remove the salts and possible unpolymerized residues. A cross-flow filtration system is used (Pellicon, Merck Millipore) with a 100 kDa pore membrane.
   Ex.: extract volume: 152.5 mL
   Water volume: 1.525 mL
5. Finally, the extract that is polymerized and conjugated with mannan, is filtrated through 0.22 µm, aliquoted, frozen at −60° C. and lyophilised for its preservation.

Results

As the result of applying said method, a mannosylated polymer immunologically improved with respect to the original allergen was obtained. Treatment with glutaraldehyde allows binding both structures (allergen and mannan), causing that polymerization and conjugation occur at the same time, as it is demonstrated by the results shown in the following example (example 3).

Said mannosylated polymer has structural and immunological properties which are superior to those of the native or polymerized and non-mannosylated allergen, as it is shown in example 4 and in examples 5-10, respectively.

Figure 6:
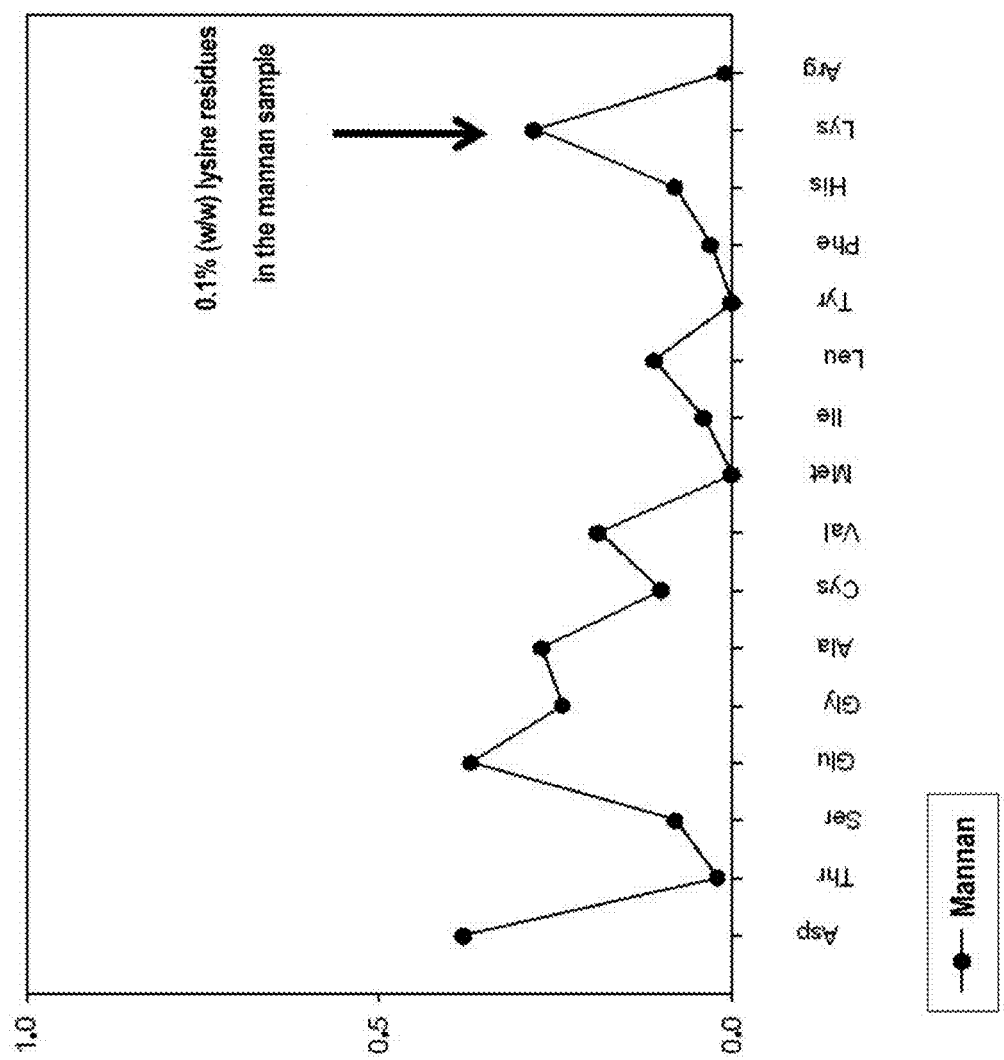
FIG. 6. It is a chart showing the analysis of the amino acids from a mannan stock sample from *S. cerevisiae*.

Thus, a method is established for the conjugation of antigens polymerized with mannan using glutaraldehyde in a single step, wherein the integrity of the mannose structure is kept. In order to do so, on the one side it is made good use of the fact that mannan from natural origin, e.g. from *Saccharomyces cerevisiae*, has a peptide residue of the original mannoprotein on which mannan is synthesized in yeasts containing lysines (FIG. 6), resulting in a chemical conjugation. On the other hand, it is well used the polymeric, branched and rigid structure of mannan in solution with a polymer from a protein, in which the former is trapped by the protein which is being polymerized by glutaraldehyde, resulting in a physical conjugation. In any of both cases, without being mutually exclusive, glutaraldehyde treatment of the mixture of the protein in its native form (unpolymerized) with mannan allows binding both structures, which produces conjugation and polymerization at the same time.

Example 3

Evidence on Allergen (Gramineae and Mites) Polymerization and Conjugation with Mannan by Reaction with Glutaraldehyde Material Y Methods 2 mg aliquots of the lyophilised samples obtained in example 2 were dissolved in 0.5 mL of heavy water and analysed by nucleas magnetic resonance (NRM) in a 500

MHz Bruker Advance spectrometer or in a 600 MHz Bruker Advance equipped with cryoprobe. One-dimensional proton resonance spectra, two-dimensional proton-carbon13 hetronuclear correlation spectra (HSQC; Zwahlen et al., 1997. J. Am. Chem. Soc. 119: 6711-6721) and two-dimensional spectra ordered by translational diffusion (DOSY, Wu et al. 1995. J. Magn. Reson. A. 115: 260-264) were acquired from the different samples, following the protocols standardized and implemented by the manufacturer, Bruker Biospin Corporation, (Billerica, Mass., USA), in the spectra acquisition and processing software TOPSPIN.

The carbohydrate and protein content of the samples was analysed by colorimetric techniques, using the anthrone method (Shields, R. and W. Burnett. 1960. Analytical Chemistry 32: 885-886) for the analysis of total carbohydrates, and the Bradford method for the analysis of proteins (Bradford, M. M. 1976. Analytical Biochemistry 72: 248-254).

An analysis was carried out of the different monosaccharides rate from the glucidic part of the samples, by means of total acid hydrolysis and gas chromatography analysis of the monosaccharides released in the form of the alditol acetates thereof (M. F. Chaplin & J. F. Kennedy editors, Carbohydrate Analysis: a practical approach. (1986) Oxford IRL PRESS).

An analysis was carried out of the different amino acids in the protein part of the samples by total acid hydrolysis of the samples and analysis by liquid chromatography of the released amino acids in a Biochrom Aminoacid Anlyzer apparatus.

Results 3.1.—Studies of the Joint Polymerization of *Phleum pratense* with Different Proportions of Mannan in Order to Establish the More Suitable Proportion Enabling an Adequate Conjugation of the Extract Polymerized with Mannan.

Figure 7:
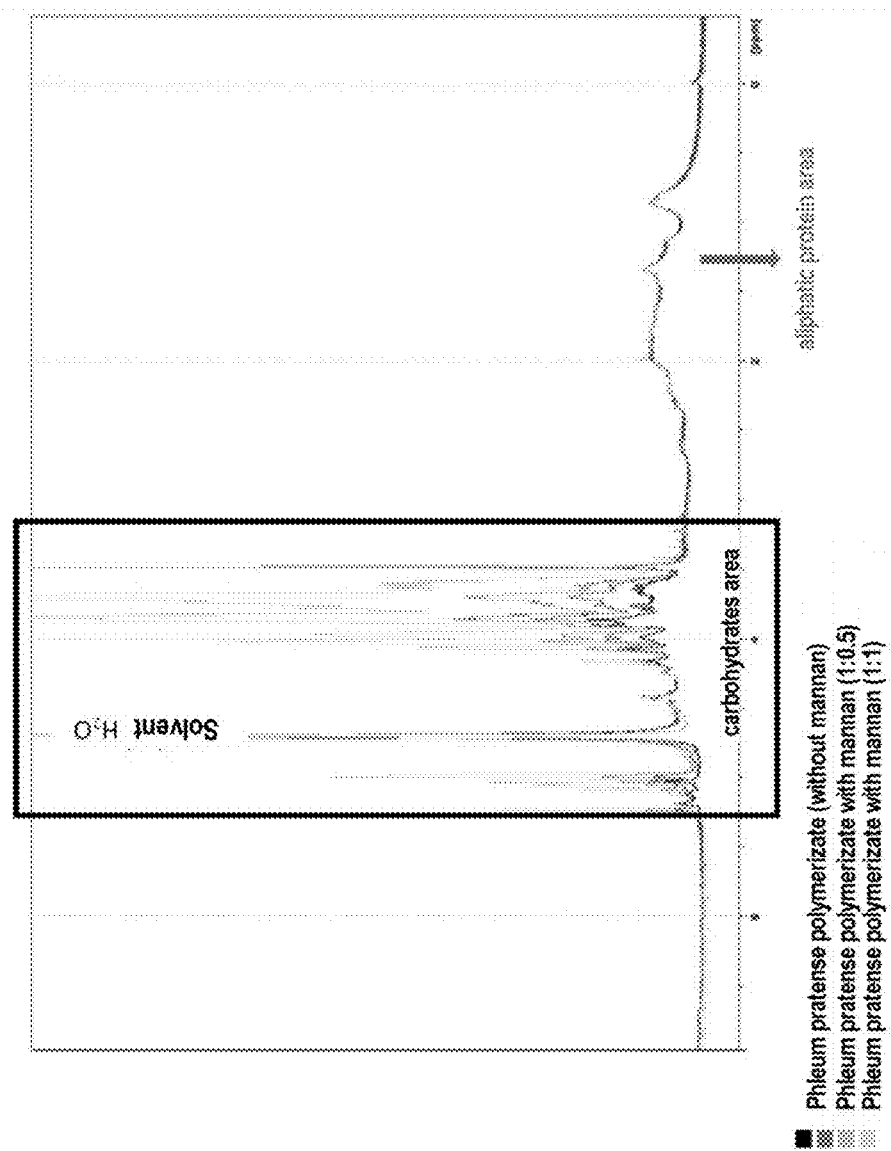
FIG. 7. It is a chart showing the one-dimensional spectrum of samples polymerized with mannan at different ratios (protein:carbohydrate). A sample polymerized without mannan was used as control.
Figure 8:
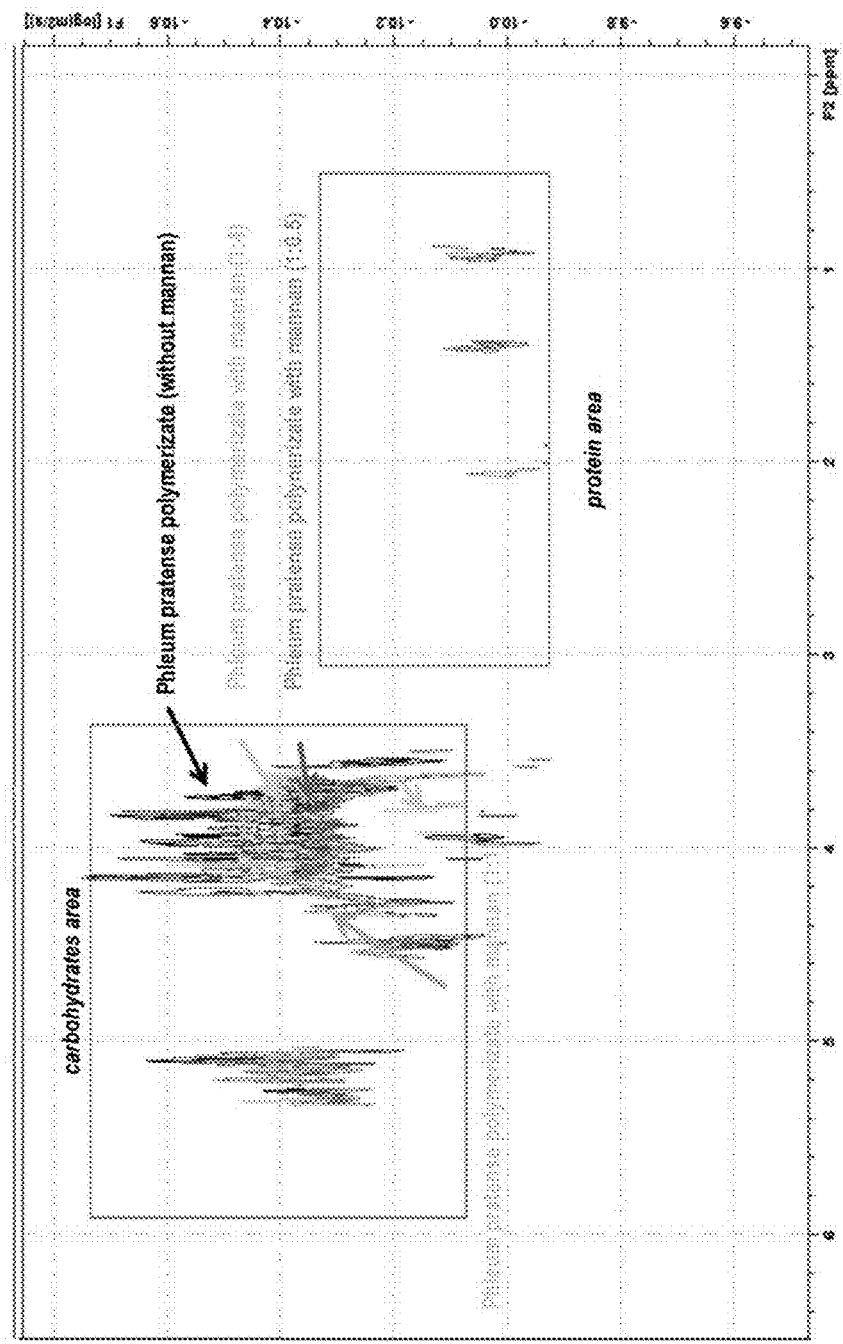
FIG. 8. It is a chart showing a two-dimensional spectrum (DOSY) "Diffusion Ordered SpectroscopY", of samples polymerized with mannan at different ratios (protein:carbohydrate). A sample polymerized without mannan was used as control.

The structure of the samples obtained in this process with different ratios of protein:mannan was analysed by nuclear magnetic resonance (NMR), using a polymerizate sample without mannan. The protein extract polymerized on its own had oligosaccharide residues belonging to the sample itself (12-20%), which was confirmed by gas chromatography (monosaccharide analysis). By increasing the sugar amount in the medium, the polysaccharide signal in the spectrum was also increase, as it was expected to be (FIG. 7). A translational diffusion study was carried out, study which orders the compounds according to its diffusion coefficient, and which in turn depends on the molecular size (two-dimensional spectrum by NMR; two-dimensional spectrum (DOSY) "Diffusion Ordered SpectroscopY"). In this study, it could be observed that in the samples polymerized with mannan there were bigger particles than in unpolymerized samples, which would indicate an association between the protein extract and the mannan in all the cases (FIG. 8). Particularly, in the case of the ratio of 1:4 a high amount of the oligosaccharide part was observed, possibly due to the excess of carbohydrate in the reaction medium.

On the other hand, the protein and sugar amount was quantified so as to try and establish, roughly speaking, the protein:sugar ratio of the samples that had undergone the polymerization process and compare it to the initial proportions. (Table 1).

TABLE 1

Comparison of the protein:mannan ratio before and after polymerization

| Protein:mannan ratio (dry weight) (Before polyemerization process) | Protein:mannan ratio (Bradford/anthrone) (after polymerization process) |
| --- | --- |
| 1:0.5 | 1:0.8 |
| 1:1 | 1:1.3 |
| 1:4 | 1:3 |

In the case of the polymerized sample in the ratio of 1:4, it was normal to obtain a lower proportion in the sugars amount after the process, due to the great initial excess in which it is found in the reaction medium, removing the unreacted part in the washing step. In the remaining samples, there was found an increase of the polysaccharide proportion compared to the initial proportion, which is due to the extract itself having covalently bound polysaccharide residues.

Once having all the data, the ratio (1:0.5) was chosen, since it confirms carbohydrate incorporation to the sample and minimizes the use of mannan.

3.2.—Joint Polymerization Analysis of *Phleum pratense* at the Protein-Carbohydrate Ratio.

3.2.1 Carbohydrate Analysis by Gas Chromatography

Starting from a dissolution of lyophilized material, the carbohydrate percentage in dry weight with respect to the whole sample was quantified using gas chromatography, by acid hydrolysis (alditol analysis) (Fukuda, M. & Kobata, A. 1993. Glycobiology. A Practical Approach. The practical Approach Series. Oxford University Press Inc., New York.).

Figure 9:
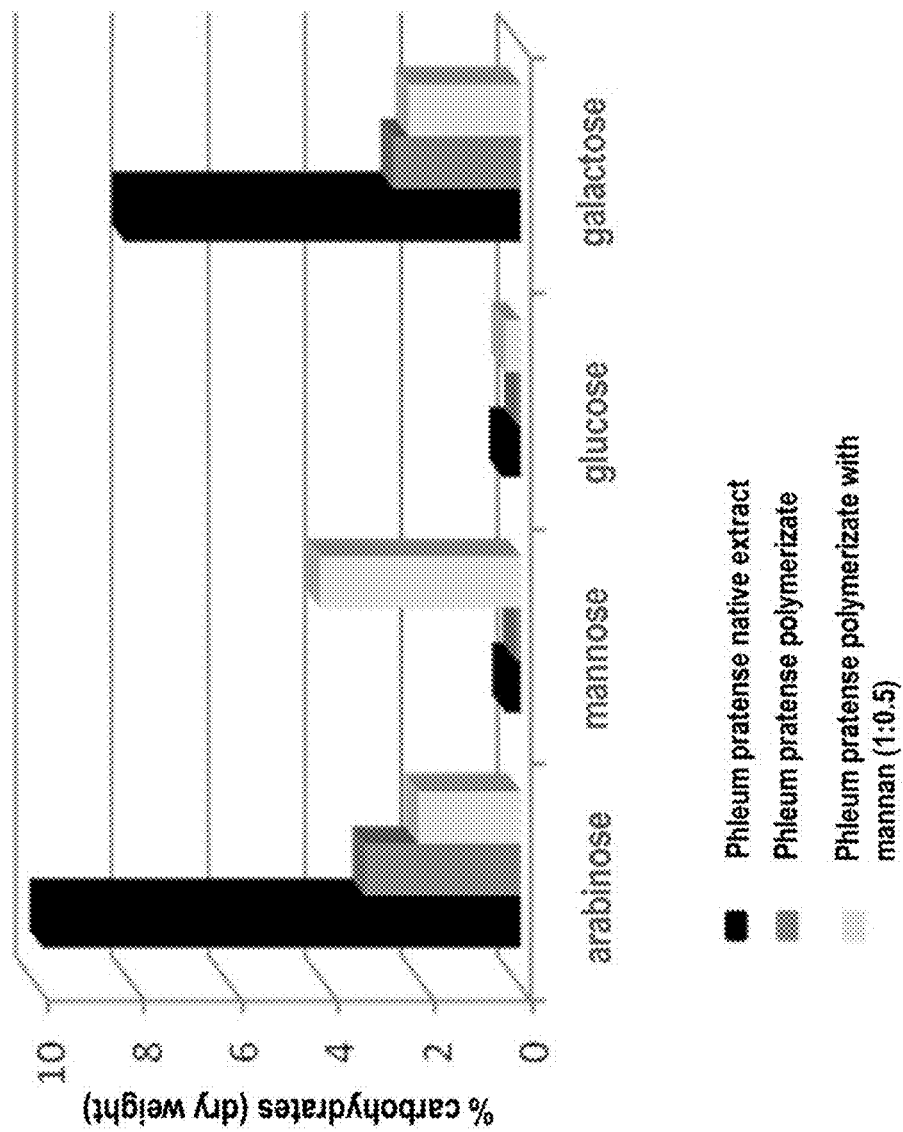
FIG. 9. It shows a graphic representation of the percentage of monosaccharides of the different samples analysed by gas chromatography of *Phleum pratense*.

Three samples were analysed (FIG. 9):

*Phleum pratense* Native extract

*Phleum pratense* Polymerized

*Phleum pratense* Polymerized with mannan (1:0.5)

The results showed a significant increase of mannose in the samples subjected to joint polymerization with respect to the polymerized sample (without mannan) and to the native extract.

3.2.2 NMR (Nuclear Magnetic Resonance) Studies

Figure 10:
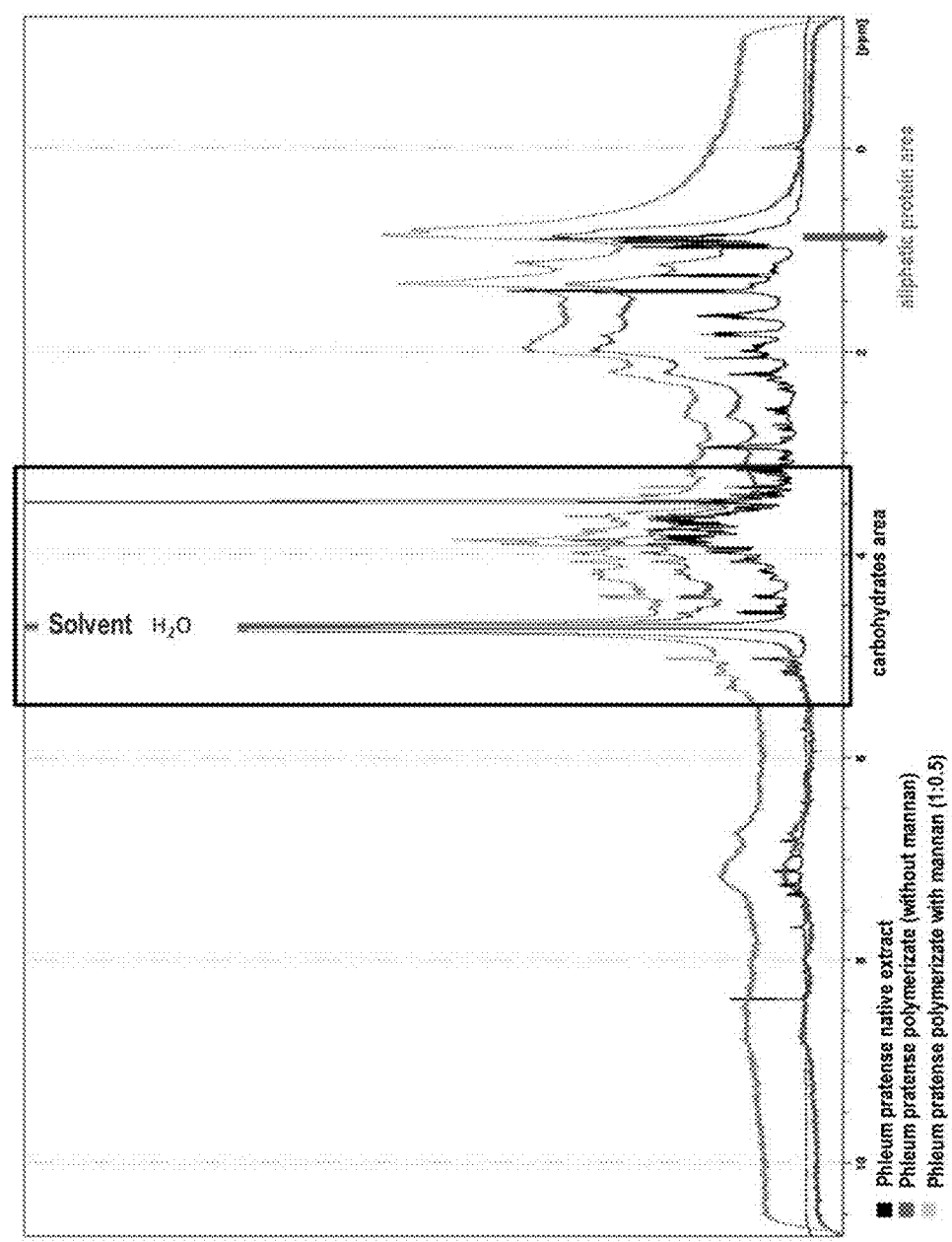
FIG. 10. It is a chart showing the one-dimensional spectrum comparing samples of *Phleum pratense*: native extract (unpolymerized), polymerized (without mannan) and with joint polymerization at a ratio (1:0.5).
Figure 11:
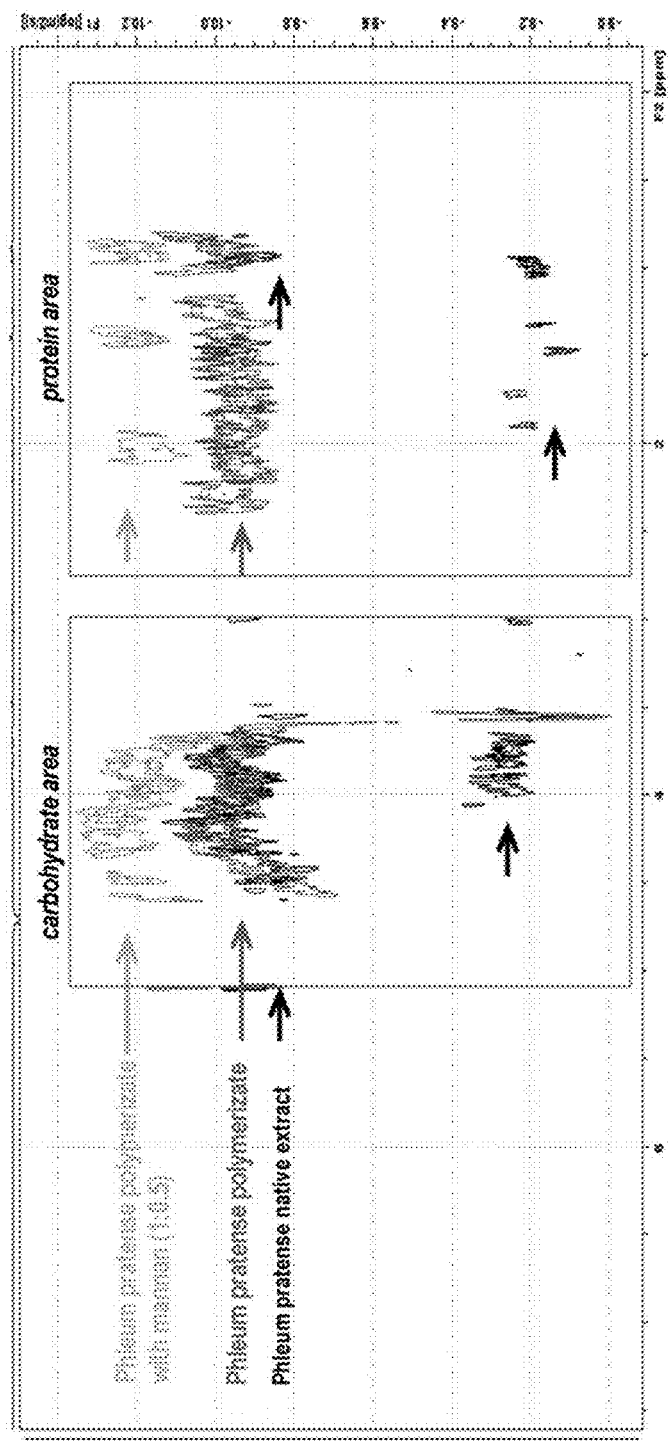
FIG. 11. It is a chart showing the two-dimensional spectrum (DOSY) "Diffusion Ordered SpectroscopY", from samples of *Phleum pratense*, unpolymerized, and polymerized with and without mannan.

The structural studies by NMR show a broadening of the signals in the polymerized samples, indicating a size increase, which is corroborated in the two-dimensional spectrum from the translational diffusion DOSY (Diffusion Ordered SpectroscopY) (FIGS. 10 and 11). In this two-dimensional experiment, it can be observed that, in the case of the unpolymerized protein extract, there is different size material and therefore it is a very heterogeneous sample which increases its average molecular size when polymerizes. On the other hand, when the extract is polymerized in the presence of mannan, a material is also obtained having an even lower diffusion coefficient (indicative data of a greater size), than the polymerizate (due to the polysaccharide being of a high molecular weight), indicating binding or interaction between the polysaccharide and the protein extract, since both parts of the spectrum, the carbohydrates area and the protein one, have the same diffusion coefficient, indicating an interaction between both components. These nuclear magnetic resonance experiments corroborate the conjugation protein:mannan after polymerization of the protein extract using glutaraldehyde in the presence of mannan.

On the other hand, another two-dimensional study by NMR was carried out based on the heteronuclear correlation between carbon 13 and proton (13C-1H) (HSQC, "Heteronuclear Single Quantum Coeherence"). These studies show, at an atomic level, the bonds between a hydrogen and a carbon, with each bond corresponding to a concrete correlation signal (peak) from the spectrum and a position (coordinates: abscissas, chemical shift of $^1H$; ordinates: chemical shift of $^{13}C$) which is different depending on the type of compound. The group of signals (H—C bonds) cause a two-dimensional pattern which is specific and exclusive for each compound, in a way similar to a "fingerprint" (Claridge, T. D. W. 1999. High-resolution NMR techniques in Organic Chemistry. Tetrahedron Organic Chemistry Series. Elsevier).

Three HSQC experiments were done to distinguish the characteristic pattern of each type of sample:
  Mannan free
  Polymerizate from *Phleum pratense*
  Polymerizate from *Phleum pratense* in the presence of mannan (1:0.5)

Figure 12:
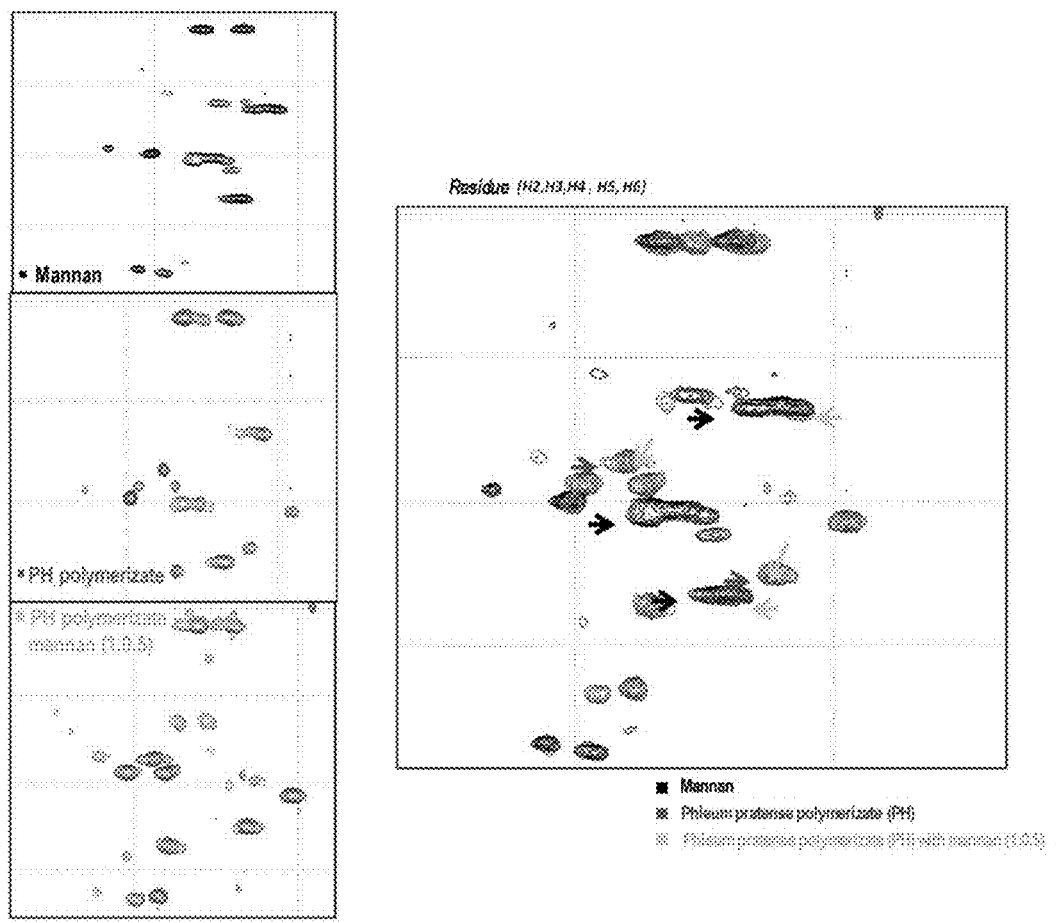
FIG. 12. It is a chart showing the two-dimensional spectrum HSQC (H—C) wherein different samples of *Phleum pratense* are compared. Enlarged region of the non-monomeric area.

The sample polymerized in the presence of mannan presents the characteristic signals of mannan and those of the intrinsic carbohydrates of the sample itself, indicating the interaction between the protein extract and the polysaccharide (FIG. 12).

Figure 13:
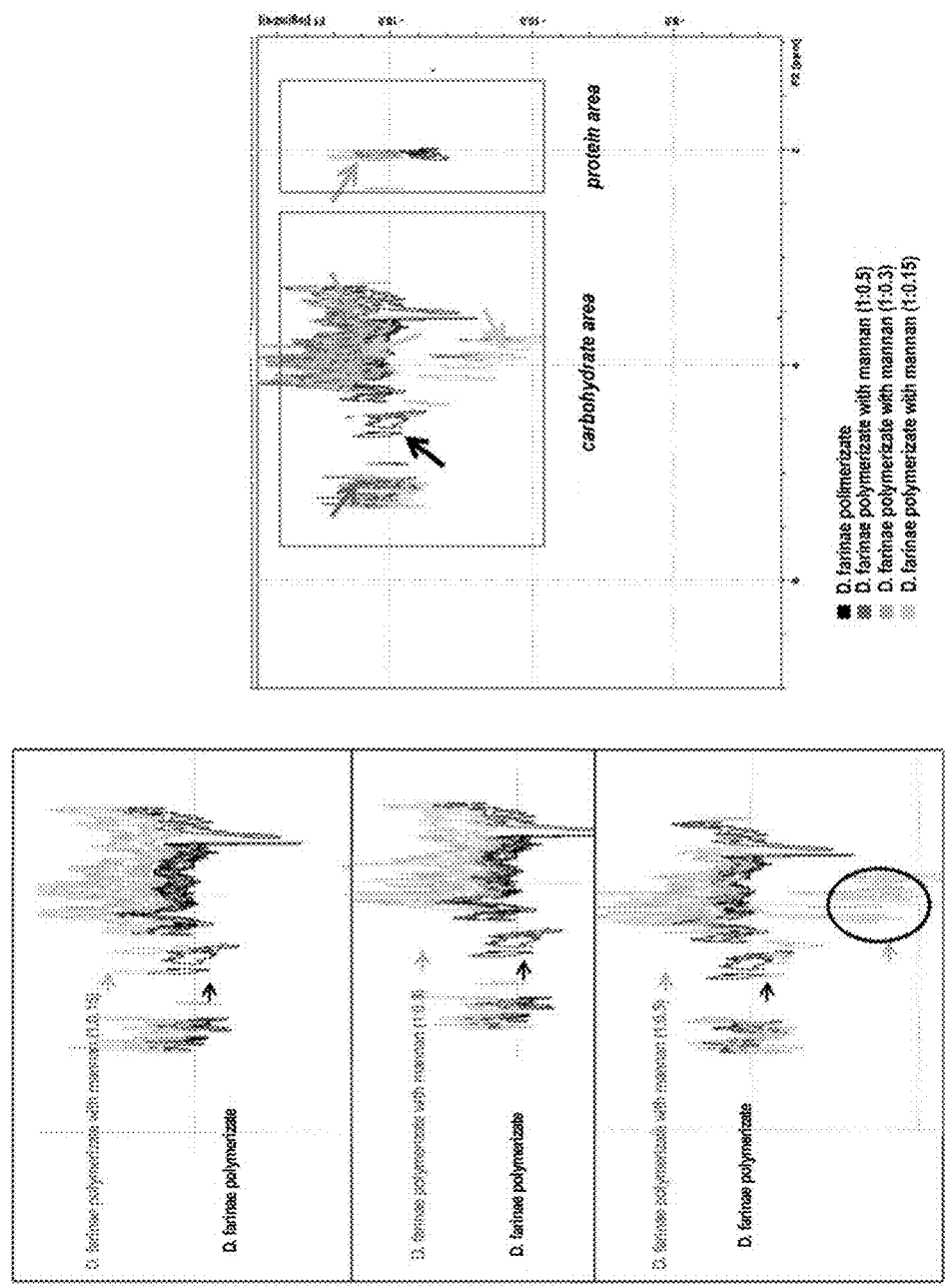
FIG. 13. It is a chart showing the two-dimensional spectrum (DOSY) "Diffusion Ordered SpectroscopY", from mite extract samples of (*D. farinae*) polymerized with mannan at different ratios (protein:carbohydrate). A sample polymerized without mannan was used as control.

3.3.—Studies of the Joint Polymerization Process of *D. farinae* with Different Mannan Proportions Starting from the results obtained with *Phleum pratense*, preliminary experiments were performed with the protein: carbohydrate ratio of (1:0.5); nevertheless, the results obtained were not as satisfactory as for each case of the *Phleum pratense* extract, since an excess of mannan residues were observed which were not associated to protein material (FIG. 13, signal delimited by the black circle). New polymerizations were performed with a lower carbohydrate ratio in the medium (1:0.3 and 1:0.15). The chosen ratio was (1:0.3), since it was observed an incorporation of mannan in the sample mainly in the form associated to the protein (FIG. 13, box b) and not in a free form (FIG. 13 box c black circle), and this incorporation of mannan was higher than that with the ratio of (1:0.15) and in the greatest disturbance observed, also for the ratio of 1:0.3, in the spectrum area corresponding to the protein part (FIG. 13).

3.3.1 Analysis of the Joint Polymerization of *D. farinae* at the Protein: Carbohydrate Ratio of (1:0.3)

Figure 14:
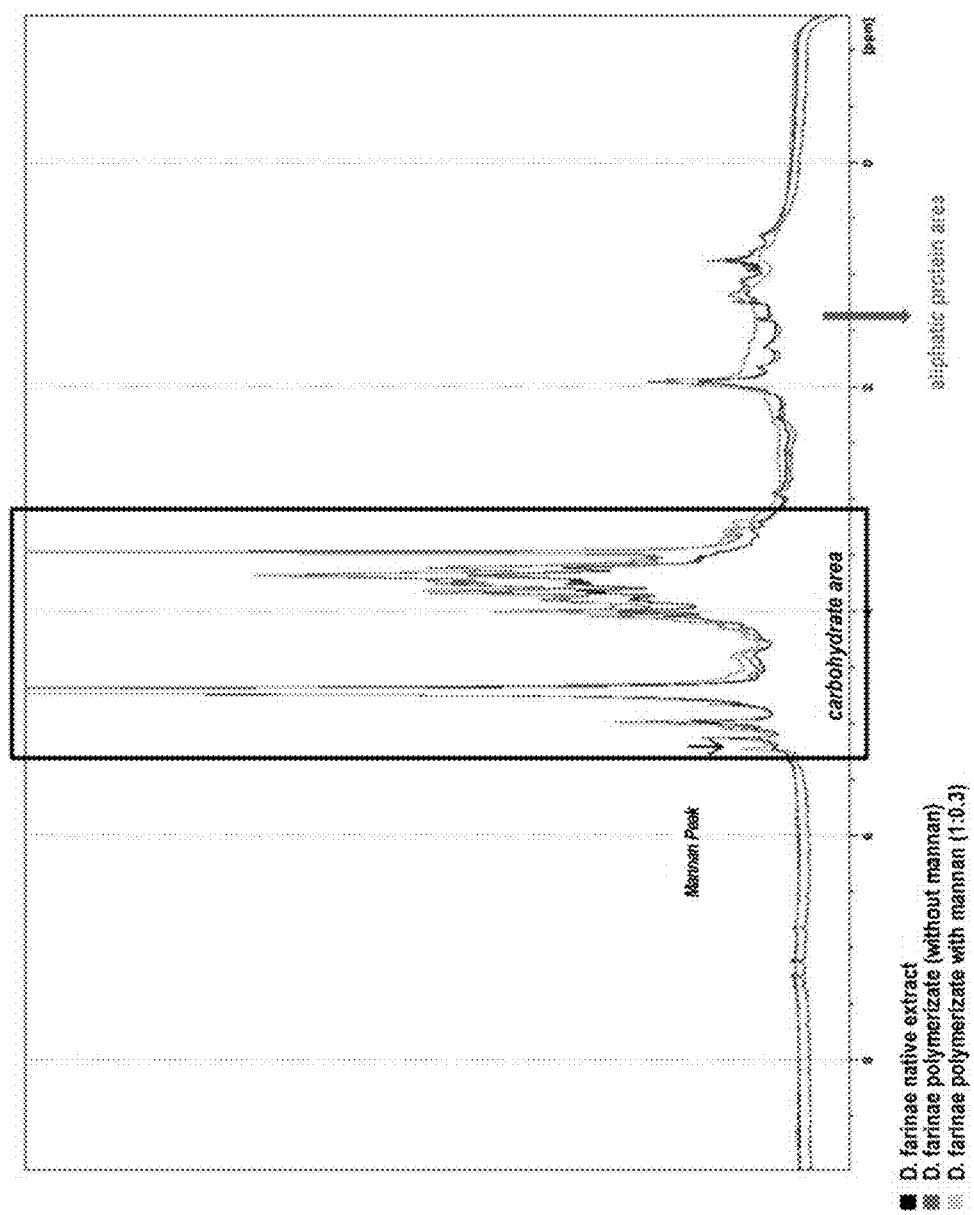
FIG. 14. It is a chart showing overlapping one-dimensional spectra from samples of *D. farinae*: native extract, polymerized (without mannan) and with joint polymerization at a ratio (1:0.3).

FIG. 14 shows the qualitative comparison of the one-dimensional proton spectra of a sample from a *D. farinae* extract polymerized in the presence of mannan at a ratio of 1:0.3 with reference to a sample polymerized in the absence of mannan and to an unpolymerized extract sample. The spectrum indicates the specific signals for mannan in the sample polymerized with mannan, as well as the spectroscopic pattern change, caused by polymerization, in the spectrum area specific for the protein.

3.3.1.1 Carbohydrate Analysis by Gas Chromatography

Starting from a lyophilised material dissolution, the carbohydrate percentage in dry weight with respect to the whole sample, was quantified by gas chromatography (Fukuda, M. & Kobata, A. 1993. Glycobiology. Oxford University Press Inc., New York).

Figure 15:
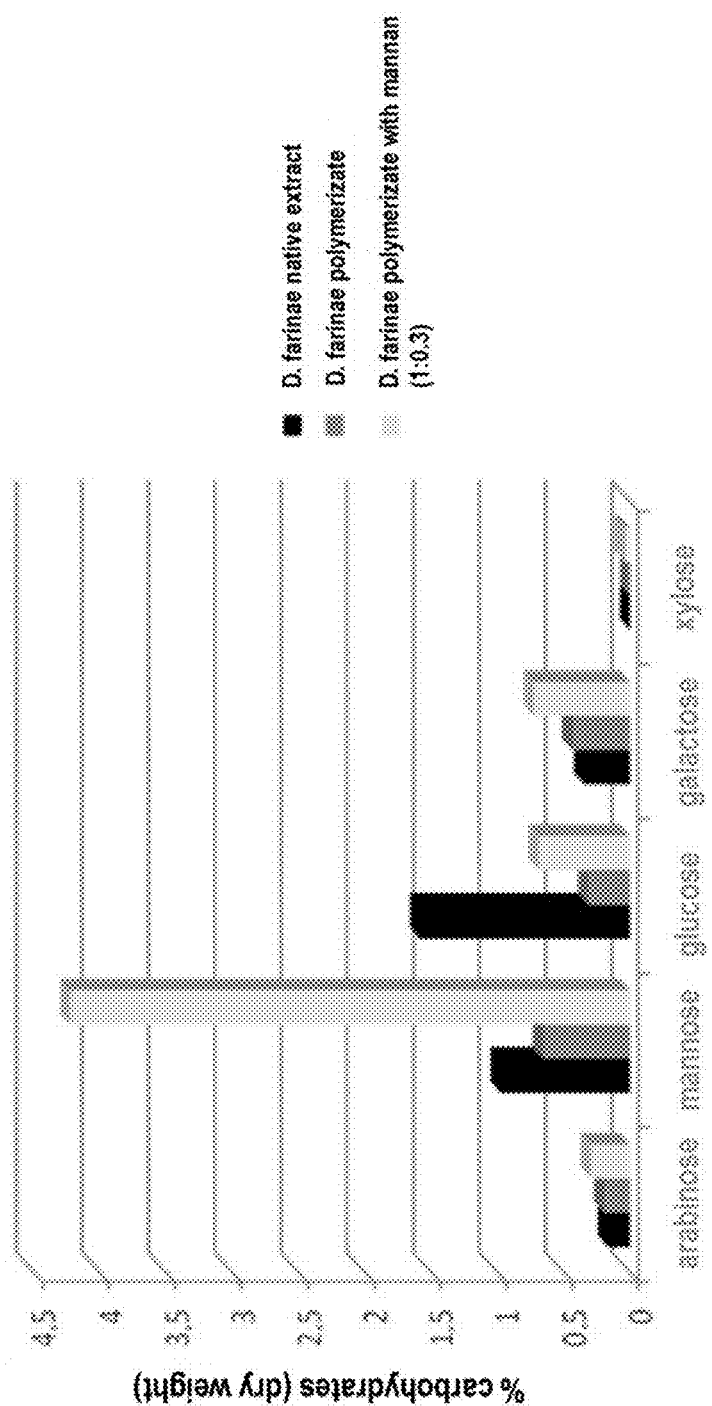
FIG. 15. It shows a graphic representation of the percentage of monosaccharides of the different samples analysed by gas chromatography of *D. farinae*.

Three samples were analysed (FIG. 15):
  *D. farinae* Native extract
  *D. farinae* Polymerized
  *D. farinae* Polymerized with mannan (1:0.3)

Extracts and polymerizates of *D. farinae* contain intrinsic oligosaccharide residues in the sample itself (approximately 17-20% determined by gas chromatography with a greater presence of glucose, mannose and galactose). The results for the joint polymerization product with mannan showed a significant increase of mannose, both with respect to the sample polymerized without mannan and to the native extract.

3.3.1.2 NMR (Nuclear Magnetic Resonance) Studies

Figure 16:
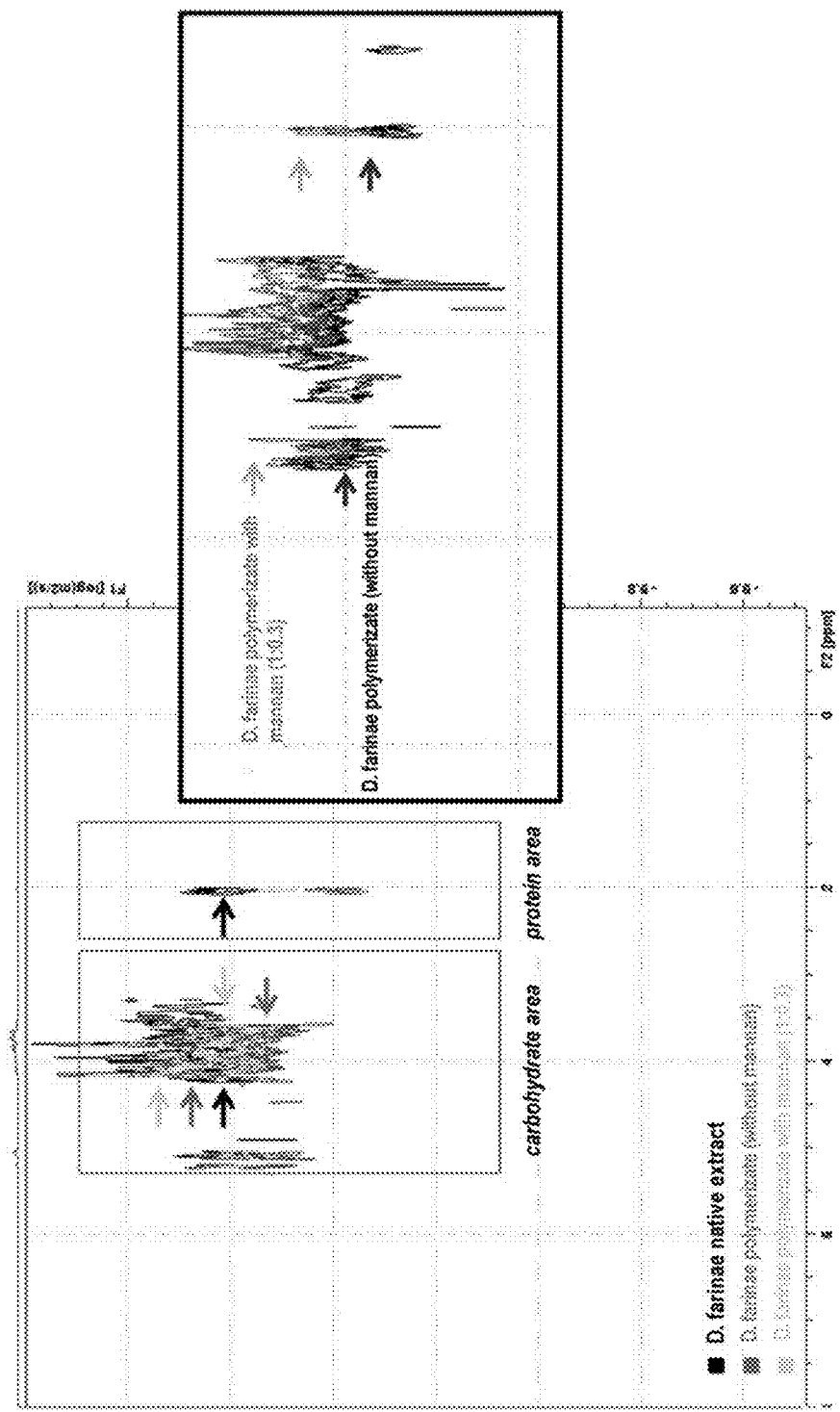
FIG. 16. It is a chart showing the two-dimensional spectrum (DOSY) "Diffusion Ordered SpectroscopY", from samples of *D. farinae*, unpolymerized, and polymerized with or without mannan.

The samples obtained in the simultaneous polymerization and conjugation at the ratio of (1:0.3) (protein:mannan), were analysed by NMR. These results showed a broadening of the signal in polymerized samples, indicating an increase in the molecular size which is corroborated in the two-dimensional spectrum DOSY" (FIG. 16). Similarly to the case of *Phleum pratense*, the sample polymerized with mannan was homogeneous and of a bigger size to that polymerized without mannan, indicating an association between the polysaccharide and the protein extract of *D. farinae* and therefore, confirming the conjugation of both components.

3.3.1.3 Transmission Electron Microscopy

Figure 17:
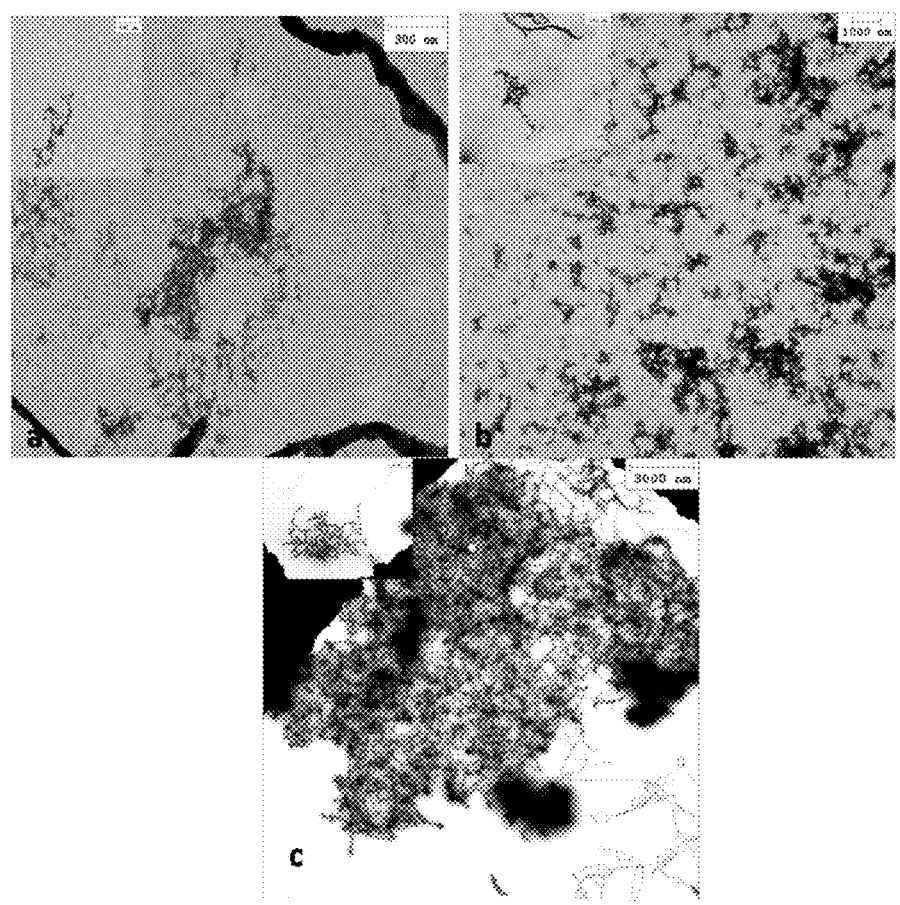
FIG. 17. It is an electron microscopy image of the samples of *D. farinae* of: a) native extract, b) polymerized and c) polymerized with mannan (1:0.3).

Images from transmission electron microscopy of the different samples of *D. farinae*, allowed us to observe differences at a structural level between the native and polymerized extracts. Where the polymerization offers a higher density in the particles and the conjugation with mannan also produces changes at a morphological and structural level which are clearly seen in the polymer, being further evidence of the association between the polysaccharide and the protein extract (FIG. 17).

Example 4

Figure 18:
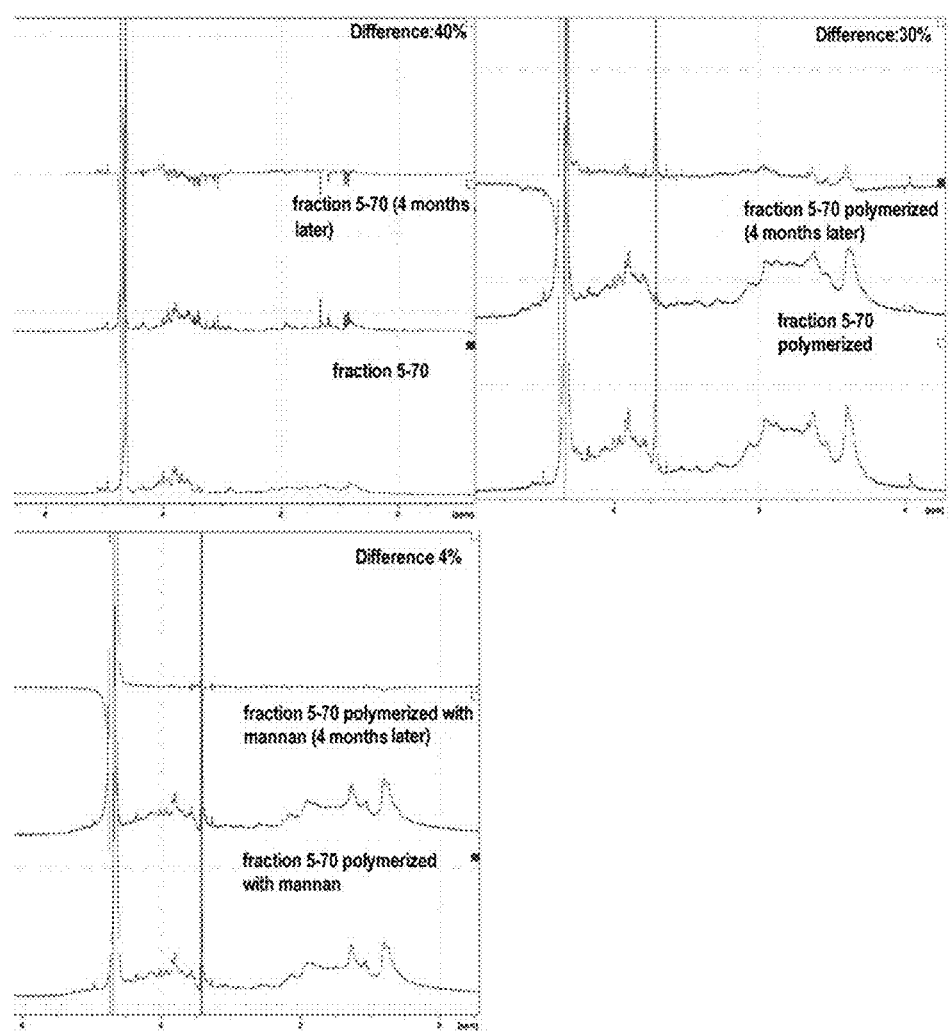
FIG. 18. It is a group of charts showing the one-dimensional proton spectra of *Phleum pratense* at different times.

Polymerization and Mannosylation by Reaction with Glutaraldehyde Generates Polymers More Stable than Non-Mannosylated Polymers The stability of three samples of *Phleum pratense* was compared, one of them polymerized in the presence of mannan (protein/mannan ratio of 1:0.5), another polymerized in the absence of mannan and the allergen itself unpolymerized, against long term storage in an aqueous medium. Aliquots of samples equivalent to those analysed in example 3 were dissolved in heavy water and analysed by NMR and then storage at 4° C. The samples were not taken out of the NMR tubes nor were manipulated otherwise. 4 months after storage the NMR experiments were repeated following the same acquisition parameters so as to check the stability of the samples under these dissolution conditions (heavy water at 4° C.). The results, presented as the difference of the spectra at the initial time and after 4 months (subtraction of spectra performed by the spectrometer own TOPSPIN software), showed that the polymerized samples were more stable than the native extracts (40% signal loss), and that conjugation with mannan increased stability even more, since only a 4% of the sample signal was lost, indicating a low index of the sample degradation/precipitation (FIG. 18).

Example 5

Polymers Mannosylated with Glutaraldehyde are Comparable to Non-Mannosylated Polymers Regarding their Loss of Allergenicity 5.1.—Reactivity Assays with Specific IgE Antibodies
  Material and Methods IgE reactivity assays were carried out by inhibition ELISA techniques. 96 well plates (Microlon, high binding capacity, Greiner bio-one, Germany) were plated with 1 μg of the native extract per well diluted in a 0.05 M carbon/bicarbonate buffer, pH=9.6. The plates were left at 4° C. overnight. The following day the plates were washed with PBS-t buffer (phosphate buffer with 0.25% Tween-20), and they were added the corresponding serum pool in each case from allergic patients (allergic to gramineae or mites) and the inhibitors (native extract, polymerized extract and mannosylated polymerized extract), by ½ serial dilutions from 100 μg/mL to 0.01 μg/mL. The plates were incubated with the mixture overnight, and the following day, after washing with PBS-t, they were incubated with anti-human IgE monoclonal antibody conjugated with peroxydase (Southern Biotech, USA) at a 1:2000 dilution. The plates were developed with OPD system (Sigma Aldrich, USA) for 30 minutes. The reaction was stopped with hydrochloric acid ¹/₁₀ diluted in water and the plates were read at 492 nm.

IgE reactivity of the native extracts, polymerized and polymerized and mannosylated, was also analysed by electrophoresis and immunodetection. Protein separation of the extracts was carried out in polyacrylamide gels under denaturalizing conditions (SDS-PAGE). Immunodetections were performed transferring the proteins separated by electrophoresis to cellulose nitrate membranes (Bio Rad, Germany). The membranes were blocked with PBS-t with 5% BSA (bovine serum albumin) and incubated with sera from allergic patients. Afterwards, they were incubated with an anti-human IgE monoclonal antibody conjugated with peroxidase (Southern Biotech, USA) at a 1:2.000 dilution. ECL chemiluminescence system was used for development (GE-Healthcare, USA).

Results 5.1.1 Loss of IgE Reactivity with Polymers of *Phleum pratense* Mannosylated with Glutaraldehyde is Comparable to that of Non-Mannosylated Polymers.

Figure 19A:
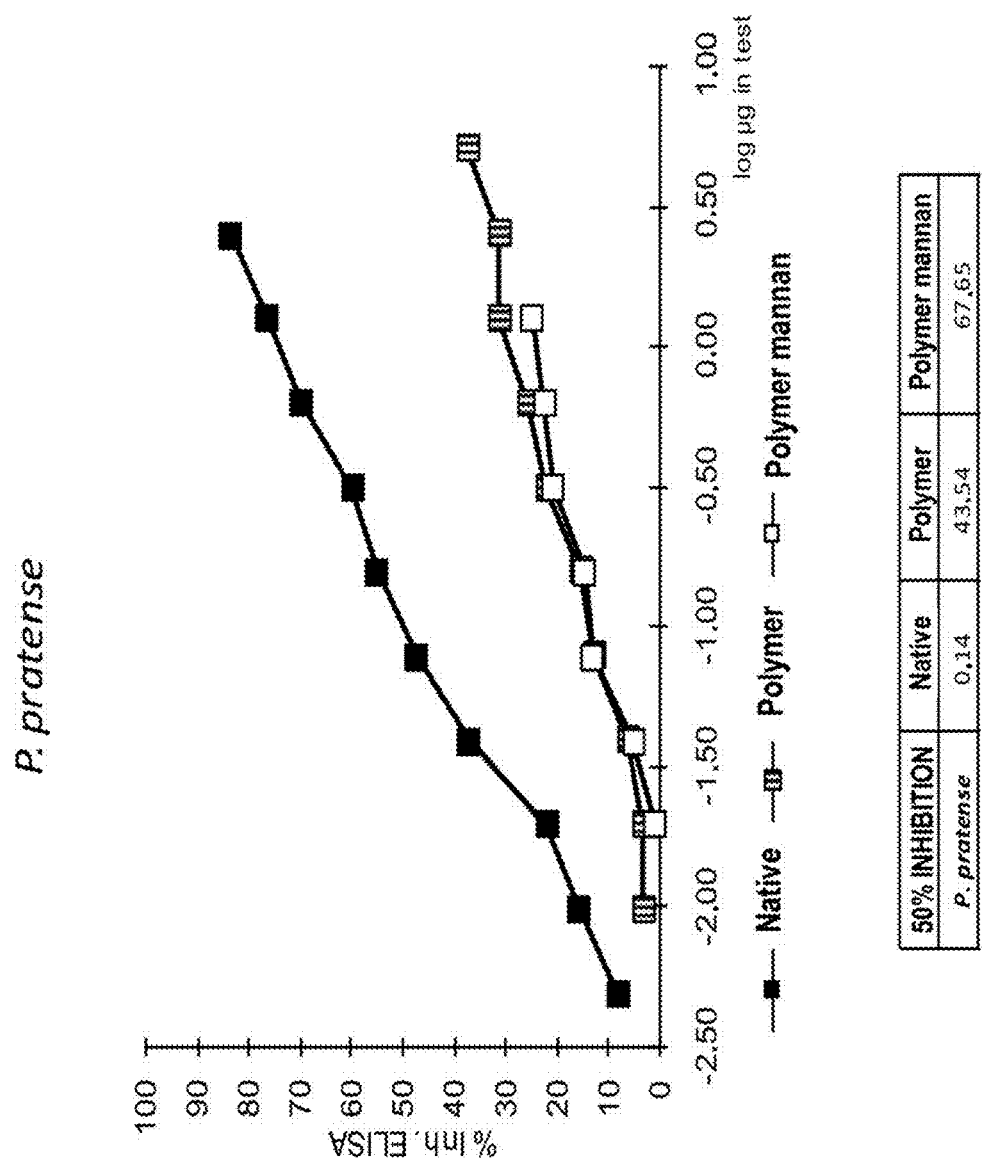
FIG. 19A is a chart showing the results of ELISA assays for IgE-binding inhibition to a native extract of *Phleum pratense* with the native allergen (unpolymerized), polymerized non-mannosylated allergen and allergen mannosylated with glutaraldehyde.
Figure 19B:
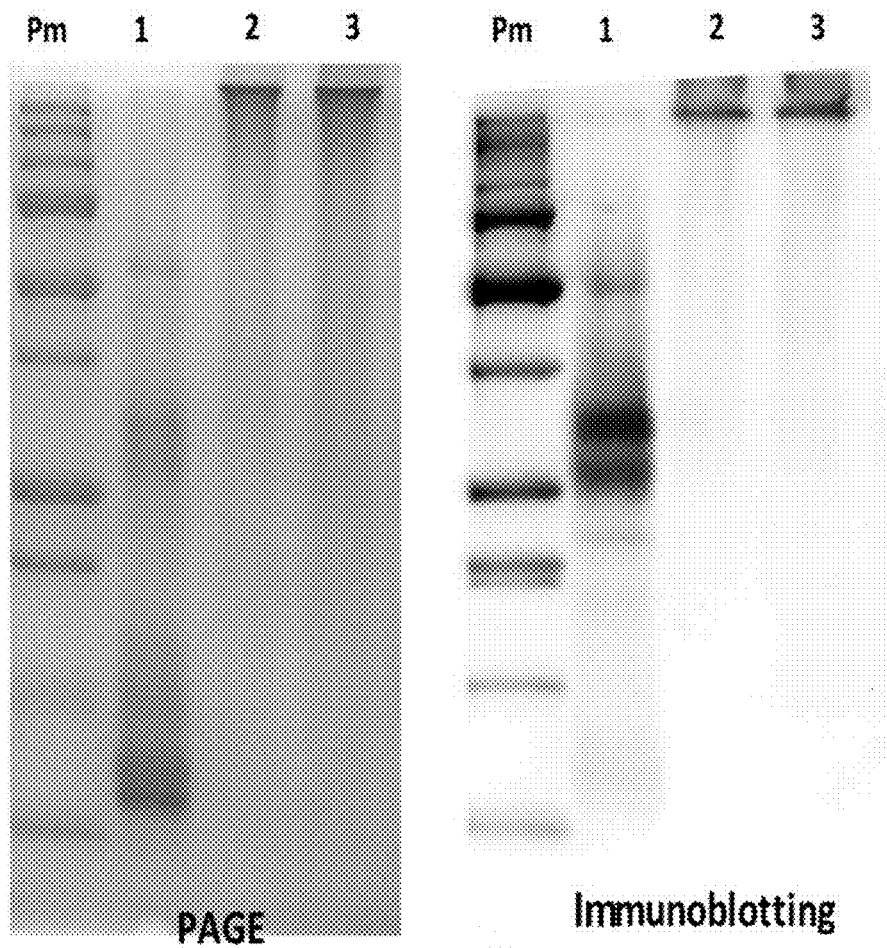
FIG. 19B is an image corresponding to a polyacrylamide gel electrophoresis in the presence of SDS (SDS-PAGE) and immunodetection (immunoblotting) with sera from allergic patients, of an extract of *Phleum pratense*: IgE reactivity with proteins separated by PAGE. Pm=molecular weights pattern; 1=native allergen; 2=polymerized non-mannosylated allergen; 3=allergen mannosylated with glutaraldehyde.

FIG. 19A shows an inhibition ELISA where it can be appreciated that the polymerized allergens of *P. pratense* mannosylated or not, show less IgE reactivity than the native allergens. FIG. 19B shows the bands corresponding to the allergenic proteins of *P. pratense* both in the gel electrophoresis and in the immunodetection carried out with the serum from allergic patients, whereas in the lanes corresponding to the polymerized allergen and to the polymerized and mannosylated allergen no bands (PAGE-SDS) or IgE binding (immunodetection) is observed.

5.1.2 Loss of IgE Reactivity with Polymers of *D. pteronyssinus* and *D. farinae* Mannosylated with Glutaraldehyde is Comparable to that of Non-Mannosylated Polymers.

Figure 20A:
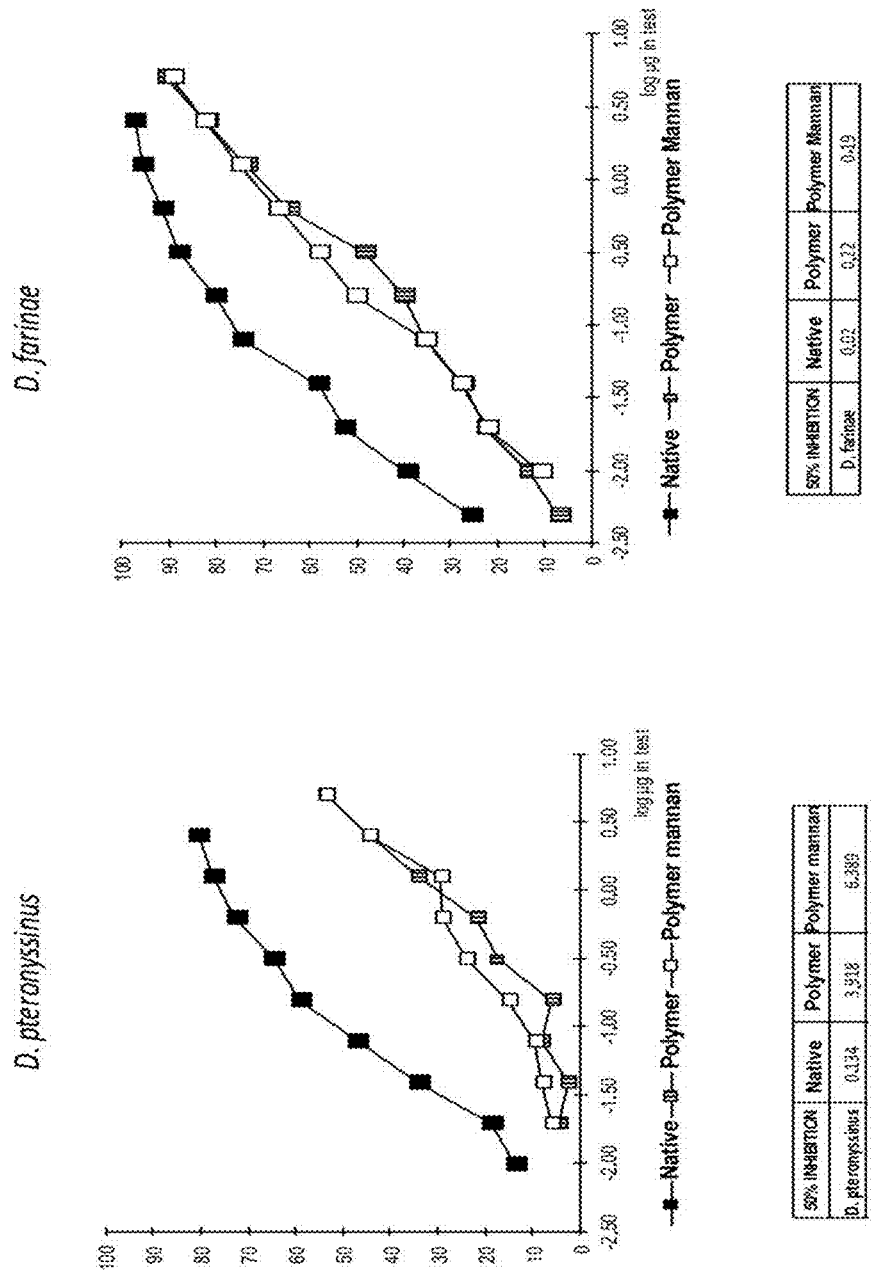
FIG. 20A is a chart showing the results of ELISA assays for IgE-binding inhibition to a native extract of *D. pteronyssinus* and *D. farinae*, respectively with the native allergen (unpolymerized), polymerized non-mannosylated allergen and allergen mannosylated with glutaraldehyde.
Figure 20B:
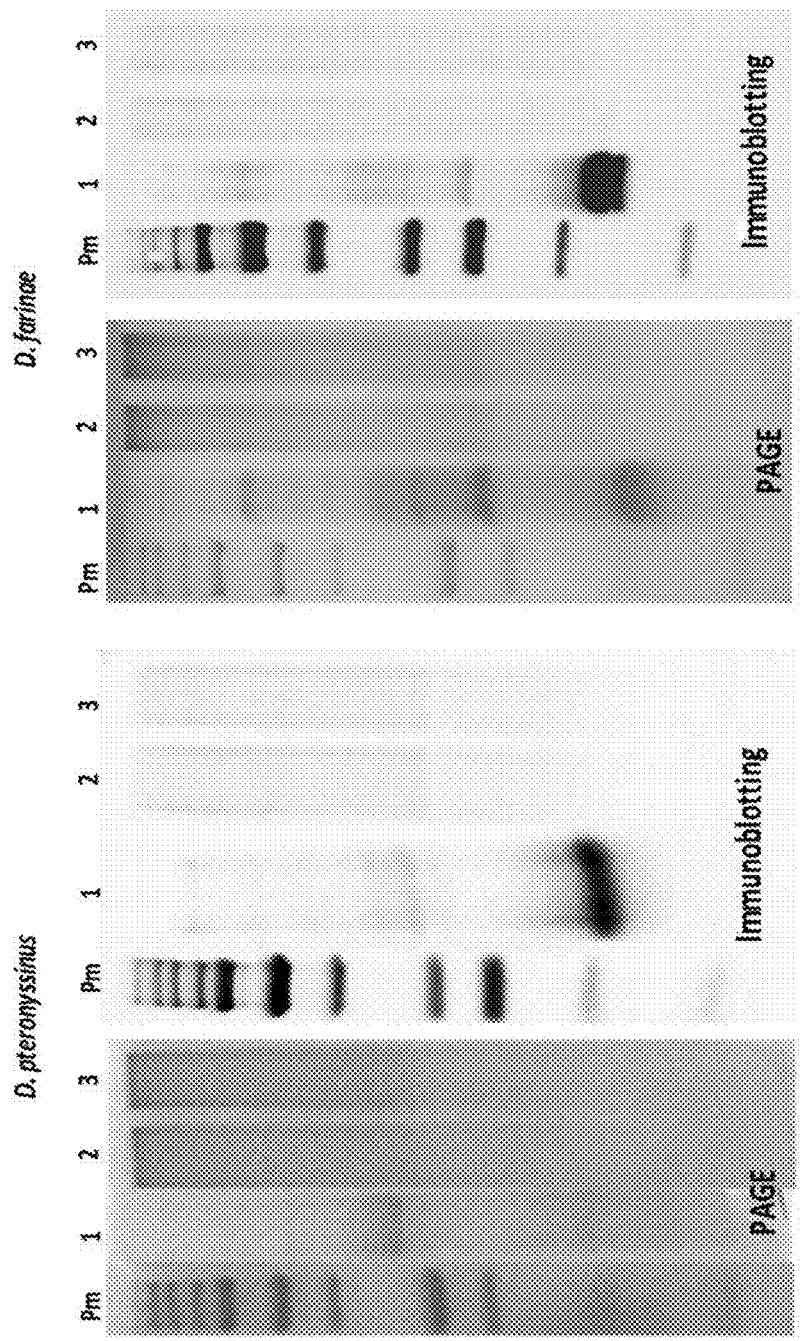
FIG. 20B is an image corresponding to a polyacrylamide gel electrophoresis in the presence of SDS (SDS-PAGE) and immunodetection (immunoblotting) with sera from allergic patients, of an extract of *D. pteronyssinus* and *D. farinae*: IgE reactivity with proteins separated by PAGE. Pm=molecular weights pattern; 1=native allergen; 2=polymerized non-mannosylated allergen; 3=allergen mannosylated with glutaraldehyde.

FIG. 20A shows an inhibition ELISA where it can be appreciated that the polymerized allergens of *D. pteronyssinus* and *D. farinae* conjugated with mannan or not, have similar IgE reactivity which is less than that observed in the native allergens. FIG. 20B shows the bands corresponding to the allergenic protein of both mite species, both in gel electrophoresis and in the immunodetection performed with serum from allergic patients, whereas in the lanes corresponding to the polymerized allergen and to the polymerized and mannosylated allergen no bands (PAGE-SDS) or IgE binding (immunodetection) is observed.

5.2.—Human Basophils Activation Tests Ex Vivo

Assessment was done on the capacity of the different preparations of *Phleum pratense* and *D. farinae* to activate basophils of patients allergic to those allergens.

Material and Methods

Assessment on activation of basophils was carried out using the commercial kit BASOTEST® (ORPEGEN Pharma, Heidelberg, Germany), which allowed measurement of the percentage of basophil activation in peripheral blood by flow cytometry. Procedure:

1—Extracting peripheral venous blood in a tube with heparin sodium.

2—Incubating the blood with the stimulation buffer (containing IL-3)

3—Stimulation with allergens from *P. pratense* and *D. farinae* (native, polymer and polymer-mannan). A negative control (only with washing buffer) and a positive control (chemotactic peptide N-formyl-methionine-leucine-phenylalanine (fMLP)) are also included.

4—Labelling of cells with fluorochrome-conjugated monoclonal antibodies (anti-CD203c and anti-CD63.FITC). Double positive cells (CD203c/CD63) reflect the activated basophils.

5—Lysis of erythrocytes with hypotonic buffer.

6—The analysis was carried out in a FC500 cytometer (Beckman Coulter). The specific labelling for determining activated basophils was: CD203c+ and CD63+.

Results

Figure 21:
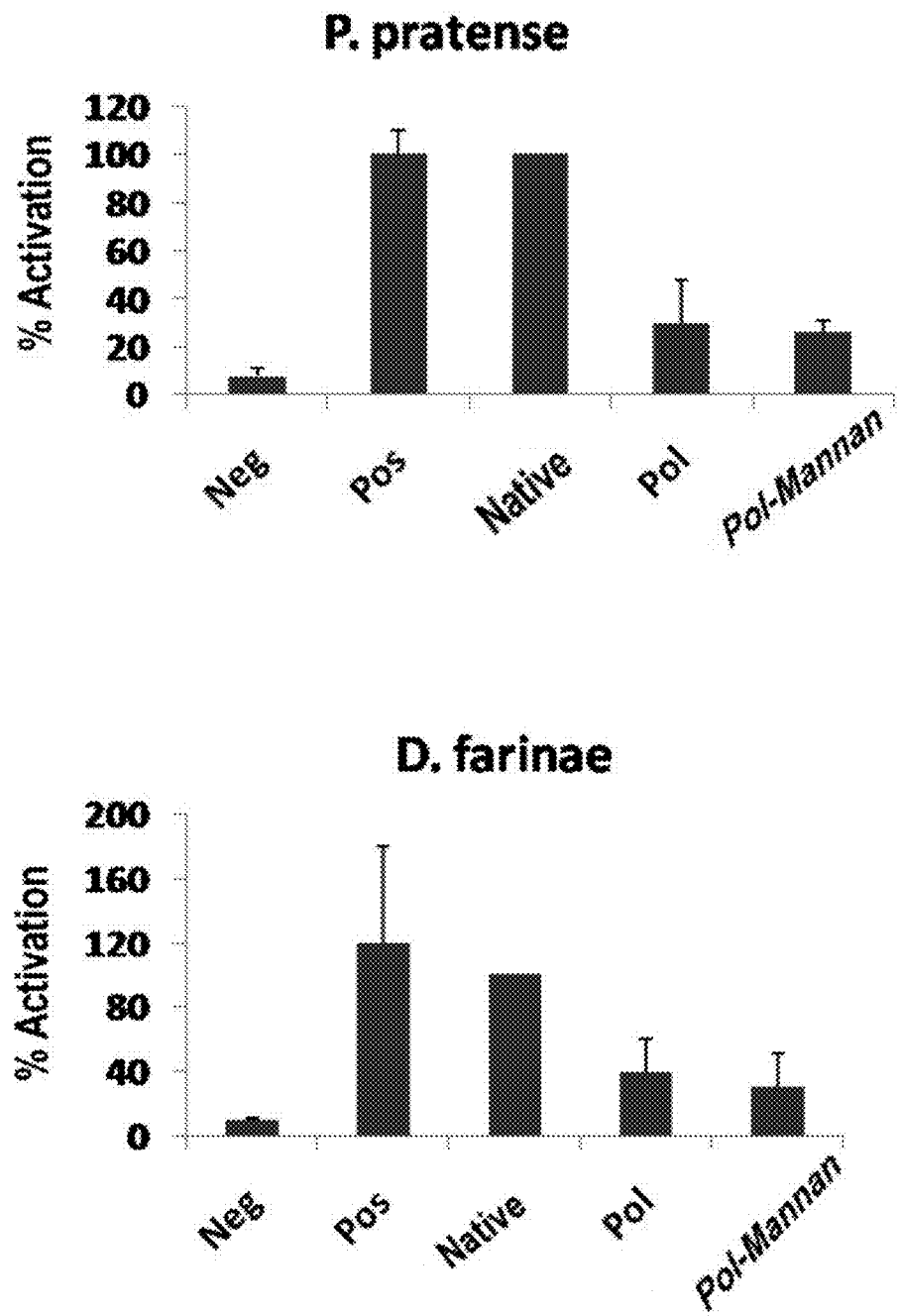
FIG. 21. It is a group of charts showing the results of ex vivo basophil activation tests in patients allergic to *Phleum pratense* or *D. farinae* with the same protein concentration of unpolymerized extracts (native), polymerized (Pol) or polymerized with mannan (Pol Mannan). The analysis of basophils activation was performed by flow cytometry using the BASOTEST® kit.

Percentage of activated basophils (CD203c+CD63+) after incubation with each one of the unpolymerized allergens (native) was, as it was to be expected, high and similar to that obtained with the positive control of the assay. On the other hand, the activation degree decreased when incubation was performed with polymerized allergens of both *Phleum pratense* and de *D. farinae*. This loss of capacity of the polymers to activate basophils reflects their loss of allergenicity, and, as it is shown in FIG. 21, was comparable to both non-mannosylated and mannosylated polymers. All this indicates that mannosylated polymers keep their allergenicity reduced for both allergens to the same extent as that shown by conventional polymerized allergens (non-mannosylated).

5.3.—Skin Tests in Allergic Patients (Prick Test)

Assessment was done on the capacity of the different preparations of *Phleum pratense* and *D. farinae* to produce positive skin tests in patients allergic to those allergens.

Material and Methods

Prick Test

The prick test consisted of placing a drop, in duplicate, of each allergen (native, polymer or polymer-mannan) of *P. pratense* and *D. farinae* on the forearm skin of patients allergic to *P. pratense* and *D. farinae* respectively. These allergens, prepared as it has been previously described, were adjusted to the same protein concentration in a 50% buffered glycerol saline solution. The allergen was introduced in the dermis by pricking the skin with a 1 mm lancet through the droplet. The allergen reacts with the patient sensitised mastocytes, through the specific IgE thereof, which release histamine after their activation. The released histamine increases capillary permeability, producing a liquid extravasation which results in a cutaneous papule appearing 20 minutes after pricking.

The papule size ($mm^2$) is considered an allergenicity index for the preparation, this index being higher the larger the surface of the resulting papule.

Statistics:

For descriptive statistics, it was used the average with its respective confidence limits of 95%, the standard deviation, the median with the corresponding first and third quartile, the coefficient of variation and the range of values (maximum and minimum value).

For comparative statistics, it was used the analysis of variance (ANOVA) with Bonferroni correction (for comparison between pairs of values) in the data from the skin tests with mites (*D. farinae*), since these follow a normal distribution. In the case of data from skin tests with *Phleum pratense*, non-parametric tests were used, since these data did not follow a normal distribution. Friedman test was used to compare the three preparations and Wilcoxon test to compare between pairs.

For graphic representation, it was used the boxplot, which represents the median with its respective 25 and 75% quartiles.

Results 5.3.1 The Loss of Allergenicity in the Prick Test with Polymers of *Phleum pratense* Mannosylated with Glutaraldehyde, is Higher than that of the Non-Mannosylated Polymers.

12 patients were studied, 5 men and 7 women, being clinically allergic to pollen from gramineae. The average age was 41 years old, in a range from 11 to 78 years old. The median of the area size of the papule induced by the native extract (not modified) of *Phleum pratense* was 28.4 mm$^2$, being the 25 and 75% quartile values of 23.0 and 43.1 mm$^2$, respectively. The values corresponding to the polymerized extracts were 8.0 mm$^2$ for the median and 8.0 and 19.7 for the quartiles, respectively. For the polymerized and mannosylated extract the values were 0.0 for the median and 0.0 and 5.4 for the quartiles, respectively (Table 3).

The differences between the papule sizes, obtained with the three types of preparations, are very significant (Friedman test, P<0.0001), being also very significant (Wilcoxon test, P<0.0001) between preparation pairs: native-polymerizate, native-mannosylated polymerizate and polymerizate-mannosylated polymerizate. The preparation showing less allergenicity in vivo is the mannosylated polymerizate.

Tables 2 and 3 show the individual values of the area of each of the papules obtained with each preparation, as well as the descriptive statistics of these values and the epidemiological data of the patients (age and sex).

TABLE 2

Epidemiological data (age and sex) of the patients, and values of the area of each one of the papules induced by each preparation.

| Patients | Sex | Age (years) | Histamine (mm$^2$) | Native (mm$^2$) | Pol (mm$^2$) | Pol mannan (mm$^2$) |
|---|---|---|---|---|---|---|
| 1 | M | 70 | 63.59 | 40.69 | 12.56 | 0.00 |
| 2 | F | 29 | 38.47 | 12.56 | 4.52 | 4.52 |
| 3 | M | 27 | 50.24 | 18.09 | 8.04 | 0.00 |
| 4 | F | 78 | 50.24 | 24.62 | 18.09 | 0.00 |
| 5 | F | 54 | 38.47 | 32.15 | 12.56 | 8.04 |
| 6 | F | 63 | 50.24 | 40.69 | 12.56 | 0.00 |
| 7 | F | 25 | 78.50 | 24.62 | 24.62 | 12.56 |
| 8 | F | 33 | 38.47 | 24.62 | 4.52 | 0.00 |
| 9 | M | 24 | 50.24 | 113.04 | 24.62 | 8.04 |
| 10 | M | 11 | 63.59 | 72.35 | 12.56 | 0.00 |
| 11 | M | 46 | 63.59 | 18.09 | 8.04 | 0.00 |
| 12 | F | 35 | 50.24 | 50.24 | 32.15 | 0.00 |
| TOTAL | 5 M 7 F | | | | | |

TABLE 3

Descriptive statistics of the data shown in Table 2.

| Parametre | Age (years) | Histamine (mm$^2$) | Native (mm$^2$) | Pol (mm$^2$) | Pol mannan (mm$^2$) |
|---|---|---|---|---|---|
| Average | 41.3 | 53.0 | 39.3 | 14.6 | 2.8 |
| Upper 95% CI | 53.0 | 59.9 | 55.5 | 19.5 | 5.3 |
| Lower 95% CI | 29.5 | 46.0 | 23.2 | 9.7 | 0.3 |
| Standard deviation | 20.8 | 12.3 | 28.5 | 8.7 | 4.4 |
| Median | 34.0 | 50.2 | 28.4 | 12.6 | 0.0 |
| First quartile | 26.5 | 47.3 | 23.0 | 8.0 | 0.0 |
| Third quartile | 56.3 | 63.6 | 43.1 | 19.7 | 5.4 |
| Coefficient of variation | 50.5 | 23.2 | 72.6 | 59.5 | 160.3 |
| Maximum | 78.0 | 78.5 | 113.0 | 32.2 | 12.6 |
| Minimum | 11.0 | 38.5 | 12.6 | 4.5 | 0.0 |
| n | 12 | 12 | 12 | 12 | 12 |

Figure 22:
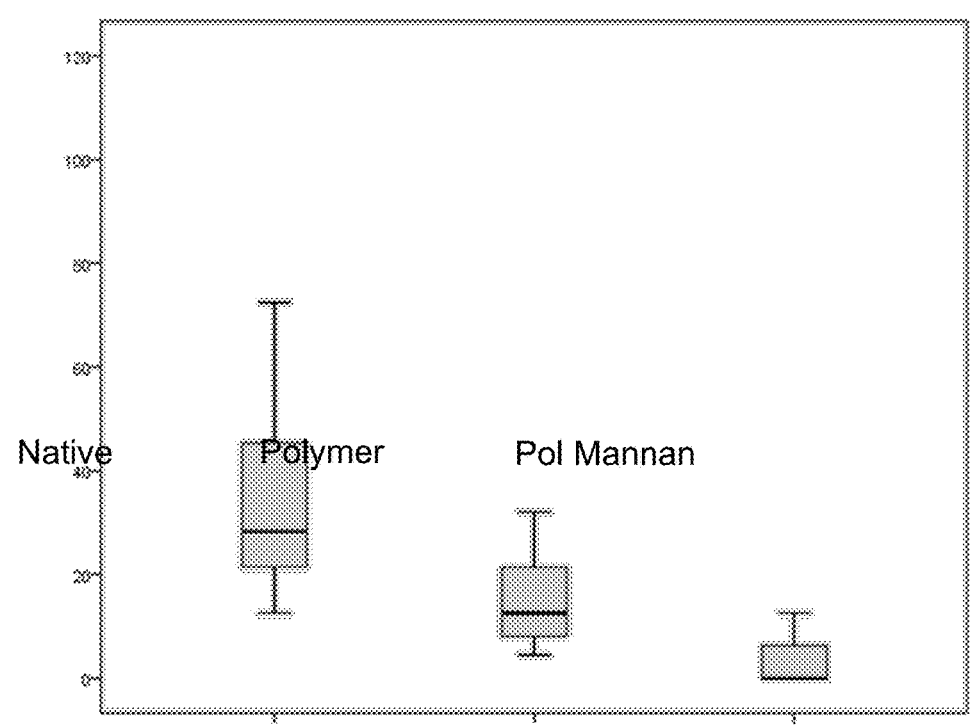
FIG. 22. It is a chart showing the results of the assays on the response in vivo (prick test) in patients allergic to *Phleum pratense* with the same protein concentration of unpolymerized extracts (native), polymerized (Pol) or polymerized with mannan (Pol Mannan).

FIG. 22 shows through a boxplot the values for the area of the papules obtained with each one of the preparations of *Phleum pratense*. As it can be observed, the skin tests performed with the mannolsylated polymer are virtually negative, which involves a decrease with respect to the non-mannosylated polymer, which is in turn much lower than that of the native antigen (unpolymerized). All that indicates a loss of allergenicity of the mannosylated polymer of *Phleum pratense*, to the same or greater extent than the conventional polymer (non-mannosylated).

5.3.2 The Loss of Reactivity in the Prick Test with Polymers of *D. farinae* Mannosylated with Glutaraldehyde is Comparable to that of the Non-Mannosylated Polymers.

22 patients were studied, 14 men and 8 women, being clinically allergic to *Dermatophagoides farinae*. The average age was 32 years old, in a range from 12 to 82 years old. The median of the area size of the papule induced by the native extract (not modified) of *Dermatophagoides farinae* was 64.2 mm$^2$, being the 25 and 75% quartile values of 54.2 and 72.3 mm$^2$, respectively. The values corresponding to the polymerized extracts were 32.5 mm$^2$ for the median and 1.0 and 45.7 for the quartiles, respectively. For the polymerized and mannosylated extract the values were 24.1 for the median and 16.3 and 33.8 for the quartiles, respectively.

The differences between the papule sizes, obtained with the three types of preparations, are very significant (ANOVA test, P<0.0001), being also very significant (Bonferroni correction, P<0.0001) between preparation pairs: native-polymerizate and native-mannosylated polymerizate. The two preparations show a very important decrease in vivo in allergenicity compared to the unpolymerized allergen.

Tables 4 and 5 show the individual values of the area of each of the papules obtained with each preparation, as well as the descriptive statistics of these values and the epidemiological data of the patients (age and sex).

TABLE 4

Epidemiological data (age and sex) of the patients, and values of the area of each one of the papules induced by each preparation.

| Patients | Sex | Age (years) | Histamine (mm$^2$) | Native (mm$^2$) | Pol (mm$^2$) | Pol mannnan (mm$^2$) |
|---|---|---|---|---|---|---|
| 1 | M | 49 | 12.13 | 29.53 | 1.00 | 18.19 |
| 2 | M | 44 | 69.01 | 118.71 | 71.61 | 44.47 |
| 3 | M | 21 | 62.90 | 37.03 | 1.00 | 1.00 |
| 4 | F | 28 | 43.35 | 64.10 | 18.06 | 15.72 |
| 5 | M | 33 | 47.17 | 81.21 | 35.75 | 25.50 |
| 6 | M | 34 | 57.54 | 66.60 | 29.22 | 29.76 |
| 7 | F | 36 | 46.91 | 88.72 | 39.06 | 33.00 |
| 8 | F | 48 | 34.89 | 57.84 | 1.00 | 1.00 |
| 9 | M | 28 | 26.36 | 70.83 | 48.32 | 61.81 |
| 10 | M | 37 | 24.65 | 54.45 | 41.31 | 22.77 |
| 11 | M | 19 | 66.21 | 60.86 | 1.00 | 1.00 |

TABLE 4-continued

Epidemiological data (age and sex) of the patients, and values of the area of each one of the papules induced by each preparation.

| Pa-tients | Sex | Age (years) | Hista-mine (mm$^2$) | Native (mm$^2$) | Pol (mm$^2$) | Pol mannnan (mm$^2$) |
|---|---|---|---|---|---|---|
| 12 | F | 20 | 67.72 | 100.09 | 77.24 | 77.67 |
| 13 | M | 18 | 43.52 | 81.25 | 51.32 | 34.10 |
| 14 | F | 27 | 49.04 | 50.75 | 51.37 | 31.38 |
| 15 | M | 21 | 26.56 | 65.05 | 1.00 | 40.48 |
| 16 | M | 38 | 23.56 | 18.73 | 1.00 | 18.87 |
| 17 | M | 22 | 55.55 | 24.52 | 41.52 | 19.27 |
| 18 | M | 44 | 36.73 | 54.66 | 47.14 | 30.84 |
| 19 | F | 27 | 52.12 | 1.00 | 1.00 | 1.00 |
| 20 | M | 37 | 81.87 | 77.56 | 25.28 | 40.34 |
| 21 | F | 28 | 69.38 | 70.46 | 20.81 | 1.00 |
| 22 | F | 35 | 31.67 | 118.45 | 41.12 | 21.50 |
| TOTAL | 14 M 8 F | | | | | |

TABLE 5

Descriptive statistics of the data shown in Table 4

| Parametre | Age (years) | Histamine (mm$^2$) | Native (mm$^2$) | Pol (mm$^2$) | Pol mannan (mm$^2$) |
|---|---|---|---|---|---|
| Average | 31.5 | 46.8 | 63.3 | 29.4 | 25.9 |
| Upper 95% CI | 35.5 | 54.4 | 75.7 | 39.4 | 34.3 |
| Lower 95% CI | 27.6 | 39.1 | 50.8 | 19.3 | 17.6 |
| Standard deviation | 9.5 | 18.4 | 29.8 | 24.0 | 19.9 |
| Median | 30.5 | 47.0 | 64.6 | 32.5 | 24.1 |
| First quartile | 23.3 | 32.5 | 51.7 | 1.0 | 16.3 |
| Third quartile | 37.0 | 61.6 | 80.3 | 45.7 | 33.8 |
| Coefficient of variation | 30.1 | 39.3 | 47.1 | 81.8 | 76.7 |
| Maximum | 49.0 | 81.9 | 118.7 | 77.2 | 77.7 |
| Minimum | 18.0 | 12.1 | 1.0 | 1.0 | 1.0 |
| n | 22 | 22 | 22 | 22 | 22 |

Figure 23:
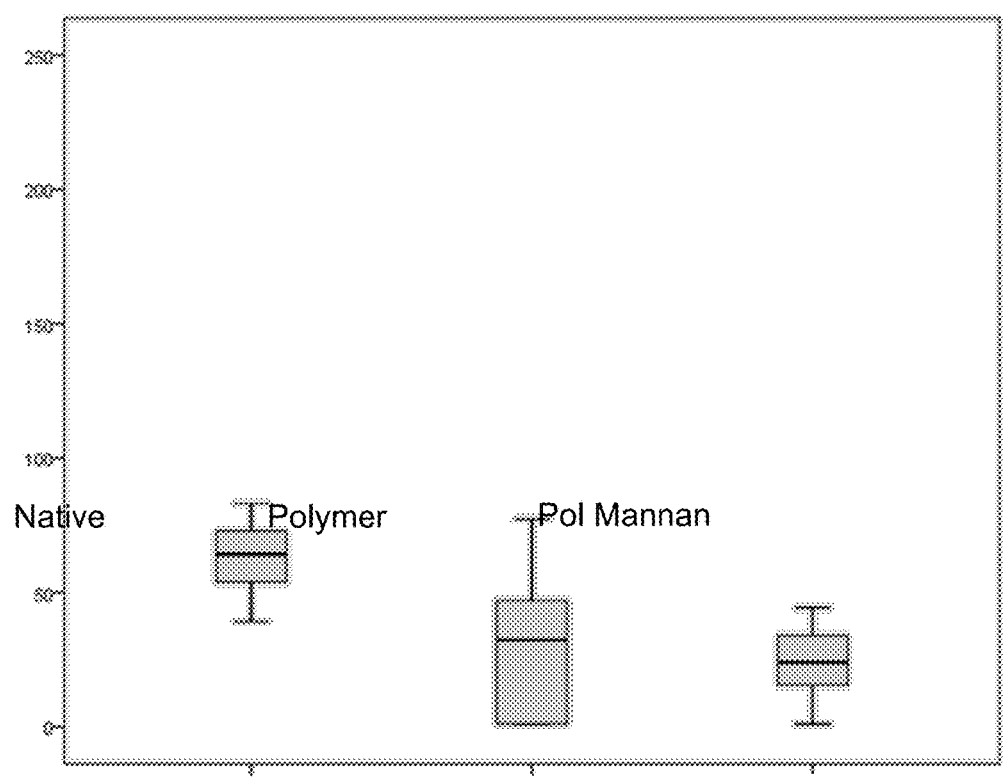
FIG. 23. It is a boxplot of the values showing the results of the assays on the response in vivo (prick test) in patients allergic to *D. farinae* with the same protein concentration of unpolymerized extracts (native), polymerized (Pol) or polymerized with mannan (Pol Mannan).

FIG. 23 shows through a boxplot the values for the area of the papules obtained with each one of the preparations of *D. farinae*. As it can be observed, the skin tests performed with the mannosylated polymer are similar to those with the non-mannosylated polymer, and at the same time is much lower than those of the native antigen (unpolymerized). All that indicates a loss of allergenicity of the mannosylated polymer from *D. farinae* to the same extent as the conventional polymer (non-mannosylated)

Example 6

Polymers Mannosylated Using Glutaraldehyde, are Better Captured by Dendritic Cells than Non-Mannosylated Polymers.

Material and Methods

Dendritic cells (DCs) were induced from peripheral blood monocytes of healthy donors, cultured for 5 days with GM-CSF and IL-4. The DCs thus obtained (immature) were exposed to polymers of *Phleum pratense* (with or without conjugated mannan) prepared as it has been previously described, to assess the uptake by these cells. The uptake assays were realized after 2 hours of contact between the DC and the preparation by means of flow cytometry, using the autofluorescence of the extract from *Phleum pratense* due to the pigments thereof. Two parameters were assessed: a) quantity of allergen captured by the DCs (uptake rate); b) percentage of cells showing internalisation capacity. Additionally, uptake assays were carried out with allergens of *Phleum pratense* previously labelled with a fluorochrome (Alexa M 488) through cysteines. The results were analysed by flow cytometry and confocal microscopy.

Results

Figure 24A:
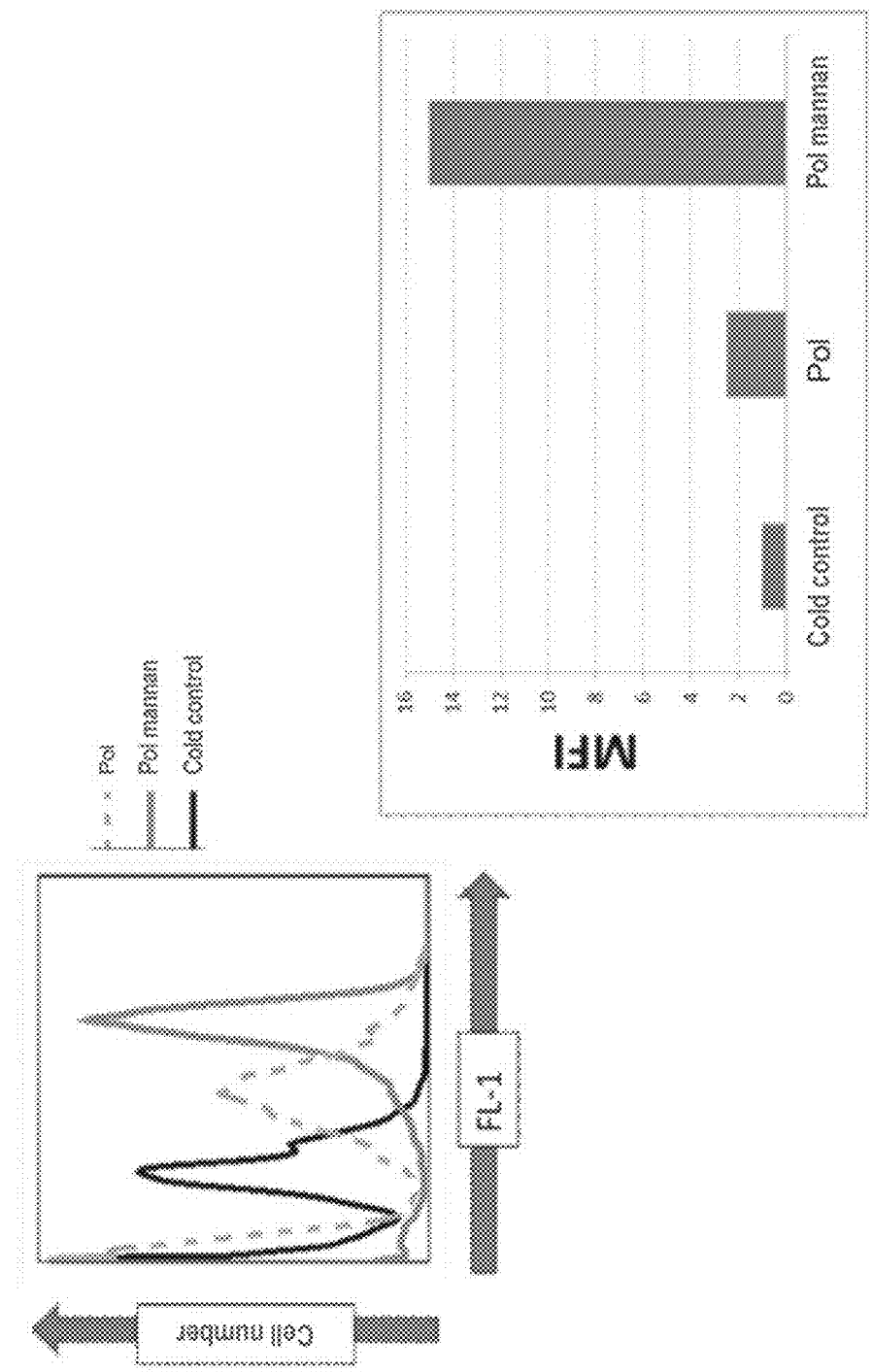
FIG. 24A is a graphic representation showing the results obtained in the assays on the uptake of dendritic cells (DC) derived from human monocytes with allergens from polymerized (Pol) *Phleum pratense* (Pol) or polymerized and mannosylated (Pol Mannan) *Phleum pratense*. The assays were performed by flow cytometry making use of the autofluorescence of the pigments associated to this gramineae extract.
Figure 24B:
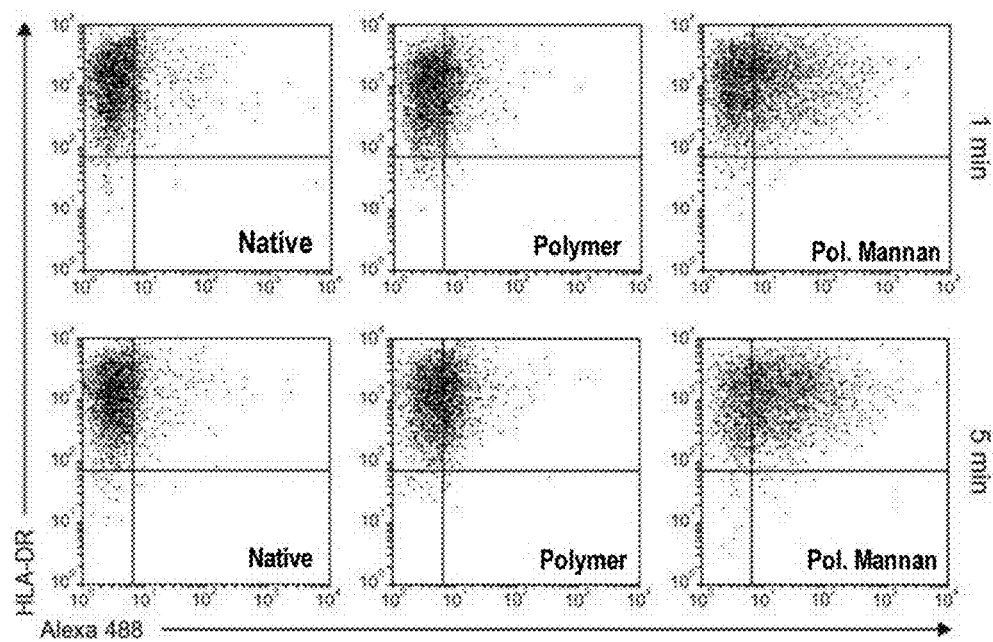
Figure 24B:
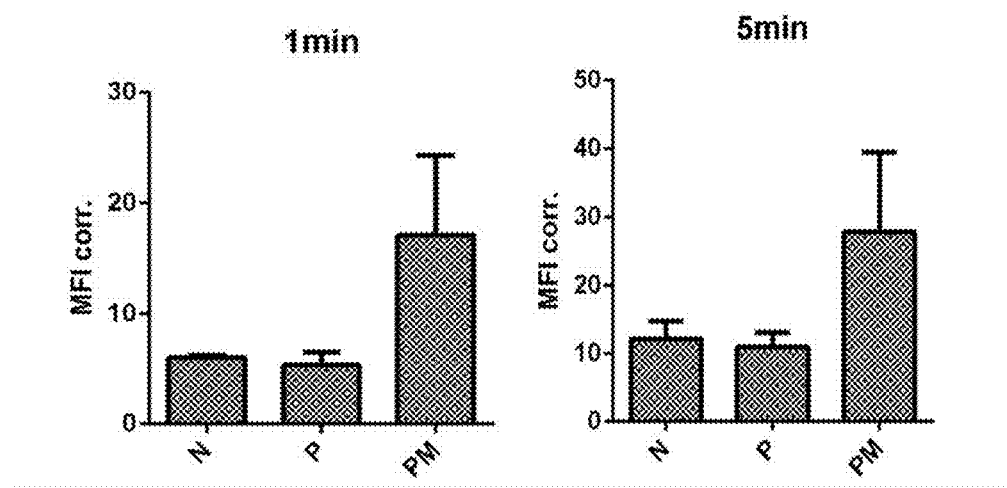
Figure 24C:
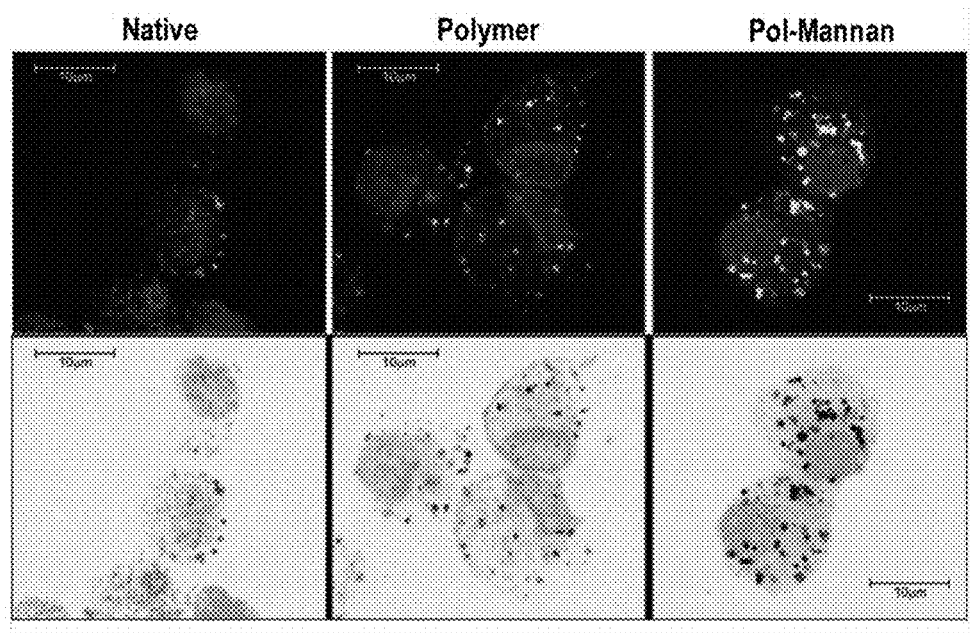
FIG. 24C is a confocal microscopy sample representative of a microscopic area, in order to appreciate the uptake difference among the different fluoresceinated preparations (Alexa 488) by the DCs after 30 min incubation. The fluorescence associated to the different complexes can be seen in the figure in the form of small white spots inside the cells (upper panel in positive and the same in the lower panel in negative for a better identification of the fluorochrome captured, black spots).

As it can be observed in FIG. 24A, the amount of mannosylated polymer of *Phleum pratense* autofluorescent captured by the DCs is more than 7 times higher than that captured by the conventional polymer (non-mannosylated), according to the MFI (mean fluorescence index) which reflects the uptake rate. In the left upper side of the same figure, there is represented the amount of cells with capacity of capturing both preparations (polymer of *Phleum pratense*, mannosylated and non-mannosylated). As it can be observed, the percentage of positive cells showing higher fluorescence corresponds to those incubated with the mannosylated polymer. These results were confirmed labelling with a fluorochrome (Alexa M488) through cysteines. As it can be observed in FIG. 24B, the number of double positive cells (identified as HLA-DR and Alexa 488) was much higher when the cells were incubated with the polymer with mannan, which implied a greater uptake of this preparation. In the lower side of the same Figure the average fluorescence value is represented. As it can be observed, fluorescence intensity was also higher in the DCs incubated with the mannosylated polymer. FIG. 24C shows confocal fluorescence microscopy images, where it can be seen the higher uptake of the DCs incubated (30 min) with the polymer with mannan, compared to the DCs incubated with the non-mannosylated polymer or the native allergen. The conclusion of these experiments is that the mannosylated polymer is captured by a greater number of DCs and that these capture it, also, in a greater amount.

Example 7

Polymers Mannosylated with Glutaraldehyde Induce a Greater Production of IL-10 and IL-6 by Human Dendritic Cells Compared to Non-Mannosylated Polymers.

7.1 Assays of Cytokine Production by Dendritic Cells

Material and Methods

Isolated peripheral blood monocytes from healthy donors were differentiated to dendritic cells (DC) with IL-4 and GM-CSF. These DCs (immature) were incubated with polymerized mannosylated (PM) and non-mannosylated (P) allergens (*Phleum pratense*) at 50 µg/mL. The cytokine concentration was determined in the culture supernatants from these cells 24 hours after their stimulation with the different preparations. The technology used to quantify the cytokines was flow cytometry Multiplex.

Results

Figure 25:
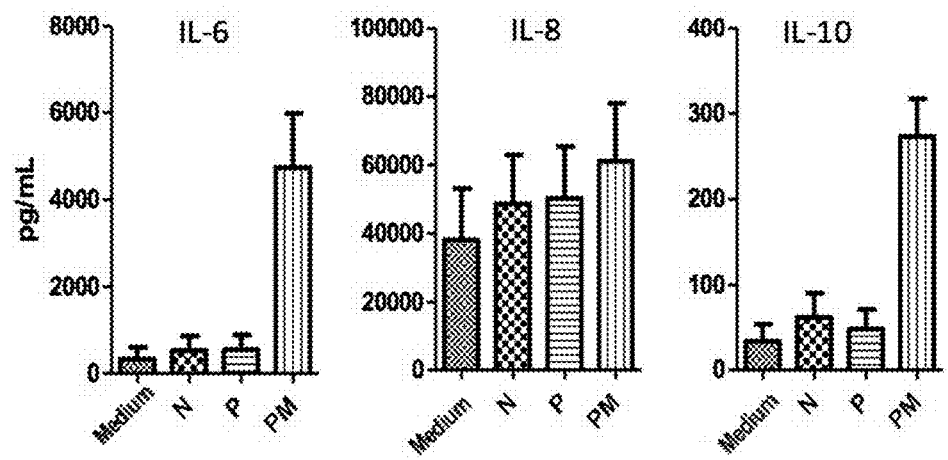
FIG. 25. It is a group of charts showing the cytokine production in supernatants of dendritic cells (DCs) stimulated during 24 hours with extract from native (N) *Phleum pratense*, polymerized (P) *Phleum pratense* (P) and *Phleum pratense* polymerized with mannan (PM).

FIG. 25 shows the average of the 3 independent experiments.

As it can be observed, dendritic cells (DC) incubated with the mannosylated polymer of *Phleum pratense* produce a greater amount of IL-6 and IL-10 than the polymerized non-mannosylated allergen or than the native allergen (unpolymerized). On the contrary, the three preparations induce a similar IL-8 production. These results indicate that human myeloid DCs respond differentially to the mannosylated polymer. The fact that an increase of IL-10 is observed with the mannosylated polymer is very positive for the immunomodulating properties which are sought for with this type of preparations.

Example 8

Polymers Mannosylated with Glutaraldehyde are Comparable with Non-Mannosylated Polymers Regarding their Capacity of Inducing Human Dendritic Cell Maturation 8.1.—Dendritic Cell Maturation Assays Material and Methods Dendritic cells (DC) were induced from monocytes of peripheral blood (buffy coat) from healthy donors, cultured for 5 days with GM-CSF and IL-4. The DCs thus obtained (immature) were exposed to the different allergenic preparations (native, polymer and polymer-mannan) to assess DC maturation in response thereto. The maturation assay was analysed by flow cytometry after 48 hours culture, assessing molecule expression associated to DC maturation (HLA-II (DR), CD80, CD83 and CD86).

Cell labelling procedure: $5 \times 10^5$ cells were used per labelling. Cells were resuspended in PBS and added 1 µg direct antibody (1:100) (conjugated with fluorochrome) or indirect (non-conjugated). They were incubated for 20 minutes at 4° C. in the darkness and subsequently washed with PBS. In the case of the indirect antibody, 1 µg (dilution 1:100) of mouse anti-IgG secondary antibody conjugated with the flouorochrome of interest was added. After washing them twice with PBS, cells were resuspended in a 300-400 µL PBS volume and were finally analysed by flow cytometry (FC 500 Beckman Coultek).

Results 8.1.1 Dendritic Cell (DC) Maturation Derived from Human by *Phleum pratense* Allergens According to the Polymerization and/Mannosylation Thereof.

Figure 26:
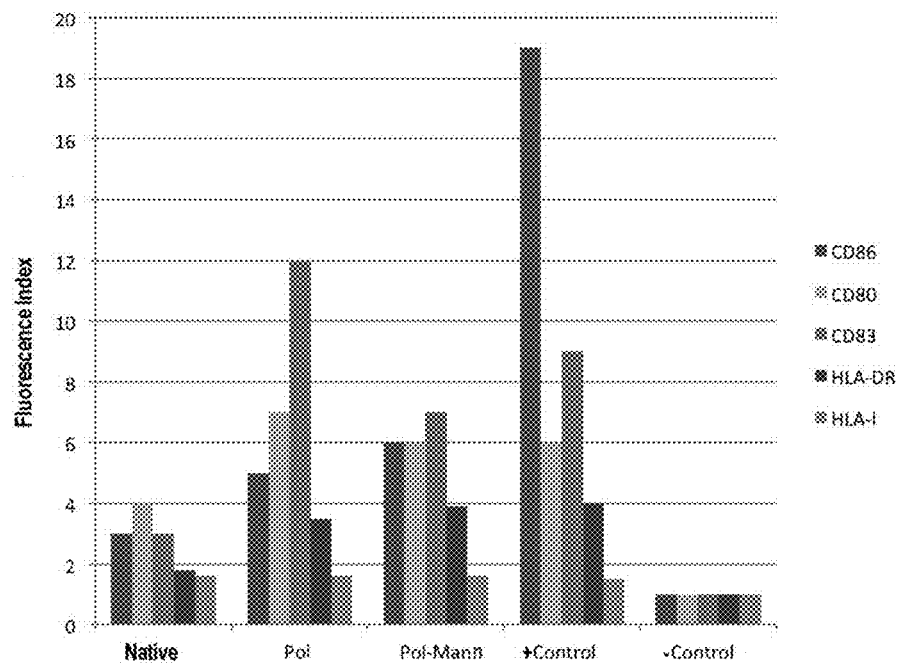
FIG. 26. It is a chart showing the expression of maturation markers in dendritic cells stimulated with allergens from unpolymerized (Native) *Phleum pratense*, polymerized and non-mannosylated (Pol) *Phleum pratense* or polymerized mannosylated (Pol-Man) *Phleum pratense*.

As it can be observed in FIG. 26, polymerized allergens induce myeloid immature DC maturation after these being incubated with said allergens. Maturation degree is assessed according to the DC surface expression of the markers reflected in the figure. All markers associated to maturation are incremented in the DCs incubated with the polymerized allergens with respect to the unpolymerized allergens, there being no significant differences depending on the polymer being mannosylated or not. These results indicate that, from the point of view of DC maturation, the mannosylated polymer of *Phleum pratense* behaves similarly to the conventional polymer (unpolymerized), and therefore shows a maturation index higher than the conventional allergen (unpolymerized)

8.1.2 Maturation of Dendritic Cells Derived from Human Monocytes by *D. farinae* Allergens According to the Polymerization and/Mannosylation Thereof.

Figure 27:
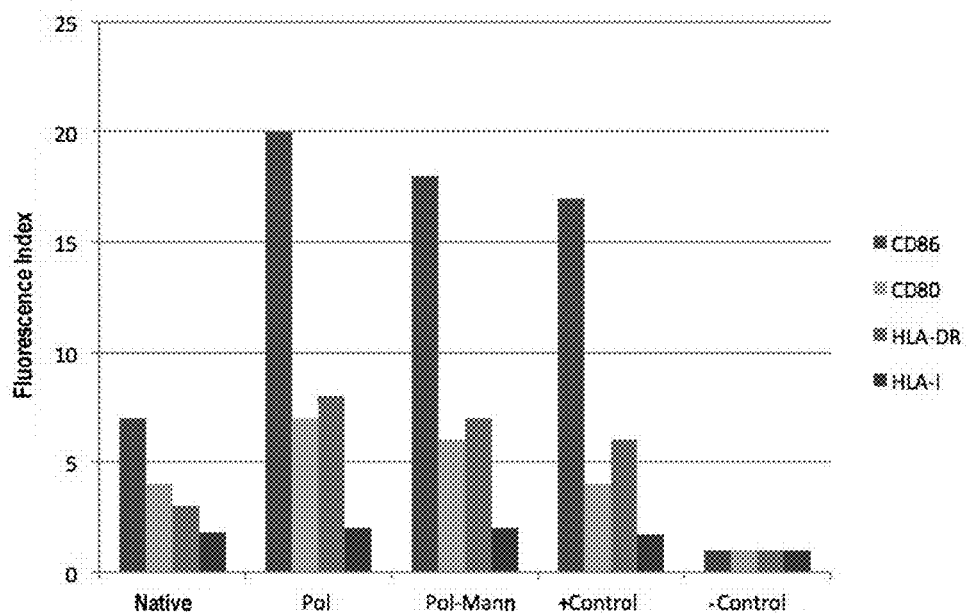
FIG. 27. It is a chart showing the expression of maturation markers in dendritic cells stimulated with allergens from unpolymerized (Native) *D. farinae*, polymerized and non-mannosylated (Pol) or polymerized and mannosylated (Pol-Man).

As it can be observed in FIG. 27, polymerized allergens induce myeloid immature DC maturation after these being incubated with said allergens. Maturation degree is assessed according to the DC surface expression of the markers reflected in the figure. All markers associated to maturation are incremented in the DCs incubated with the polymerized allergens with respect to the unpolymerized allergens, there being no significant differences depending on the polymer being mannosylated or not. These results indicate that, from the point of view of DC maturation, the mannosylated polymer of *D. farinae* behaves similarly to the conventional polymer (unpolymerized), and therefore shows a maturation index higher than the conventional allergen (unpolymerized)

Example 9

Polymers Mannosylated with Glutaraldehyde Improve Induction of IFNgamma and IL-10-Producing T Cells in Ex Vivo Immunization Assays Compared to Non-Mannosylated Polymers Material and Methods Ex Vivo Immunization Assays with Peripheral Blood Human Cells Immunization Protocol Allergen-specific effector T cells were obtained from PBMC of healthy individuals after three rounds of stimulation with autologous mature DCs loaded with the corresponding allergenic extracts. Briefly, the iDCs ($10^6$/mL) were incubated for 8 hours in complete DMEM medium with the corresponding extracts (100 µg/mL) and then were maturated by incubation with peptidoglycan (1 µl/mL). Mature dendritic cells (mDC), previously washed, were incubated again for 6 hours ($10^6$ cells in 1 mL) with the corresponding extracts in complete DMEM medium and immediately afterwards were irradiated (3000 rad). The mDCs irradiated and loaded with the allergens were then distributed in 48-well plates ($10^6$/mL) and were co-cultured together with PBMCs ($10^7$ cells/mL) in the presence of IL-7 (1 µl/mL). The cultures were supplemented with IL-2 (10 U/mL) 5 days after the first stimulation. The same stimulation and expansion process of the PBMCs with DCs loaded with the allergen extracts was repeated three times. The production of cells allergen-specific IFNγ, IL-10 and IL-4 was measured by ELISPOT assay.

Results 9.1.1 *Phleum pratense* Polymers Mannosylated with Glutaraldehyde Improve the IFN-γ and IL-10 Response of the Non-Mannosylated Polymers without Increasing the IL-4 Response.

Figure 28:
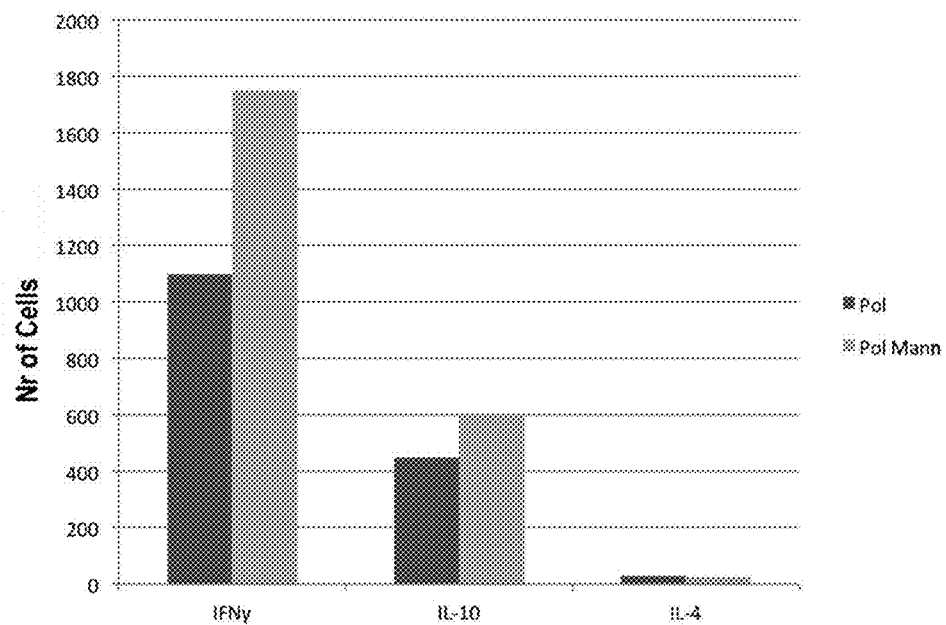
FIG. 28. It is a chart showing the induction of specific IFNγ, IL-10 and IL-4 producing cells after ex vivo immunization assays with polymerized (Pol) or polymerized and mannosylated (Pol Man) allergens from *Phleum pratense*. The amount of producing cells was determined by ELISPOT.

As it is observed in FIG. 28 the number of IFN-γ and IL-10 producing cells is increased in the cultures immunized with the polymerized and mannosylated allergen in the specific response, compared to those cultures immunized in the conventional polymer (non-mannosylated). This increase does not come with a greater number of IL-4 producing cells, which indicates that there has not been a polarization towards a TH2 phenotype. The fact that an increase of IFN-γ and IL-10, without an increase of IL-4, is observed with the mannosylated polymer is very positive for the immunomodulating properties which are sought for with this type of preparations.

9.1.2 The *D. farinae* Allergens Mannosylated with Glutaraldehyde Improve the IFN-γ and IL-10 Response of the Non-Mannosylated Polymers without Increasing the IL-4 Response.

Figure 29:
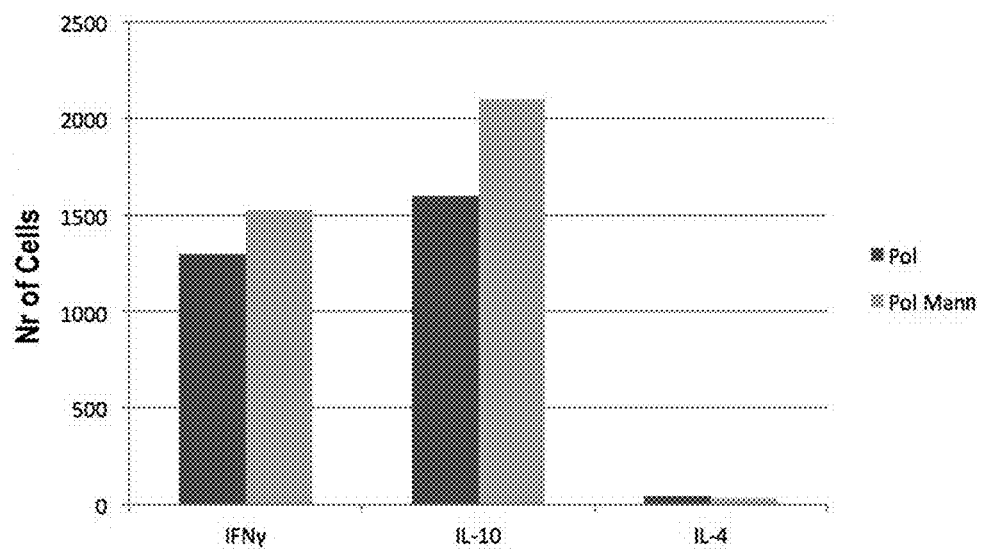
FIG. 29. It is a chart showing the induction of specific IFNγ, IL-10 and IL-4 producing cells after ex vivo immunization assays with polymerized (Pol) or polymerized and mannosylated (Pol Man) allergens from *D. farinae*. The amount of producing cells was determined by ELISPOT.

As it is observed in FIG. 29 the number of IFN-γ and IL-10 producing cells is increased in the cultures immunized with the polymerized and mannosylated allergen in the specific response, compared to those cultures immunized in the conventional polymer (non-mannosylated). This increase does not come with a greater number of IL-4 producing cells, which indicates that there has not been a polarization towards a TH2 phenotype. The fact that an increase of IFN-γ and IL-10, without an increase of IL-4, is observed with the mannosylated polymer is very positive for the immunomodulating properties which are sought for with this type of preparations.

Example 10

Polymers Mannosylated with Glutaraldehyde Improve In Vivo Immune Response Compared to Non-Mannosylated Polymers.

In Vivo Immunization Assays in Mice

Material and Methods

Figure 30:
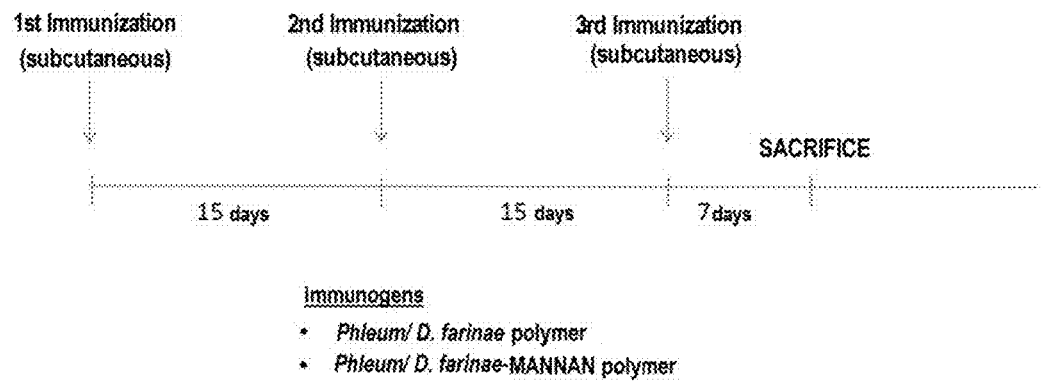
FIG. 30. It is the immunization protocol scheme for Balb/c mice.

Immunizations were carried out with *Phleum pratense* and *D. farinae* allergens with mannosylated and non-mannosylated polymers so as to assess their immunogenic capacity in vivo. Immunizations were realized in Balb/c mice with the protocol shown in FIG. 30.

Figure 31:
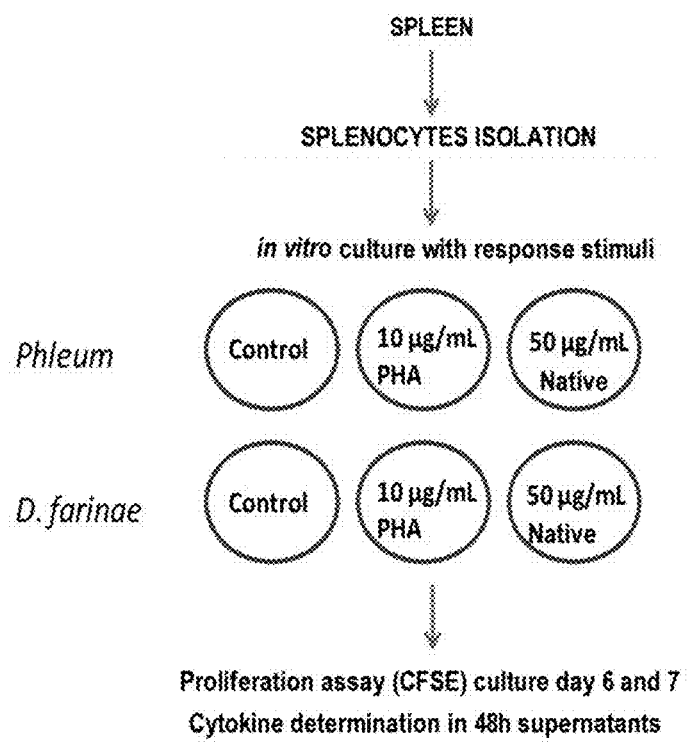
FIG. 31. It is a scheme of the protocol followed in the lymphocytes proliferation assay.

The response to immunization was assessed in the spleen, performing specific lymphoproliferation assays by labelling with CFSE in response to the allergen in its native form. Phytohaemagglutinin (PHA) was used as positive control. Proliferation was determined at culture day 6 and day 7. Quantification of cytokines was also done in the culture supernatant after 48 hours stimulation using the Multiplex flow cytometry technology (FIG. 31). Phytohaemagglutinin (PHA) was used as positive control. Specific IgE levels (*P. pratense* or *D. farinae*) and the IgG1 (as TH2 response markers) and IgG2a (TH1 response marker) levels, were also assessed by ELISA.

Results 10.1 Immunization with Mannosylated Polymers of *Phleum pratense* Produces a Higher Proliferative Response to the Antigenic Stimuli than that with Non-Mannosylated Polymers.

Figure 32:
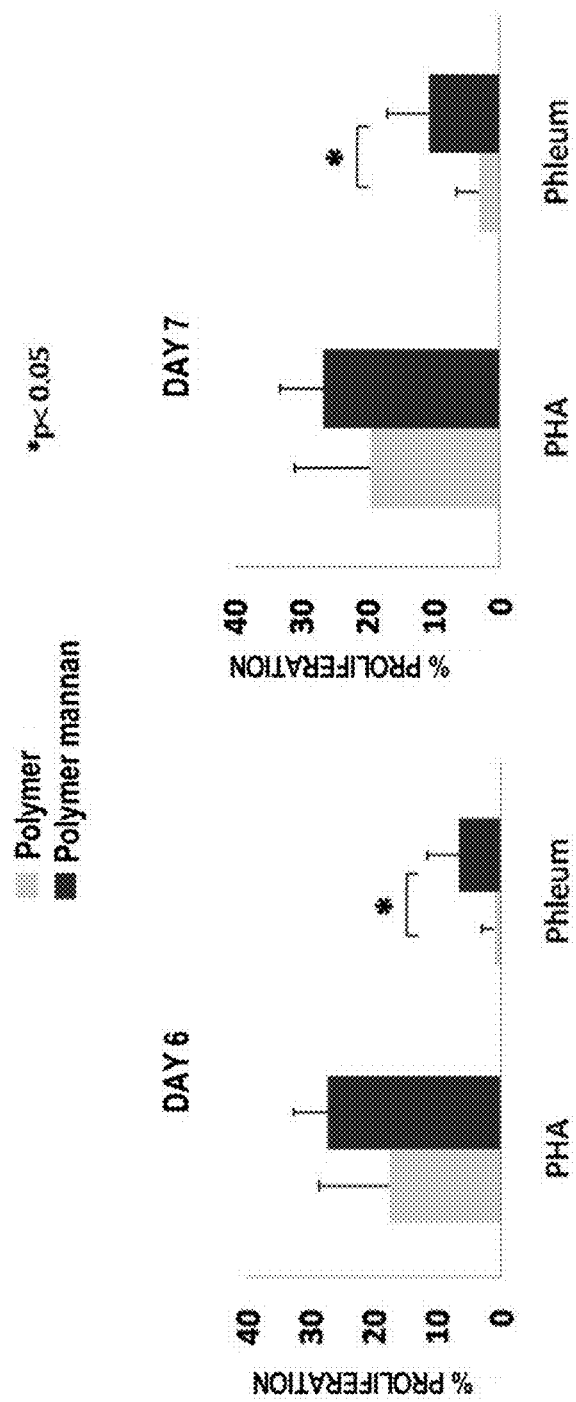
FIG. 32. It is a chart showing the proliferative response in mice immunized with 5 µg of allergens from *Phleum pratense* being polymerized and not mannosylated (Polymer) or polymerized and mannosylated (Polymer mannan). Proliferation assay with CSFE.

As it can be observed in FIG. 32, proliferation percentage, which reflects the number of T cells responding to the antigen, is significantly higher when the responding cells are taken from the spleen of mice immunized with the polymerized and mannosylated allergen, compared to the cells taken from the spleen of mice immunized with the conventional polymerized allergen (unpolymerized). This indicates that the immunogenic properties of the polymerized and mannosylated *Phleum pratense* allergen are significantly higher than those of the non-mannosylated polymer.

10.2 Immunization with Mannosylated Polymers of *D. farinae* Produces a Higher Proliferative Response to the Antigenic Stimuli than that with Non-Mannosylated Polymers.

Figure 33:
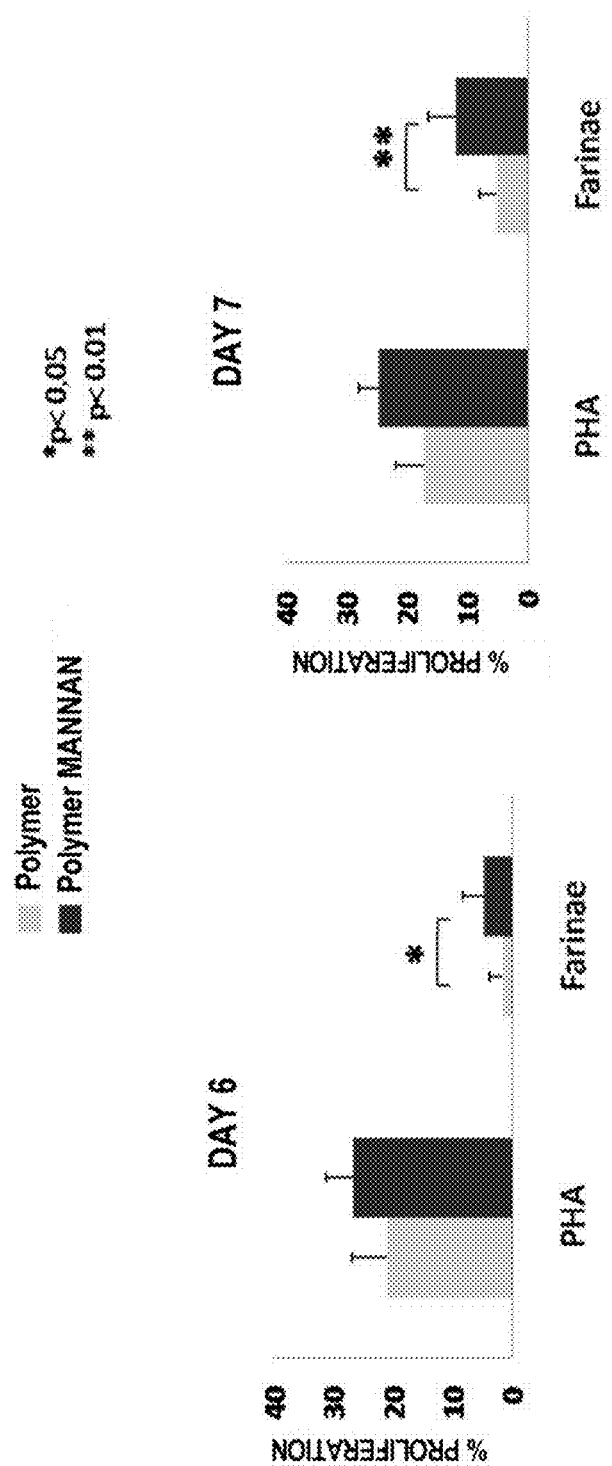
FIG. 33. It is a chart showing the proliferative response in mice immunized with 20 µg of allergens from *D. farinae* being polymerized and not mannosylated (Polymer) or polymerized and mannosylated (Polymer mannan). Proliferation assay with CSFE.

As it can be observed in FIG. 33, proliferation percentage, which reflects the number of T cells responding to the antigen, is significantly higher when the responding cells are taken from the spleen of mice immunized with the polymerized and mannosylated allergen, compared to the cells taken from the spleen of mice immunized with the conventional polymerized allergen (unpolymerized). This indicates that the immunogenic properties of the polymerized and mannosylated *D. farinae* allergen are significantly higher than those of the non-mannosylated polymer.

10.3 Splenocytes of Mice Immunized with Mannosylated *Phleum pratense* Polymers Modify the Cytokine Pattern, with Respect to Non-Mannosylated Polymers.

Figure 34A:
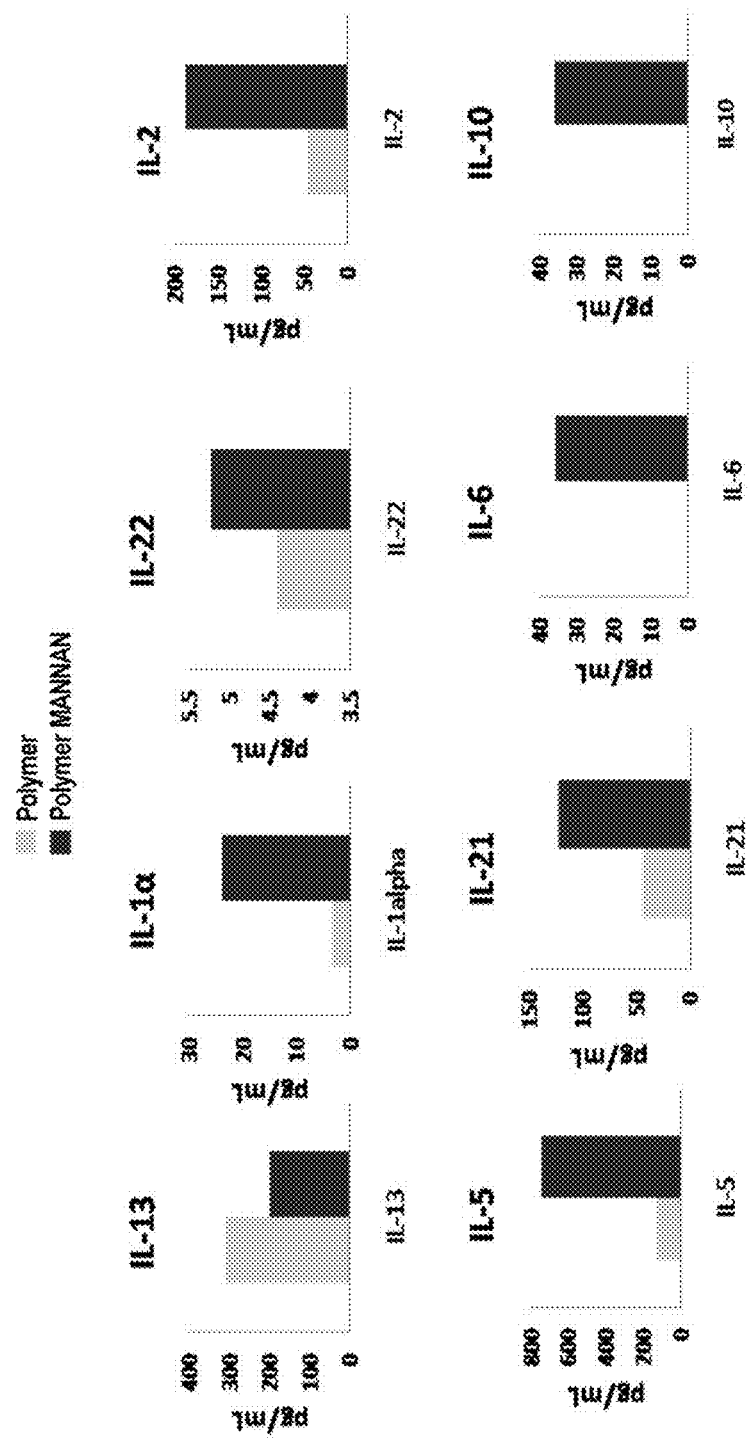
FIG. 34. It is a group of charts (FIGS. 34A and 34B) showing the production of cytokines by splenocytes of mice immunized with polymers from *Phleum pratense* as a response to the native (unpolymerized) allergen from *Phleum pratense*. The bars represent the average of mice from the same group. Grey bars: non-mannosylated polymers; Black bars: mannosylated polymer.
Figure 34B:
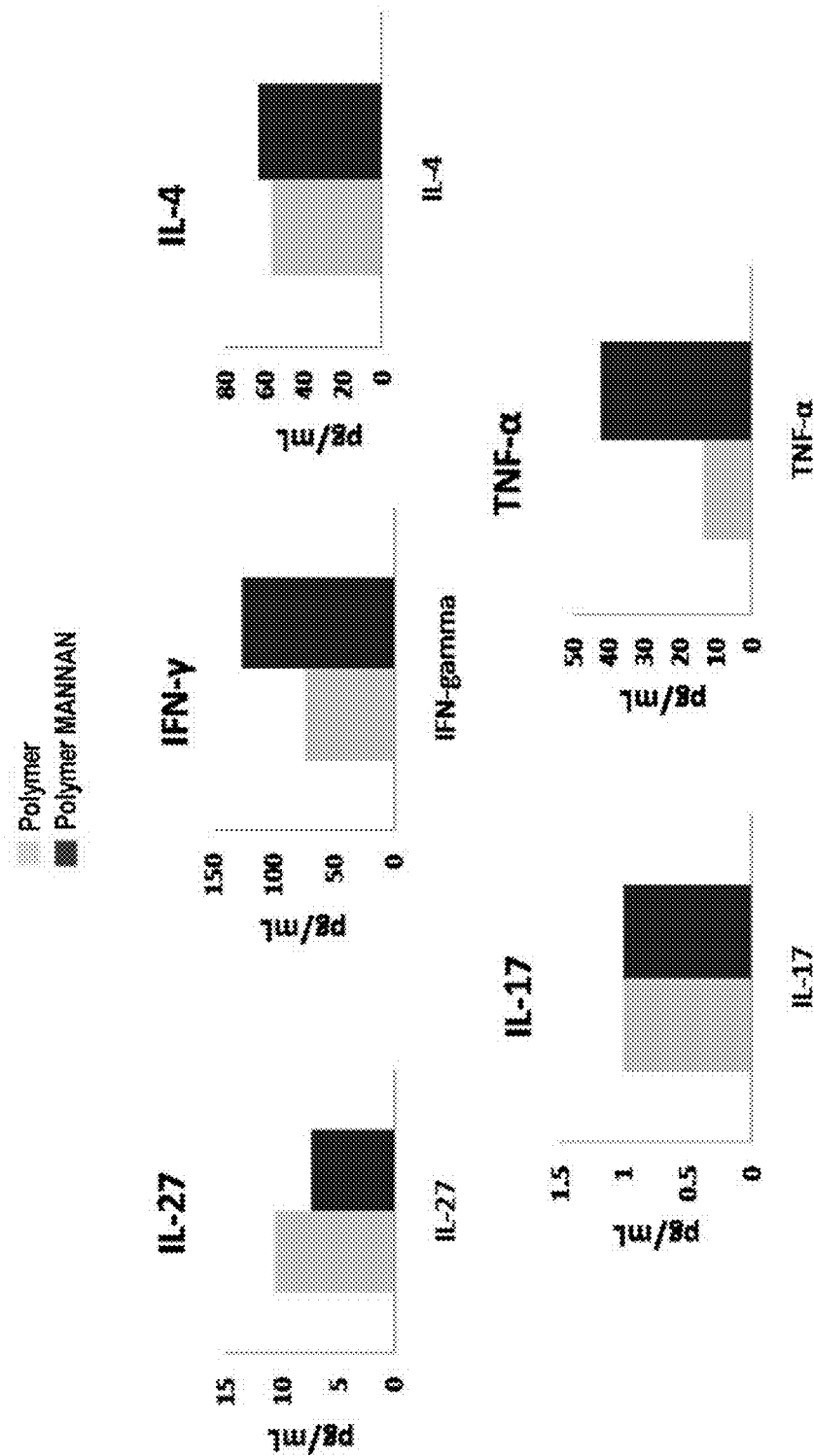

FIG. 34 (FIGS. 34A and 34B) represents the production of the different cytokines obtained in culture supernatants of splenocytes, stimulated with *P. pratense* allergen, from mice immunized with mannosylated and non-mannosylated polymerized allergen. As it can be observed, the pattern of produced cytokines differs for many of them depending on where the splenocytes are from. Variations thereof produced by lymphoid cells are shown in a quantitative way in Table 6.

10.4 Lymphocytes from Mice Immunized with Mannosylated Polymers of *Phleum* Increase IL-10 Production, Compared to that Produced with Non-Mannosylated Polymers.

TABLE 6

Relative in vitro cytokine production by lymphocytes from mice immunized with *Phleum* polymers

| Cytokine | Variation (nr of times) of *Phleum*-Mannan vs. *Phleum* |
|---|---|
| IL-13 | 0.6 |
| IL-22 | 1.2 |
| IL-2 | 4.0 |
| IL-5 | 5.7 |
| IL-21 | 2.8 |
| IL-10 | 361.8** |
| IL-27 | 0.7 |
| IFN-γ | 1.7 |
| IL.4 | 1.1 |
| IL-17 | 1.0 |
| TNF-α | 3.1 |

**Relative increase 100-fold higher than the values obtained in mice immunized with non-mannosylated polymers As it can be observed in Table 6, the greatest variations that may be obtained with respect to the cytokine production of lymphoid origin shown in FIG. 34 (FIGS. 34A and 34B) correspond to the IL-10, which increases more than 300 times in mice immunized with the polymerized and mannosylated allergen, with respect to the production obtained in those immunized with the non-mannosylated polymer. This increase in IL-10 is very positive for the immunomodulating properties which are sought for with this type of preparations.

10.5 Splenocytes from Mice Immunized with Polymers of Mannosylated *D. farinae* Modify the Cytokine Pattern, with Respect to Non-Mannosylated Polymers.

Figure 35A:
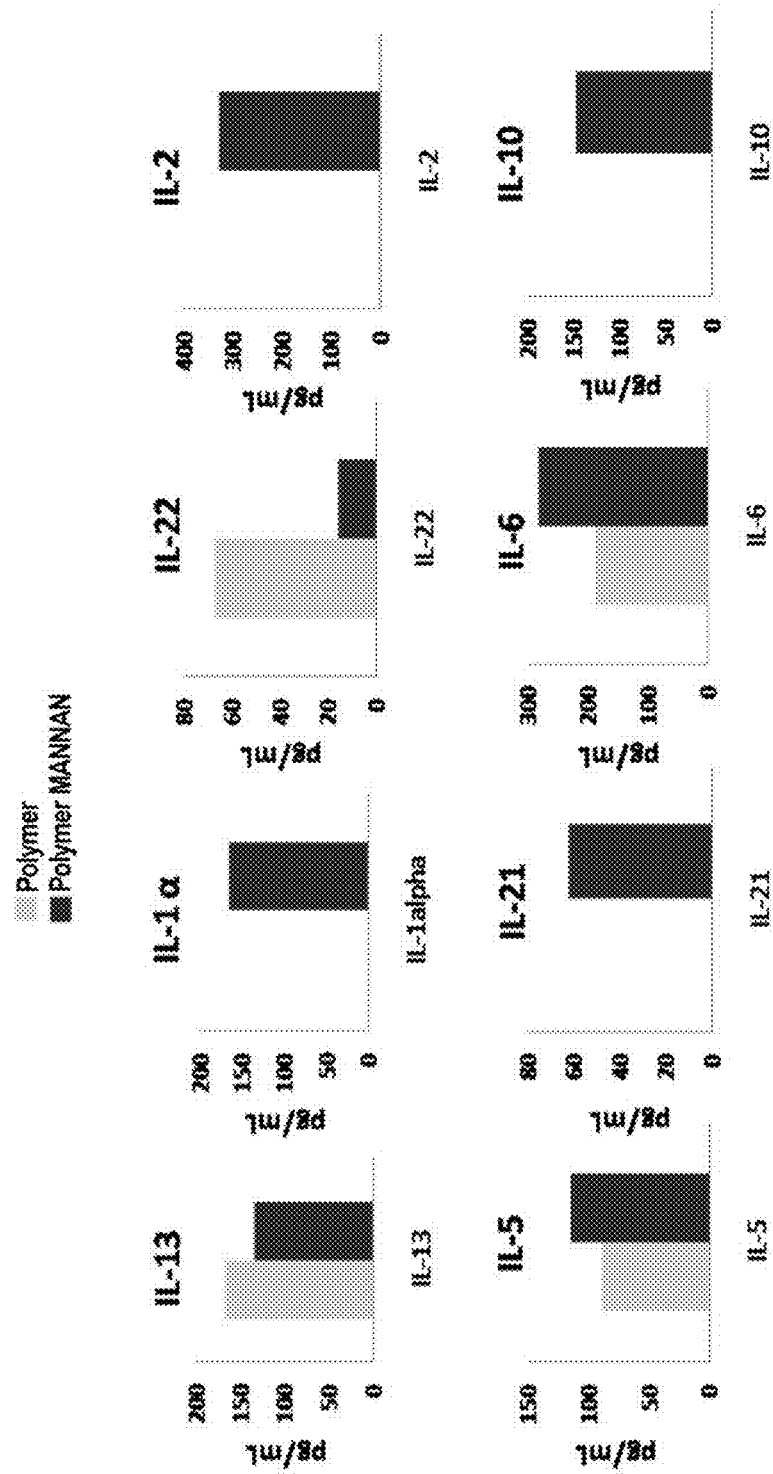
FIG. 35. It is a group of charts (FIGS. 35A and 35B) showing the production of cytokines by splenocytes of mice immunized with polymers from *D. farinae* as a response to the native (unpolymerized) allergen from *D. farinae*. The bars represent the average of mice from the same group. Grey bars: non-mannosylated polymers; Black bars: mannosylated polymer.
Figure 35B:
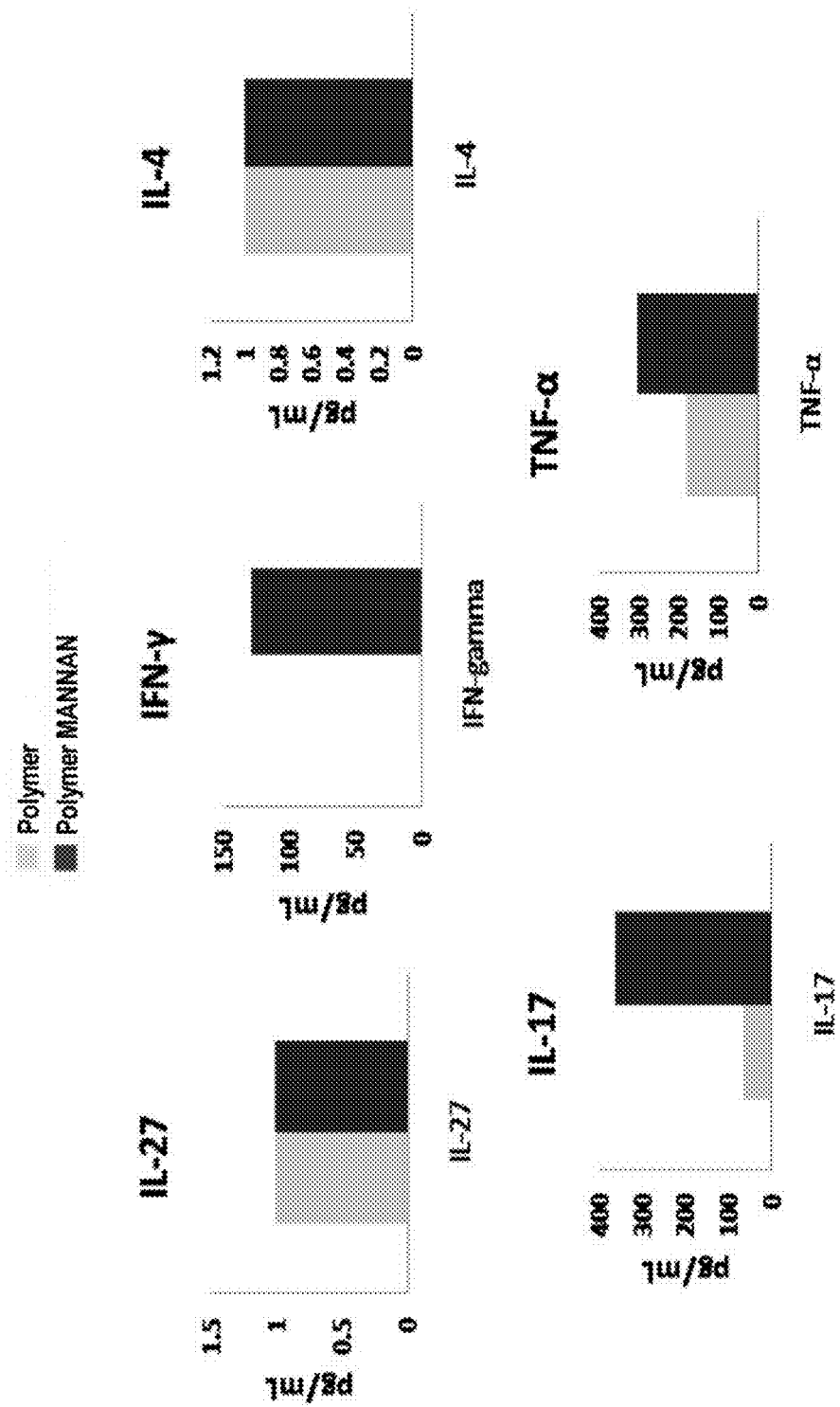

FIG. 35 (FIGS. 35A and 35B) represents the production of the different cytokines obtained in culture supernatants of splenocytes, stimulated with *D. farinae* allergen, from mice immunized with mannosylated and non-mannosylated polymerized allergen. As it can be observed, the pattern of produced cytokines differs for many of them depending on where the splenocytes are from. Variations thereof produced by lymphoid cells are shown in a quantitative way in Table 7.

10.6 Lymphocytes from Mice Immunized with Mannosylated Polymers of *D. farinae* Increase IL-10, IFNγ and IL-2 Production as a Response to the Antigenic Stimuli, Compared to that Produced with Non-Mannosylated Polymers.

TABLE 7

Relative in vitro production of cytokines by lymphocytes from mice immunized with *D. farinae* polymers

| Cytokine | Variation (nr of times) of *D. farinae*-Mannan vs. *D. farinae* |
|---|---|
| IL-13 | 0.8 |
| IL-22 | 0.2 |
| IL-2 | 328.1** |
| IL-5 | 1.3 |
| IL-21 | 61.9* |
| IL-10 | 147.1** |
| IL-27 | 1.0 |
| IFN-γ | 128.7** |
| IL.4 | 1.0 |
| IL-17 | 5.7 |
| TNF-α | 1.7 |

**Relative increase 100-fold higher than the values obtained in mice immunized with polymers without Mannan As it can be observed in Table 7, the greatest variations that may be obtained with respect to the cytokine production of lymphoid origin shown in FIG. 35 (FIGS. 35A and 35B) correspond to the IL-2, IL-10 and IFN-γ, which increases more than 300, 145 and 125 times in mice immunized with the polymerized and mannosylated allergen, with respect to the production obtained in those immunized with the non-mannosylated polymer. This increase, especially in IL-10 and IFN-γ, is very positive for the immunomodulating properties which are sought for with this type of preparations.

10.7 The Specific Antibody Response in Mice Immunized with High Doses of Polymerized and Mannosylated *Phleum pratense* Polymers, Favours the IgG/IgE Ratio with Respect to Non-Mannosylated Polymers.

Figure 36A:
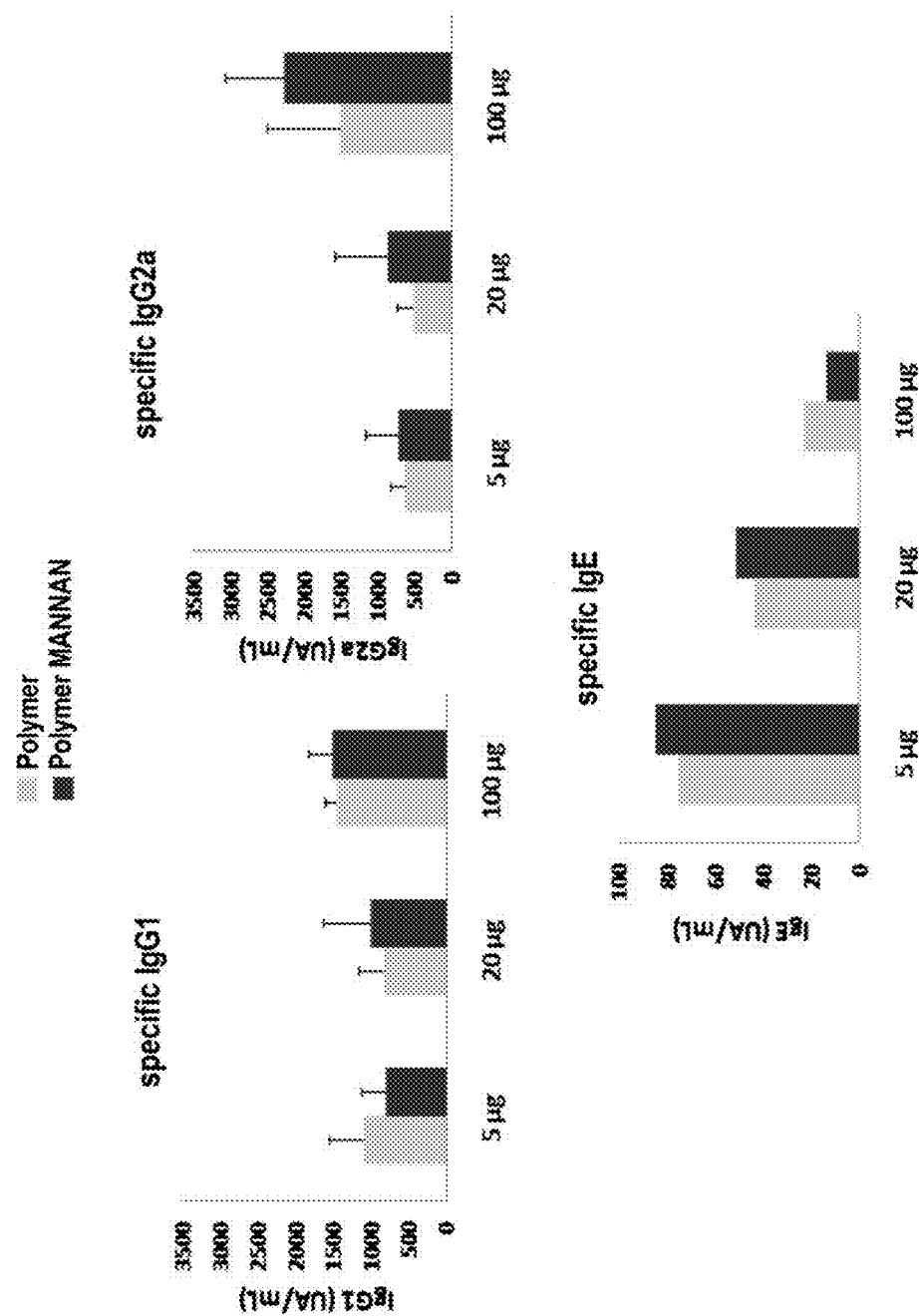
FIG. 36. It is a group of charts (FIGS. 36A and 36B) showing the levels of specific antibodies against allergens from *Phleum pratense* in its native (unpolymerized) form, detected in serum from mice immunized with allergens being polymerized and not mannosylated (Polymer) or polymerized and mannosylated (Polymer Mannan). The lower chart represents the lower chart represents the ratio between the levels of specific antibodies induced with each immunogen of the IgG2a and IgE class.
Figure 36B:
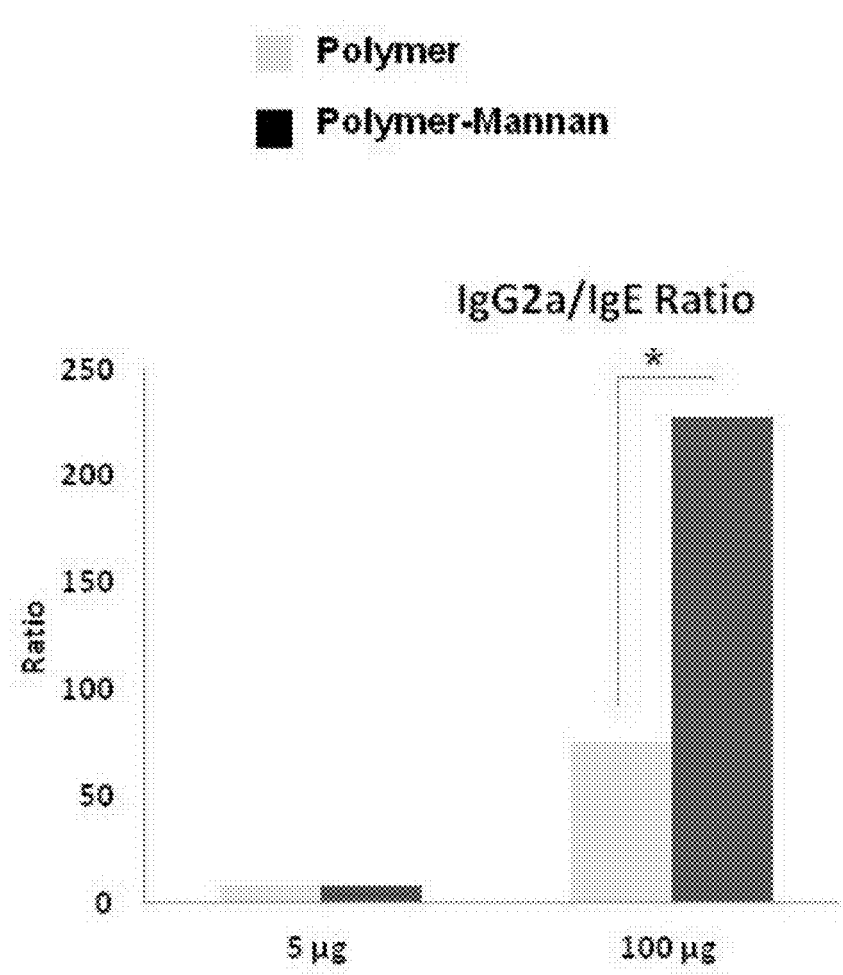

As it can be observed in FIG. 36 (FIGS. 36A and 36B), the specific IgG antibodies response to *Phleum pratense* allergen is higher in the serum from mice immunized with the polymerized and mannosylated allergen than in that with the conventional polymerized allergen (non-mannosylated). On the contrary, the specific IgE antibodies response is lower than that of the conventional polymer. As it can be seen in the figure, the IgG2a/IgE ratio is higher when immunizations are carried out with the polymerized and mannosylated *Phleum pratense* allergen. An increase in this ratio is very positive for the immunomodulating properties which are sought for in this type of preparations, since it indicates an antiallergic polarization of the obtained response.

10.8 The Specific Antibody Response in Mice Immunized with High Doses of Mannosylated *D. farinae* Polymers Favours the IgG/IgE Ratio with Respect to Non-Mannosylated Polymers.

Figure 37A:
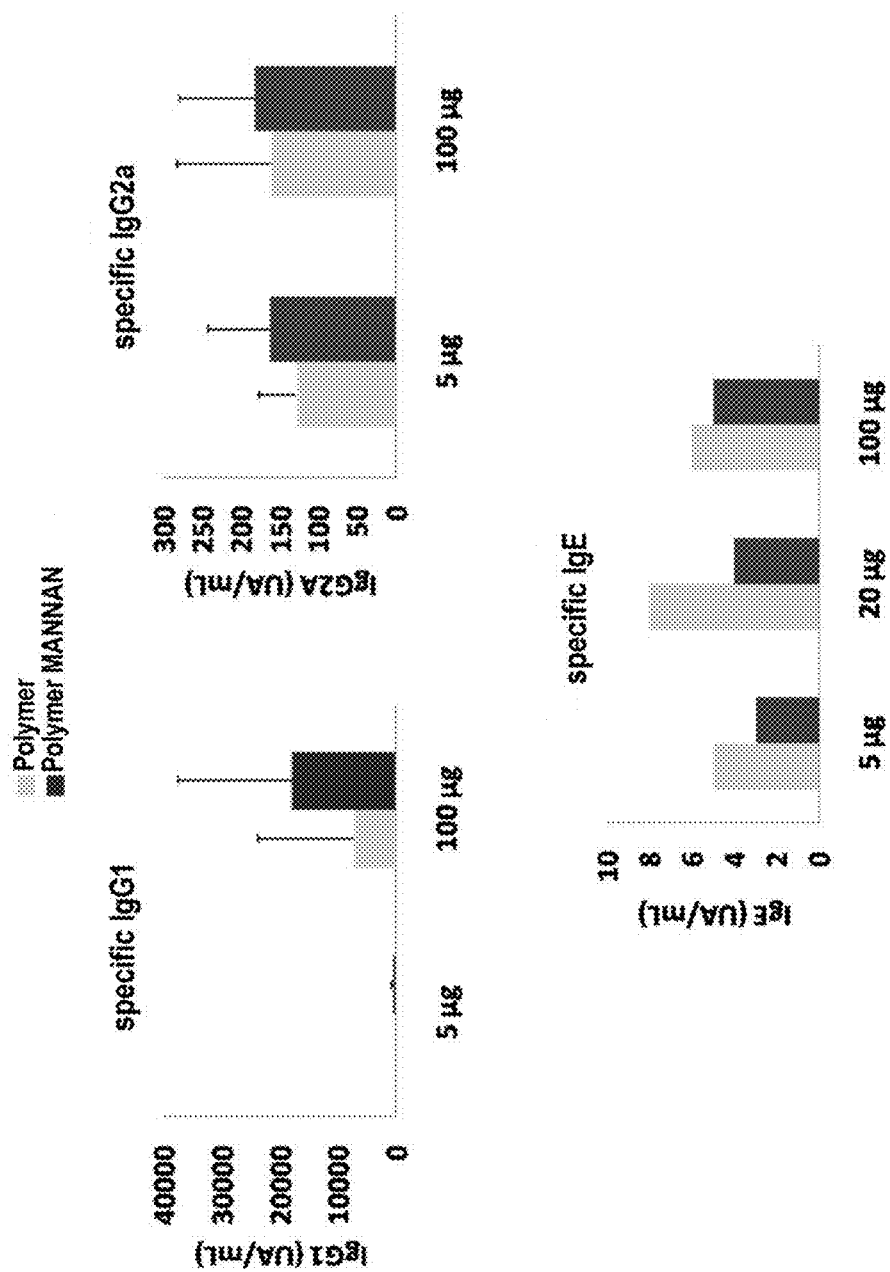
FIG. 37. It is a group of charts (FIGS. 37A and 37B) showing the levels of specific antibodies against allergens from *D. farinae* in its native (unpolymerized) form, detected in serum from mice immunized with allergens being polymerized and not mannosylated (Polymer) or polymerized and mannosylated (Polymer Mannan). The lower chart represents the lower chart represents the ratio between the levels of specific antibodies induced with each immunogen of the IgG2a and IgE class.
Figure 37B:
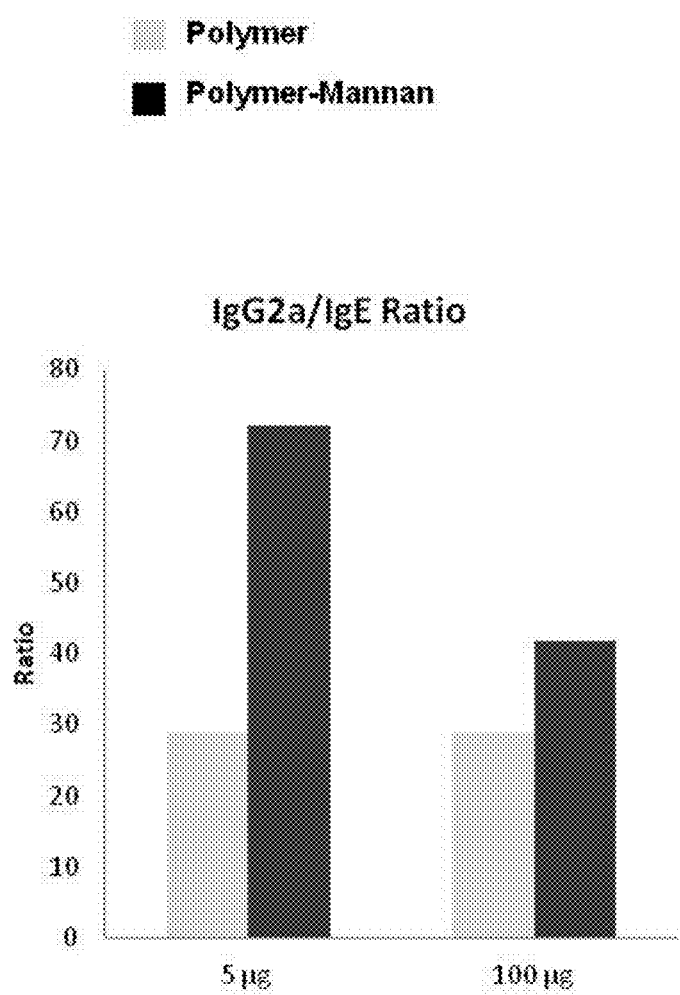

As it is observed in FIG. 37 (FIGS. 37A and 37B), the specific IgG antibodies response to *D. farinae* allergen is higher in the serum from mice immunized with the polymerized and mannosylated allergen than in that with the conventional polymerized allergen (non-mannosylated). On the contrary, the specific IgE antibodies response is lower than that of the conventional polymer. As it can be seen in the figure, the IgG2a/IgE ratio is higher when immunizations are carried out with the polymerized and mannosylated *D. farinae* allergen. An increase in this ratio is very positive for the immunomodulating properties which are sought for in this type of preparations, since it indicates an antiallergic polarization of the obtained response.

The invention claimed is:

1. An immunogenic complex comprising a polymerized antigen, mannan comprising a peptide residue comprising amino groups and a reacted dialdehyde, wherein the polymerized antigen is bound to the amino groups of the mannan by the reacted dialdehyde.

2. The immunogenic complex according to claim 1, wherein the mannan comes from a plant, a fungus or a yeast.

3. The immunogenic complex according to claim 2, wherein the yeast is selected from the group consisting of *Saccharomyces* ssp., *Pichia* ssp. and *Candida* ssp.

4. The immunogenic complex according to claim 1, wherein the amino groups are in the lysine amino acid.

5. The immunogenic complex according to claim 1, wherein the polymerized antigen comprises at least two antigens which are the same or different to each other.

6. The immunogenic complex according to claim 1, wherein the dialdehyde is selected from the group consisting of glutaraldehyde, glyoxal, malonaldehyde, succinaldehyde and adipaldehyde.

7. The immunogenic complex according to claim 1, wherein the antigen is an allergen.

8. The immunogenic complex according to claim 7, wherein the allergen is selected from the group consisting of pollens, proteins or allergenic extracts of mites, epithelia or fungal spores, and combinations thereof.

9. The immunogenic complex according to claim 1, wherein the antigen:mannan ratio ranges between 1:10 and 1:0.1.

10. A process for obtaining an immunogenic complex according to claim 1, which comprises (i) preparing a dissolution comprising an antigen and mannan, (ii) adding a dialdehyde to said dissolution, wherein the mannan comprises amino groups; (iii) comprising the addition of a neutralizing agent to stop the polymerization reaction and also comprising a step (iv) of isolating the immunogenic complex.

11. The process according to claim 10, wherein the mannan comes from a plant, a fungus or a yeast.

12. The process according to claim 11, wherein the yeast is selected from the group consisting of *Saccharomyces* ssp., *Pichia* ssp. and *Candida* ssp.

13. The process according to claim 10, wherein the amino groups are in the lysine amino acid.

14. The process according to claim 10, wherein the polymerized antigen comprises at least two antigens which are the same or different to each other.

15. The process according to claim 10, wherein the dialdehyde is selected from the group consisting of glutaraldehyde, glyoxal, malonaldehyde, succinaldehyde and adipaldehyde.

16. The process according to claim 10, wherein the antigen is an allergen.

17. The process according to claim 10, wherein the antigen:mannan ratio ranges between 1:10 and 1:0.15.

18. A pharmaceutical composition comprising the immunogenic complex according to claim 1 and a pharmaceutically acceptable carrier.

19. The pharmaceutical composition according to claim 18, also comprising an adjuvant, wherein the adjuvant is selected from the group consisting of aluminium hydroxide, calcium phosphate, tyrosine, monophosphoryl lipid A and chitosan.

20. The pharmaceutical composition according to claim 18, wherein the composition is in a solid pharmaceutical form of administration, in a liquid pharmaceutical form of administration, or in a pharmaceutical delivery form comprising a disperse system.

21. A method of stimulating and/or inducing the immune response in a subject comprising administering the immunogenic complex according to claim 1.

22. A method of treatment of an infectious disease, a neoplasm or allergy comprising administering to a subject in need thereof the immunogenic complex according to claim 1.

* * * * *